(12) United States Patent
Hauel et al.

(10) Patent No.: US 8,394,805 B2
(45) Date of Patent: *Mar. 12, 2013

(54) COMPOUNDS

(75) Inventors: Norbert Hauel, Schemmerhofen (DE);
Angelo Ceci, Mittelbiberach (DE);
Henri Doods, Warthausen (DE); Iris Kauffmann-Hefner, Attenweiler (DE);
Ingo Konetzki, Warthausen (DE);
Annette Schuler-Metz, Ulm (DE);
Rainer Walter, Biberach (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 432 days.

This patent is subject to a terminal disclaimer.

(21) Appl. No.: 12/672,460

(22) PCT Filed: Aug. 12, 2008

(86) PCT No.: PCT/EP2008/060562
§ 371 (c)(1),
(2), (4) Date: Apr. 15, 2010

(87) PCT Pub. No.: WO2009/021944
PCT Pub. Date: Feb. 19, 2009

(65) Prior Publication Data
US 2011/0098282 A1    Apr. 28, 2011

(30) Foreign Application Priority Data

Aug. 14, 2007  (WO) ............... PCT/EP2007/058408
Feb. 21, 2008  (WO) ............... PCT/EP2008/052157
Feb. 26, 2008  (EP) ................................. 08102043

(51) Int. Cl.
A61K 31/551   (2006.01)
A61K 31/4965  (2006.01)
C07D 243/08   (2006.01)
C07D 241/04   (2006.01)

(52) U.S. Cl. .............. 514/255.03; 514/218; 540/575; 544/400

(58) Field of Classification Search .......... 514/218, 514/255.03; 544/400; 540/575
See application file for complete search history.

(56) References Cited

U.S. PATENT DOCUMENTS

| 2004/0063725 A1 | 4/2004 | Barth et al. |
| 2006/0084699 A1 | 4/2006 | Barth et al. |
| 2006/0100219 A1 | 5/2006 | Kauffmann-Hefner et al. |
| 2006/0178360 A1 | 8/2006 | Barth et al. |
| 2010/0197664 A1 | 8/2010 | Kauffmann-Hefner et al. |
| 2010/0331544 A1 | 12/2010 | Puder et al. |
| 2011/0077231 A1 | 3/2011 | Hauel et al. |
| 2011/0098282 A1 | 4/2011 | Hauel et al. |

FOREIGN PATENT DOCUMENTS

| CA | 2585535 A1 | 5/2006 |
| EP | 0173552 A1 | 3/1986 |
| JP | 2006516132 A | 6/2006 |
| WO | 9610022 A1 | 4/1996 |
| WO | 0137826 A1 | 5/2001 |
| WO | 02053516 A2 | 7/2002 |
| WO | 03106428 A1 | 12/2003 |
| WO | 2006021544 A1 | 3/2006 |
| WO | 2006035967 A1 | 4/2006 |
| WO | 2006036664 A1 | 4/2006 |
| WO | 2006048209 A1 | 5/2006 |
| WO | 2006071775 A2 | 7/2006 |
| WO | 2008145681 A2 | 12/2008 |
| WO | 2009021944 A1 | 2/2009 |

OTHER PUBLICATIONS

Database EMBL: AL604045; Aug. 29, 2001 "Mouse DNA sequence from clone RP23-418011 on chromosome 11 contains the 3' end of the Ernl gene for endoplasmic reticulum (ER) to nucleus signalling, the 3' end of the Ddx42 gene for DEAD (Asp-Glu-Ala-Asp) box polypeptide 42, the Cd79b gene for CD79B antigen, the Icam2 gene for intercellular adhesion" Database accession No. AL604045 sequences NT82216-82409.

Zarudnaya, Margarita I, et al. "Downstream elements of mammalian pre-mRNA polyadenylation signals: primary, secondary and higher-order structures" Nucleic Acids Research, Oxford University Presss, vol. 31, No. 5, Mar. 1, 2003. pp. 1375-1386.

Molander et al.; Reduction of 2-Acylaziridines by Samarium(II) Iodide. An Efficient and Regioselective Route to Beta-Amino Carbonyl Compounds; Tetrahedron; 1997; vol. 53; No. 26; pp. 8887-8912.

Sartori et al.; Synthesis and activities of new arylsulfonamido thromboxane A2 receptor atagonists; European Journal of Medicinal Chemistry; 1993; vol. 28; pp. 6250-6632.

El-Naggar et al.; Beilstein Registry No. 6007541; Pol. J. Chem.; 1982; Bd. 56; Nr. 10-12; pp. 1279-1285; XP002466545.

El-Naggar et al.; Beilstein Registry No. 6009473; Pol. J. Chem.; 1982; Bd. 56; Nr. 10-12; pp. 1279-1285; XP002466834.

Braichenko et al.; Beilstein Registry No. 2905397; Pharm. Chem. J.; 1972; Bd. 6; Nr. 8; pp. 492-494; XP002466835.

Braichenko et al.; Beilstein Registry No. 2400317; Pharm. Chem. J.; 1972; Bd. 6; Nr. 8; pp. 492-494; XP002466836.

(Continued)

*Primary Examiner* — Sreeni Padmanabhan
*Assistant Examiner* — Sahar Javanmard
(74) *Attorney, Agent, or Firm* — Michael P. Morris; Alan R. Stempel

(57) ABSTRACT

Novel compounds of which the following is exemplary:

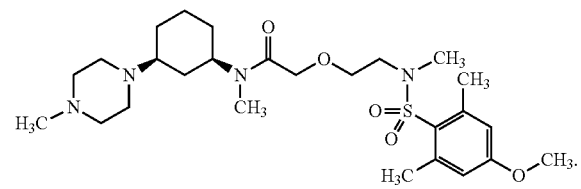

8 Claims, No Drawings

OTHER PUBLICATIONS

Mukherjee et al.; Beilstein Registry No. 9271162; J. Indian Chem. Soc.; 2002; Bd. 79; Nr. 2; pp. 137-141; XP002466837.

Selvamurugan et al.; Beilstein Registry No. 8906721; Indrapal Singh: Synthesis; 2001; Bd. 15; pp. 2239-2246; XP002466838.

Paul et al.; Beilstein Registry No. 2709200; Arch. Pharm. Ber. Dtsch. Pharm. Ges; 1968; Bd. 301; pp. 512-519; XP002466839.

El-Sharief et al.; Beilstein Registry No. 8789325; Molecules; 2001; Bd. 6; Nr. 3; pp. 267-278; XP002466840.

Shoeb et al.; Beilstein Registry No. 2664221; Indian J. Chem.; 1965; Bd. 3; pp. 507; XP002466841.

Sen et al.; Beilstein Registry No. 2674860; J. Indian Chem. Soc.; 1965; Bd. 42; pp. 145-146; XP002466842.

Sen et al.; Beilstein Registry No. 2709563; J. Indian Chem. Soc.; 1965; Bd. 42; pp. 145-146; XP002466843.

Sen et al.; Beilstein Registry No. 2709564; J. Indian Chem. Soc.; 1965; Bd. 42; pp. 145-146; XP002466844.

Sen et al.; Beilstein Registry No. 2710222; J. Indian Chem. Soc.; 1965; Bd. 42; pp. 145-146; XP002466845.

Sen et al.; Beilstein Registry No. 2956418; J. Indian Chem. Soc.; 1965; Bd. 42; pp. 145-146; XP002466846.

Sen et al.; Beilstein Registry No. 2955989; J. Indian Chem. Soc.; 1965; Bd. 42; pp. 145-146; XP002466847.

Morissette et al.; Dual antagonists of the bradykinin B1 and B2 receptors based on a postulated common pharmacophore from existing non-peptide antagonists; Biological Chemistry; 2006; vol. 387, No. 2; pp. 189-194.

Braichenko et al.; Investigations in the field of N-aryl-b-amino acids; Khimiko-Farmatsevicheskii Zhurnal; 1972; vol. 6, No. 8; pp. 6-8.

International Search Report, Form PCT/ISA/210, for corresponding PCT/EP2008/060562; date of mailing: Dec. 29, 2008.

COMPOUNDS

This application is a national phase entry under 35 U.S.C. 371 of international application PCT/EP2008/060562, filed Aug. 12, 2008, which claims priority to PCT/EP2007/058408, filed Aug. 14, 2007, PCT/EP2008/052157, filed Feb. 21, 2008 and EP08102043.0, filed Feb. 26, 2008, each of which is hereby incorporated by reference in its entirety.

The present invention relates to compounds of general formula I

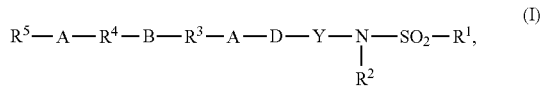

wherein A, B, D, Y, $R^1$, $R^2$, $R^3$, $R^4$ and $R^5$ are defined as in claim 1, the enantiomers, diastereomers, mixtures thereof and the salts thereof, particularly the physiologically acceptable salts thereof with organic or inorganic acids or bases, which have valuable properties, the preparation thereof, the pharmaceutical compositions containing the pharmacologically effective compounds, the preparation thereof and the use thereof.

DETAILED DESCRIPTION OF THE INVENTION

In the above general formula I in a first embodiment
A denotes a bond,
B denotes a bond,
D-Y together denote a group selected from

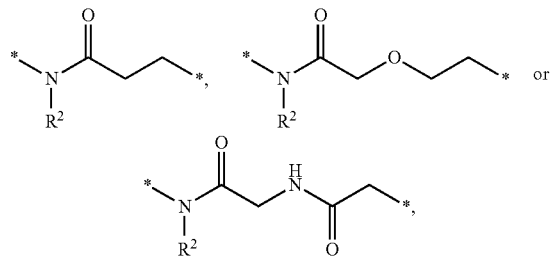

$R^1$ denotes the group

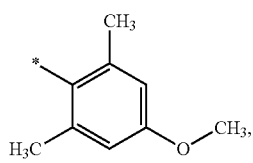

$R^2$ denotes H or $C_{1-3}$-alkyl, while each methylene group may be substituted by up to two fluorine atoms and each methyl group may be substituted by up to three fluorine atoms, or also $H_3C$—C(O),
$R^3$ denotes a $C_{4-6}$-cycloalkylene group which may be substituted by one, two or three $R^{3.1}$ groups,
$R^{3.1}$ denotes —$CH_3$, —$C_2H_5$, iso-propyl, tert-butyl, —OH, F, Cl, Br, I,
$R^4$ denotes a saturated 6- or 7-membered diaza heterocycle,
$R^5$ denotes $C_{1-3}$-alkyl or $C_{3-5}$-cycloalkyl,
the enantiomers, the diastereomers, the mixtures thereof and the salts thereof, particularly the physiologically acceptable salts thereof with organic or inorganic acids or bases.

A second embodiment of the present invention comprises the compounds of the above general formula I, wherein
A denotes a bond,
B denotes a bond,
D-Y together denote a group selected from

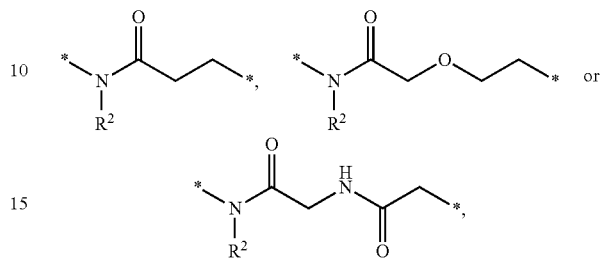

$R^1$ denotes the group

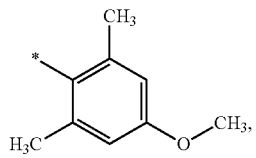

$R^2$ denotes H or $C_{1-3}$-alkyl, while each methylene group may be substituted by up to two fluorine atoms and each methyl group may be substituted by up to three fluorine atoms, or also $H_3C$—C(O),
$R^3$ denotes a $C_{4-6}$-cycloalkylene group,
$R^4$ denotes a saturated 6- or 7-membered diaza heterocycle,
$R^5$ denotes $C_{1-3}$-alkyl or $C_{3-5}$-cycloalkyl,
the enantiomers, the diastereomers, the mixtures thereof and the salts thereof, particularly the physiologically acceptable salts thereof with organic or inorganic acids or bases.

A third embodiment of the present invention comprises the compounds of the above general formula I, wherein A, B, D, Y, $R^1$, $R^2$, $R^4$ and $R^5$ are defined as hereinbefore in the first embodiment and
$R^3$ denotes a $C_{4-6}$-cycloalkylene group which may be substituted by one, two or three $R^{3.1}$ groups, and
$R^{3.1}$ denotes —$CH_3$, —$C_2H_5$, iso-propyl, tert-butyl, —OH, F, Cl, Br or I,
with the proviso that the above-mentioned $C_{4-6}$-cycloalkylene group is linked in the 1,3 position to the remainder of the molecule,
the enantiomers, the diastereomers, the mixtures thereof and the salts thereof, particularly the physiologically acceptable salts thereof with organic or inorganic acids or bases.

A fourth embodiment of the present invention comprises the compounds of the above general formula I, wherein A, B, D, Y, $R^1$, $R^2$, $R^4$ and $R^5$ are defined as hereinbefore in the second embodiment and
$R^3$ denotes a $C_{4-6}$-cycloalkylene group which may be substituted by one, two or three $R^{3.1}$ groups, and
$R^{3.1}$ denotes —$CH_3$, —$C_2H_5$, iso-propyl, tert-butyl, —OH, F, Cl, Br or I,
with the proviso that the above-mentioned $C_{4-6}$-cycloalkylene group is linked in the 1,3 position to the remainder of the molecule,
the enantiomers, the diastereomers, the mixtures thereof and the salts thereof, particularly the physiologically acceptable salts thereof with organic or inorganic acids or bases.

A fifth embodiment of the present invention comprises the compounds of the above general formula I, wherein
A denotes a bond,
B denotes a bond,
D-Y together denote a group selected from

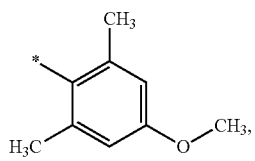 or

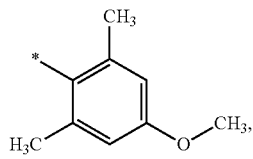

$R^1$ denotes the group

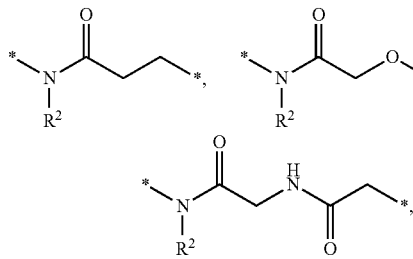

$R^2$ denotes H or $C_{1-3}$-alkyl, while each methylene group may be substituted by up to two and each methyl group may be substituted by up to three fluorine atoms, or also $H_3C-C(O)$,
$R^3$ denotes a $C_{4-6}$-cycloalkylene group which may be substituted by one, two or three $R^{3.1}$ groups,
$R^{3.1}$ denotes $-CH_3$, $-C_2H_5$, iso-propyl, tert-butyl, $-OH$, F, Cl,
$R^4$ denotes a saturated 6- or 7-membered diaza heterocycle,
$R^5$ denotes H, $C_{1-3}$-alkyl or $C_{3-5}$-cycloalkyl,
the enantiomers, the diastereomers, the mixtures thereof and the salts thereof, particularly the physiologically acceptable salts thereof with organic or inorganic acids or bases.

A sixth embodiment of the present invention comprises the compounds of the above general formula I, wherein
A denotes a bond,
B denotes a bond,
D-Y together denote a group selected from

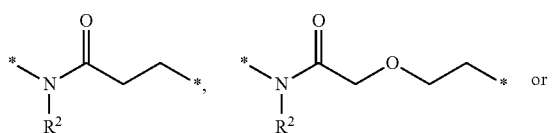

$R^1$ denotes the group

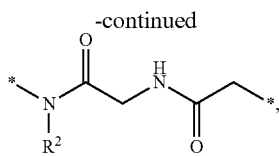

$R^2$ denotes H or $C_{1-3}$-alkyl, while each methylene group may be substituted by up to two and each methyl group may be substituted by up to three fluorine atoms, or also $H_3C-C(O)$,
$R^3$ denotes a $C_{4-6}$-cycloalkylene group,
$R^4$ denotes a saturated 6- or 7-membered diaza heterocycle,
$R^5$ denotes H, $C_{1-3}$-alkyl or $C_{3-5}$-cycloalkyl,
the enantiomers, the diastereomers, the mixtures thereof and the salts thereof, particularly the physiologically acceptable salts thereof with organic or inorganic acids or bases.

A seventh embodiment of the present invention comprises the compounds of the above general formula I, wherein A, B, D, Y, $R^1$, $R^2$, $R^4$ and $R^5$ are defined as hereinbefore in the fifth embodiment and
$R^3$ denotes a $C_{4-6}$-cycloalkylene group which may be substituted by one, two or three $R^{3.1}$ groups, and
$R^{3.1}$ denotes $-CH_3$, $-C_2H_5$, iso-propyl, tert-butyl, $-OH$, F or Cl,
with the proviso that the above-mentioned $C_{4-6}$-cycloalkylene group is linked in the 1,3 position to the remainder of the molecule,
the enantiomers, the diastereomers, the mixtures thereof and the salts thereof, particularly the physiologically acceptable salts thereof with organic or inorganic acids or bases.

An eighth embodiment of the present invention comprises the compounds of the above general formula I, wherein A, B, D, Y, $R^1$, $R^2$, $R^4$ and $R^5$ are defined as hereinbefore in the fifth embodiment and
$R^3$ denotes a $C_{4-6}$-cycloalkylene group which may be substituted by one, two or three $R^{3.1}$ groups, and
$R^{3.1}$ denotes $-CH_3$, $-C_2H_5$, iso-propyl, tert-butyl, $-OH$, F or Cl,
with the proviso that the above-mentioned $C_{4-6}$-cycloalkylene group is linked in the 1,3 position to the remainder of the molecule,
the enantiomers, the diastereomers, the mixtures thereof and the salts thereof, particularly the physiologically acceptable salts thereof with organic or inorganic acids or bases.

The following are mentioned as examples of particularly preferred compounds of the above general formula I:

| No. | Structure |
|---|---|
| (1) | 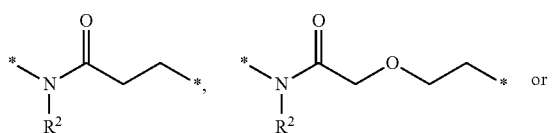 |

| No. | Structure |
|---|---|
| (2) | 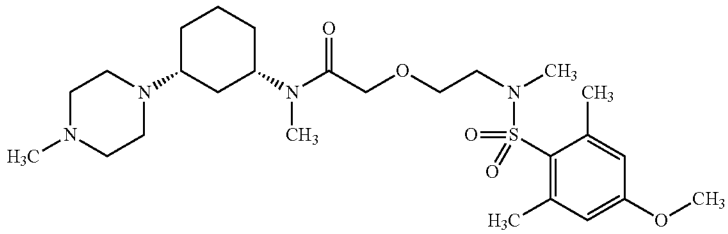 |
| (3) | 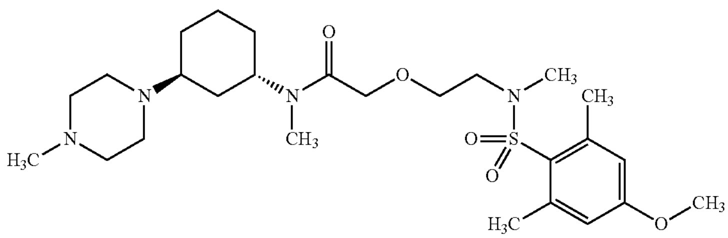 |
| (4) | 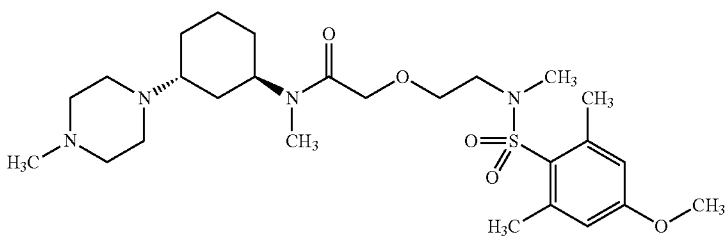 |
| (5) | 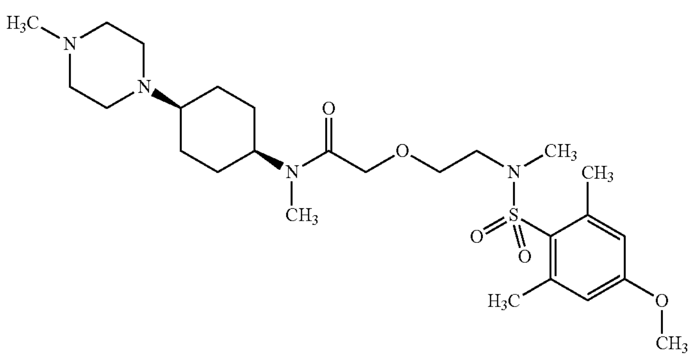 |
| (6) | 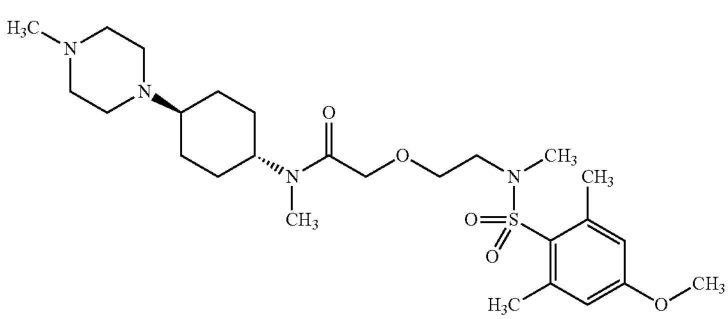 |

-continued
| No. | Structure |
|---|---|
| (7) | 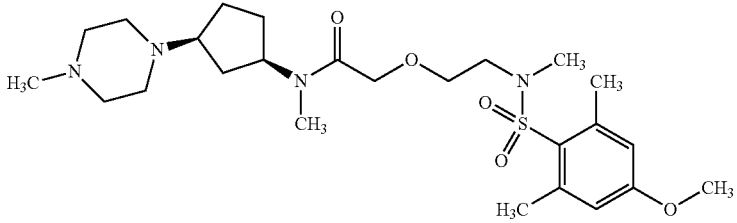 |
| (8) | 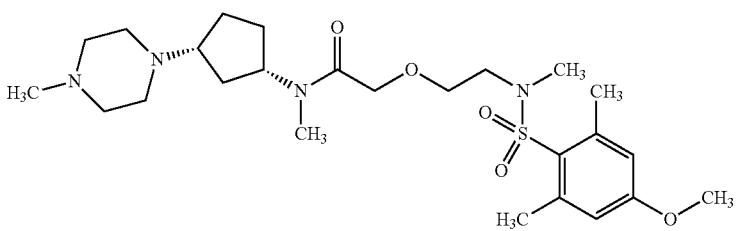 |
| (9) | 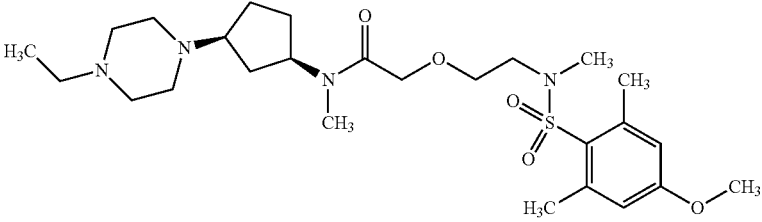 [SMILES: CCN1CCN([C@H]2CC[C@@H](N(C)C(=O)COCCN(C)S(=O)(=O)c3c(C)cc(OC)cc3C)C2)CC1] |
| (10) | 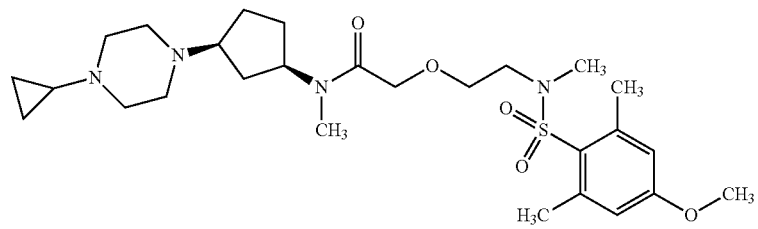 [SMILES: COc1cc(C)c(S(=O)(=O)N(C)CCOCC(=O)N(C)[C@@H]2CC[C@H](N3CCN(C4CC4)CC3)C2)c(C)c1] |
| (11) | 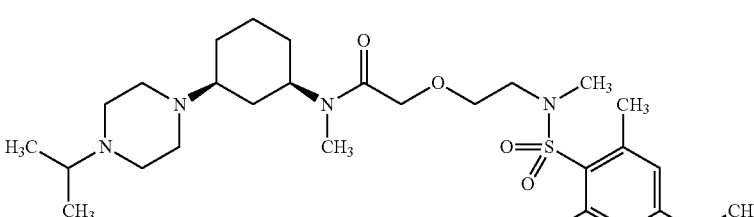 |
| (12) | 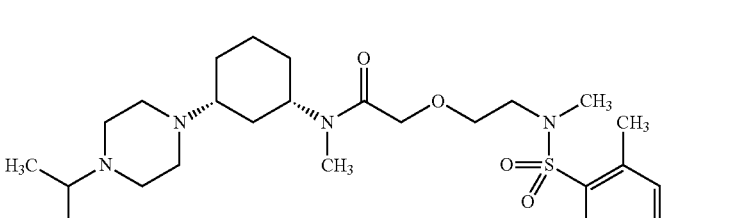 |

| No. | Structure |
|---|---|
| (13) | 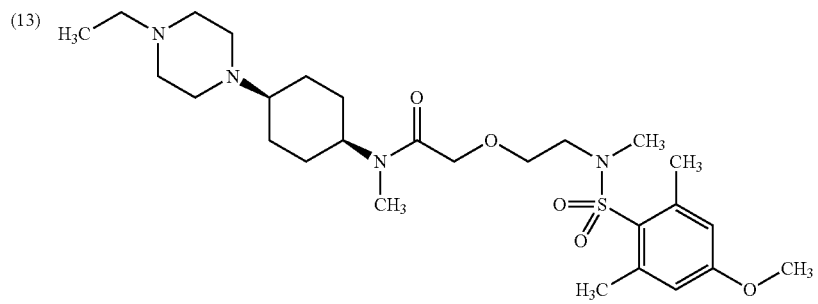 |
| (14) | 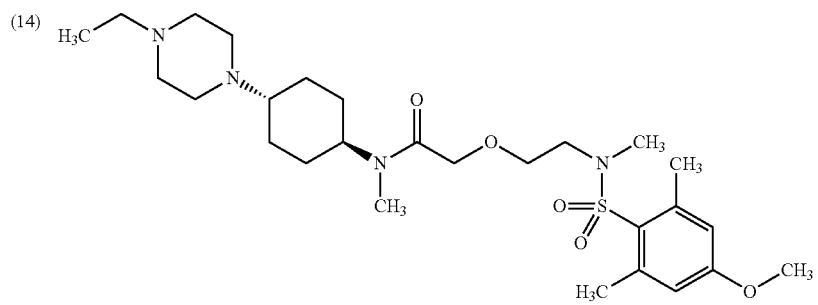 |
| (15) | 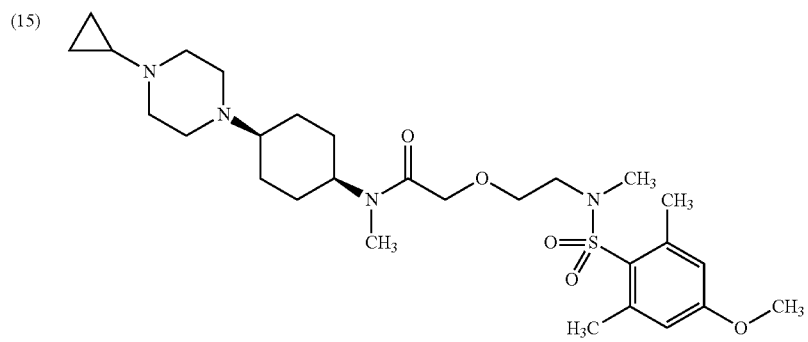 |
| (16) | 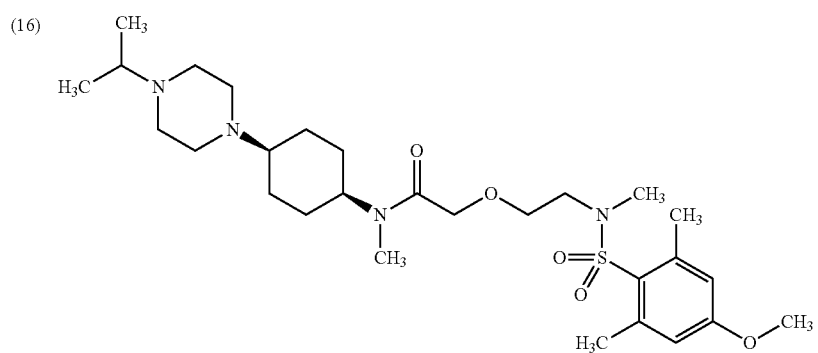 |

-continued

| No. | Structure |
|---|---|
| (17) | 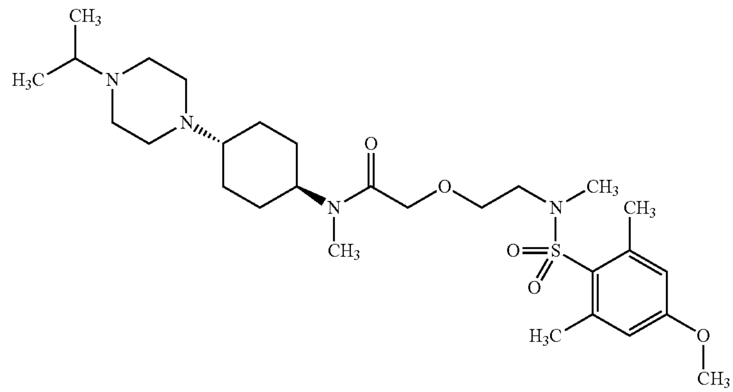 [SMILES: COc1cc(C)c(S(=O)(=O)N(C)CCOCC(=O)N(C)[C@H]2CC[C@H](N3CCN(C(C)C)CC3)CC2)c(C)c1] |
| (18) | 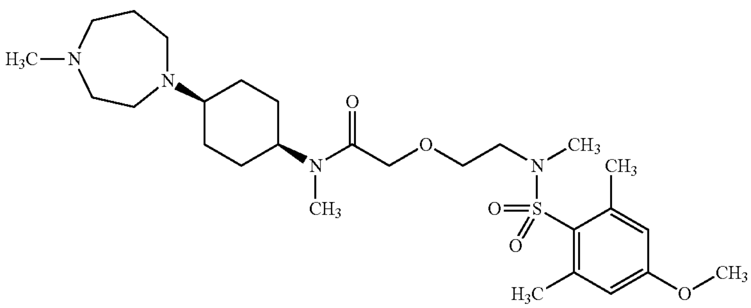 |
| (19) | 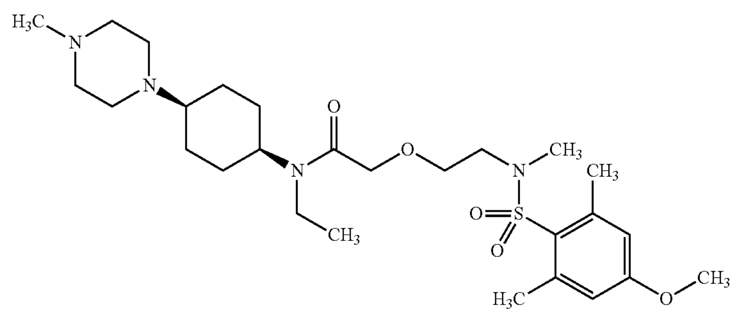 |
| (20) | 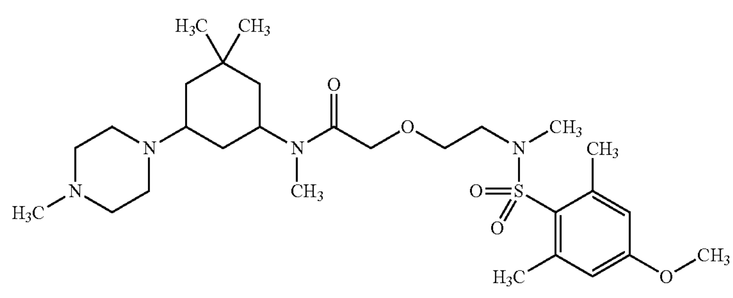 |
| (21) | 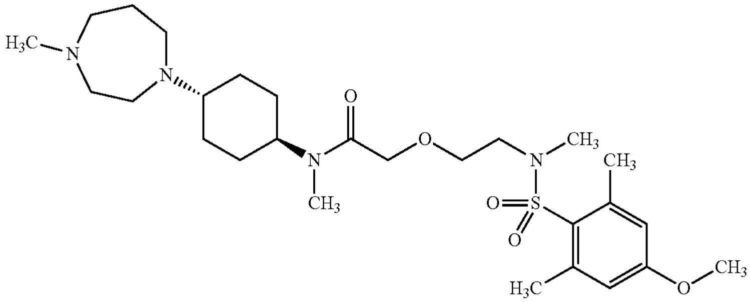 |

-continued
| No. | Structure |
|---|---|
| (22) | 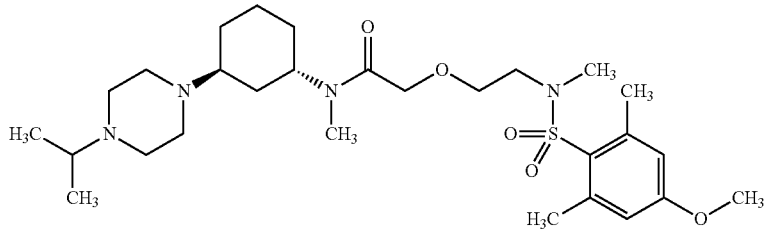 [SMILES: COc1cc(C)c(S(=O)(=O)N(C)CCOCC(=O)N(C)[C@H]2CCC[C@H](N3CCN(C(C)C)CC3)C2)c(C)c1] |
| (23) | 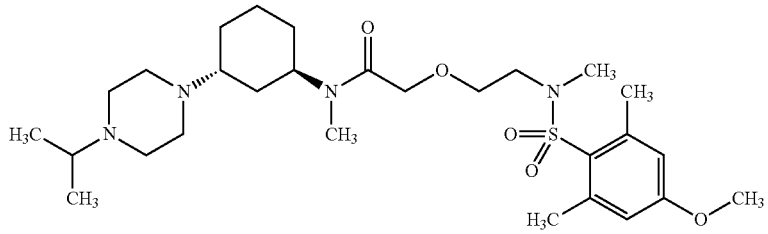 [SMILES: COc1cc(C)c(S(=O)(=O)N(C)CCOCC(=O)N(C)[C@@H]2CCC[C@@H](N3CCN(C(C)C)CC3)C2)c(C)c1] |
| (24) | 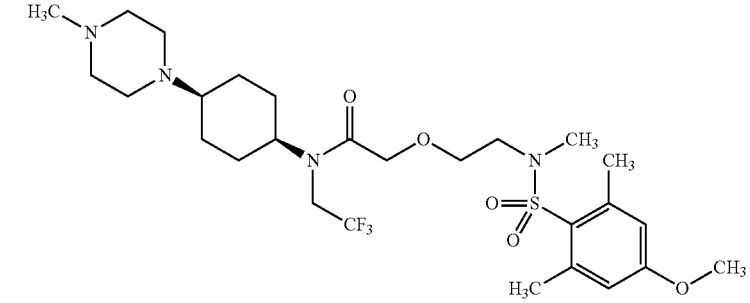 |
| (25) | 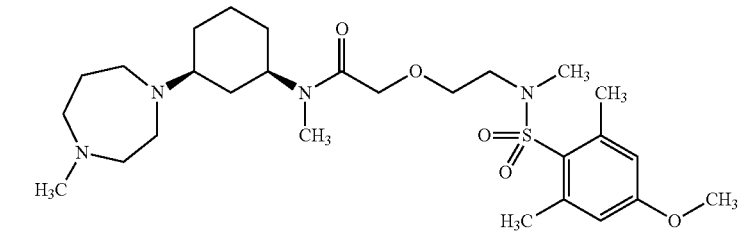 |
| (26) | 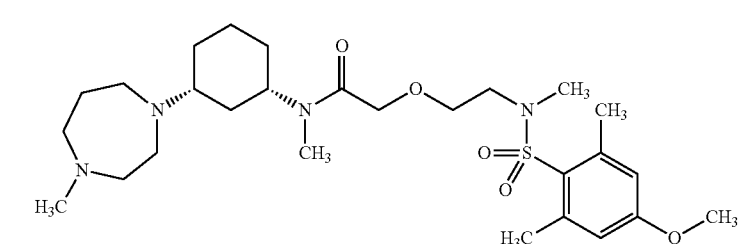 |
| (27) | 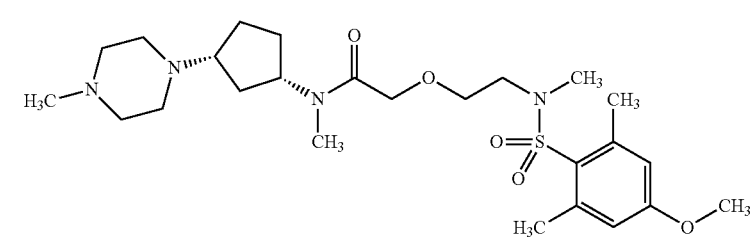 |

-continued
| No. | Structure |
|---|---|
| (28) | 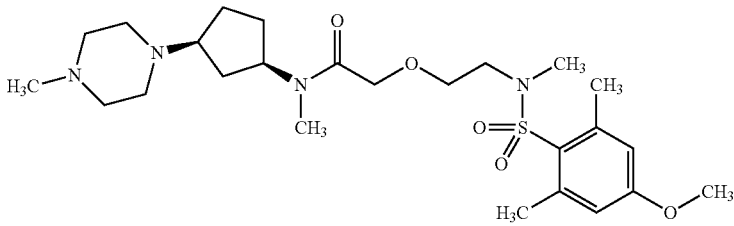 |
| (29) | 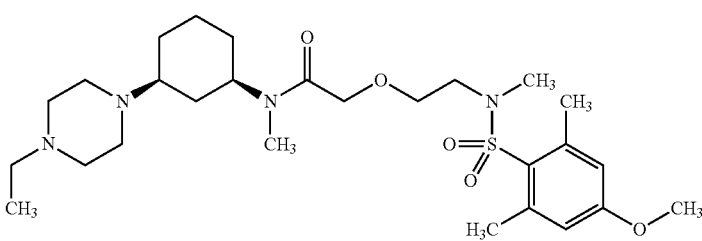 [SMILES: CCN1CCN([C@H]2CCC[C@@H](N(C)C(=O)COCCN(C)S(=O)(=O)c3c(C)cc(OC)cc3C)C2)CC1] |
| (30) | 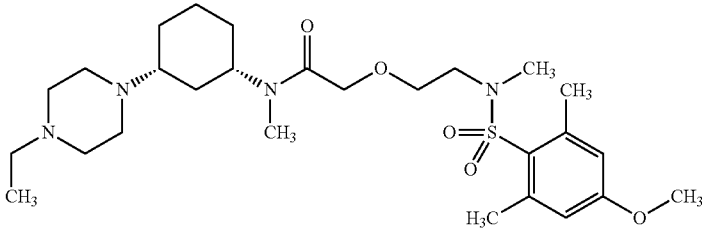 [SMILES: CCN1CCN([C@@H]2CCC[C@H](N(C)C(=O)COCCN(C)S(=O)(=O)c3c(C)cc(OC)cc3C)C2)CC1] |
| (31) | 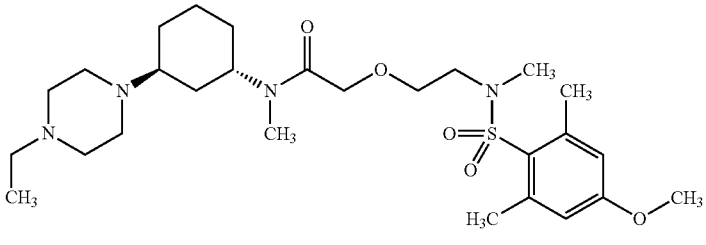 |
| (32) | 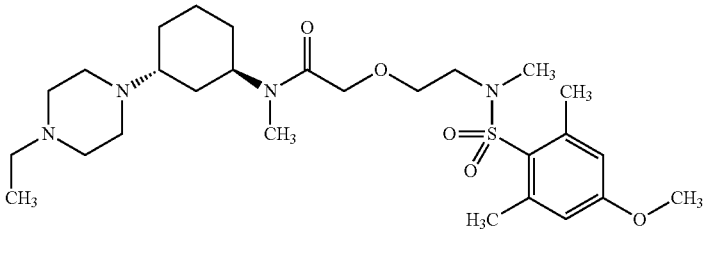 [SMILES: CCN1CCN([C@@H]2CCC[C@@H](N(C)C(=O)COCCN(C)S(=O)(=O)c3c(C)cc(OC)cc3C)C2)CC1] |
| (33) | 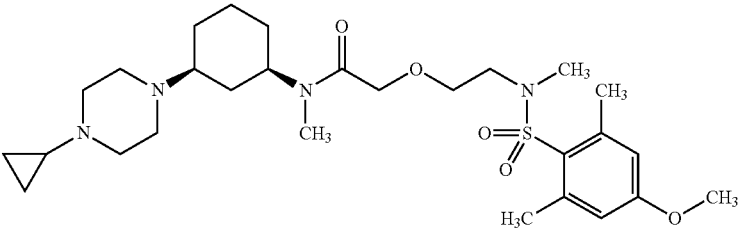 [SMILES: COc1cc(C)c(S(=O)(=O)N(C)CCOCC(=O)N(C)[C@@H]2CCC[C@H](N3CCN(C4CC4)CC3)C2)c(C)c1] |

| No. | Structure |
|---|---|
| (34) | 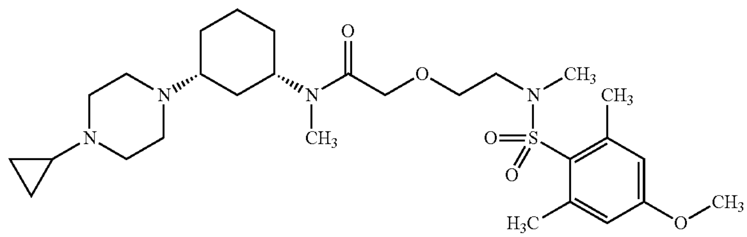 [SMILES: COc1cc(C)c(S(=O)(=O)N(C)CCOCC(=O)N(C)[C@H]2CCC[C@@H](N3CCN(C4CC4)CC3)C2)c(C)c1] |
| (35) | 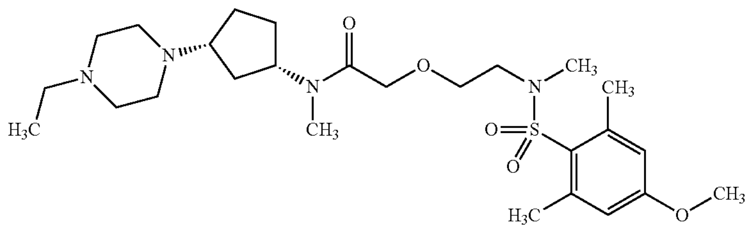 |
| (36) | 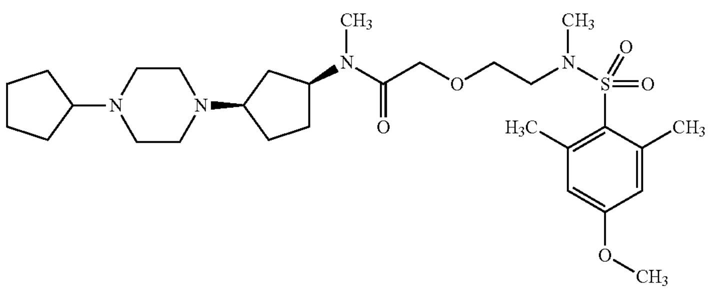 [SMILES: COc1cc(C)c(S(=O)(=O)N(C)CCOCC(=O)N(C)[C@H]2CC[C@@H](N3CCN(C4CCCC4)CC3)C2)c(C)c1] |
| (37) | 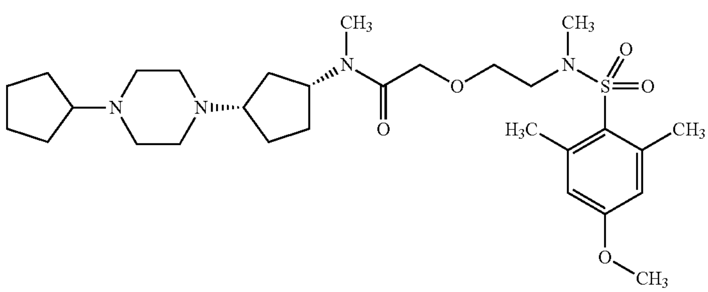 [SMILES: COc1cc(C)c(S(=O)(=O)N(C)CCOCC(=O)N(C)[C@@H]2CC[C@H](N3CCN(C4CCCC4)CC3)C2)c(C)c1] |
| (38) | 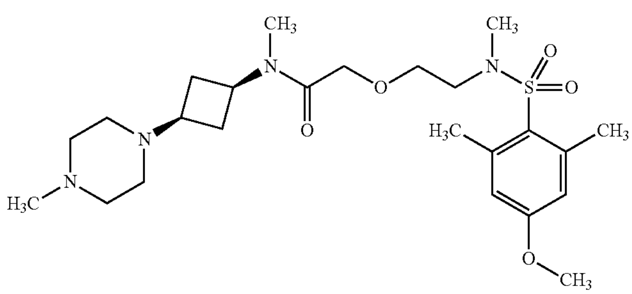 |
| (39) | 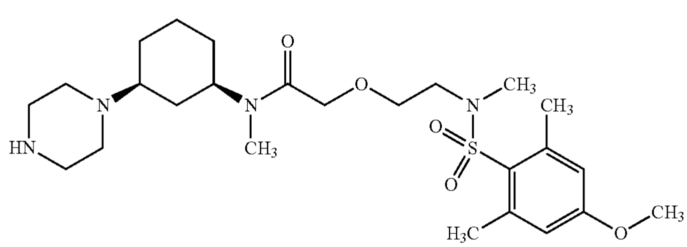 [SMILES: COc1cc(C)c(S(=O)(=O)N(C)CCOCC(=O)N(C)[C@@H]2CCC[C@H](N3CCNCC3)C2)c(C)c1] |

| No. | Structure |
|---|---|
| (40) | 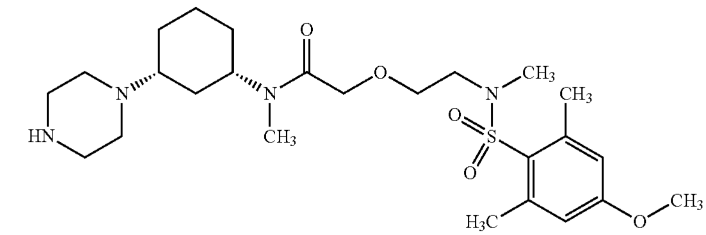 [SMILES: COc1cc(C)c(S(=O)(=O)N(C)CCOCC(=O)N(C)[C@H]2CCC[C@@H](N3CCNCC3)C2)c(C)c1] |
| (41) | 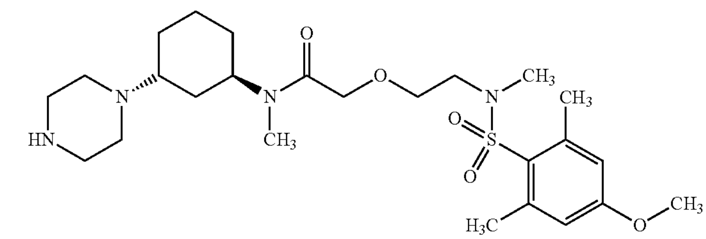 |
| (42) | 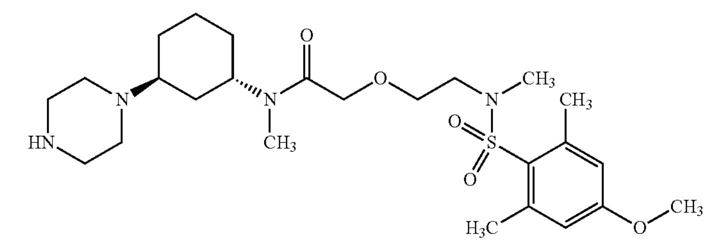 [SMILES: COc1cc(C)c(S(=O)(=O)N(C)CCOCC(=O)N(C)[C@H]2CCC[C@H](N3CCNCC3)C2)c(C)c1] |
| (43) | | the enantiomers, the diastereomers, the mixtures thereof and the salts thereof, particularly the physiologically acceptable salts thereof with organic or inorganic acids or bases.

The following are mentioned as examples of most particularly preferred compounds of the above general formula I:

| No. | Structure |
|---|---|
| (1) | 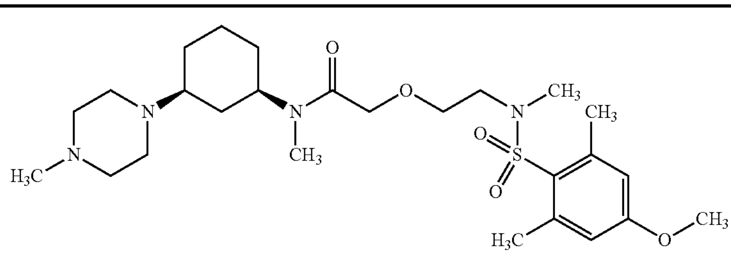 |

-continued

| No. | Structure |
|---|---|
| (2) | 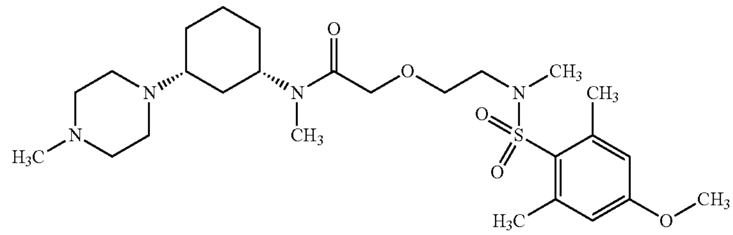 |
| (3) | 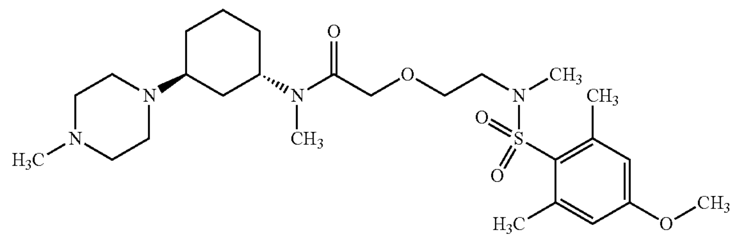 |
| (4) | 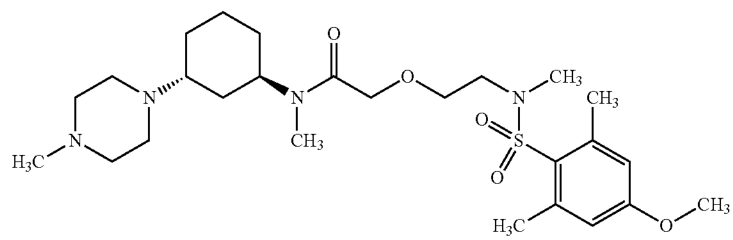 |
| (5) | 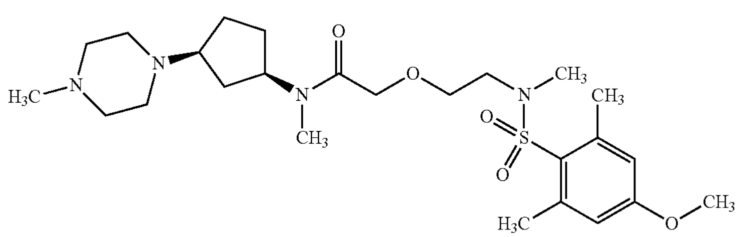 |
| (6) | 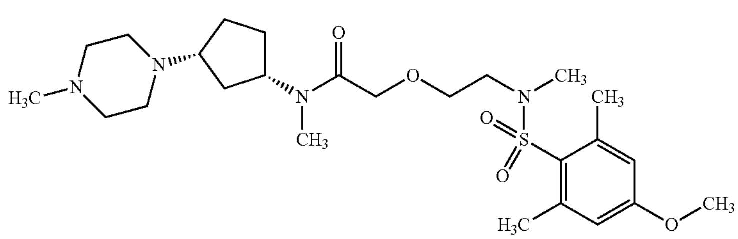 |
| (7) | 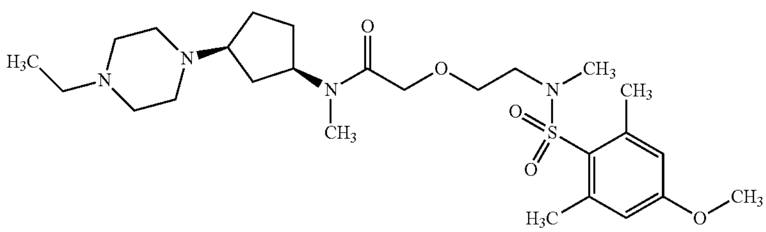 [SMILES: CCN1CCN([C@H]2CC[C@@H](N(C)C(=O)COCCN(C)S(=O)(=O)c3c(C)cc(OC)cc3C)C2)CC1] |

| No. | Structure |
|---|---|
| (8) | 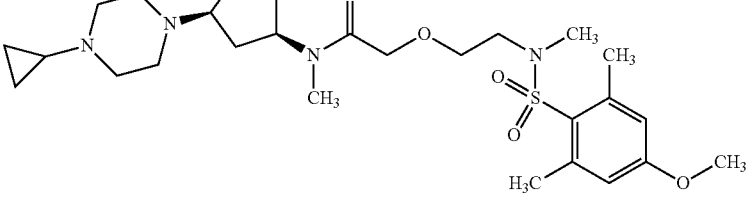 |
| (9) | 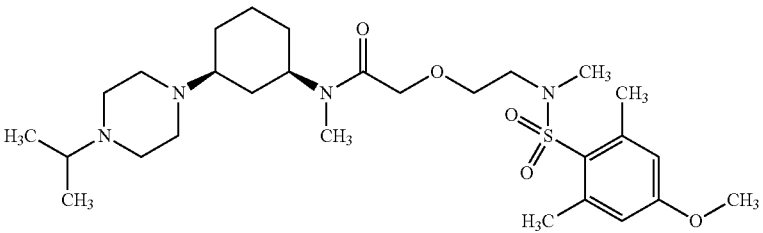 [SMILES: COc1cc(C)c(S(=O)(=O)N(C)CCOCC(=O)N(C)[C@@H]2CCC[C@H](N3CCN(C(C)C)CC3)C2)c(C)c1] |
| (10) | 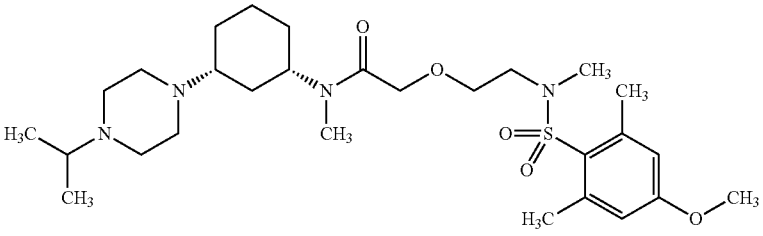 [SMILES: COc1cc(C)c(S(=O)(=O)N(C)CCOCC(=O)N(C)[C@H]2CCC[C@@H](N3CCN(C(C)C)CC3)C2)c(C)c1] |
| (11) | 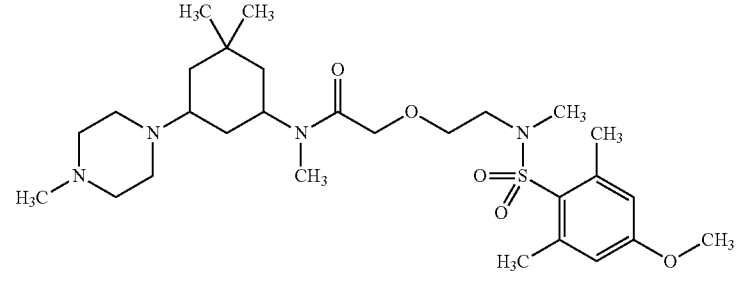 |
| (12) | 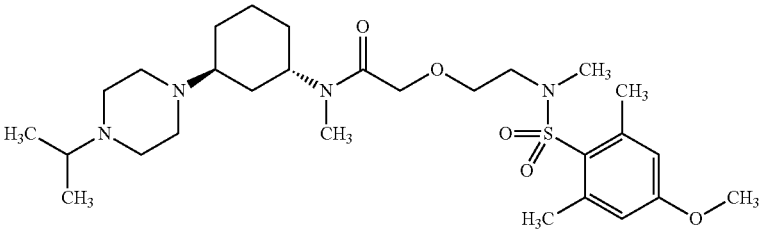 [SMILES: COc1cc(C)c(S(=O)(=O)N(C)CCOCC(=O)N(C)[C@H]2CCC[C@H](N3CCN(C(C)C)CC3)C2)c(C)c1] |
| (13) | 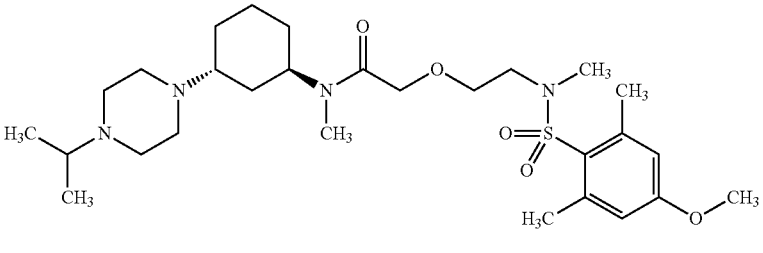 [SMILES: COc1cc(C)c(S(=O)(=O)N(C)CCOCC(=O)N(C)[C@@H]2CCC[C@@H](N3CCN(C(C)C)CC3)C2)c(C)c1] |

-continued
| No. | Structure |
|---|---|
| (14) | 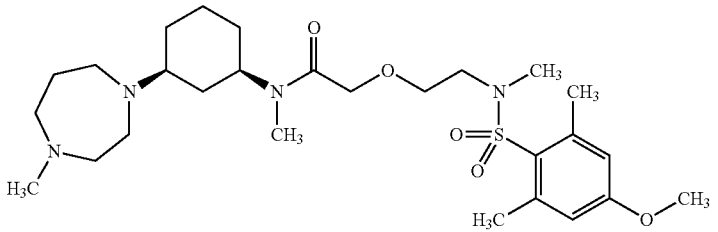 |
| (15) | 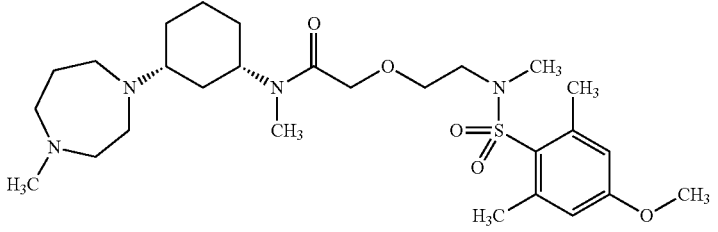 |
| (16) | 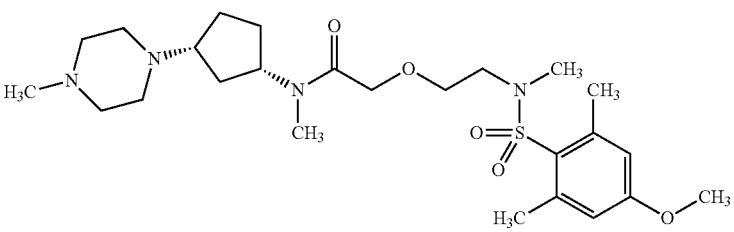 |
| (17) | 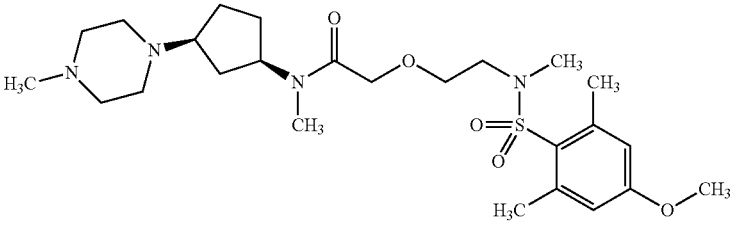 |
| (18) | 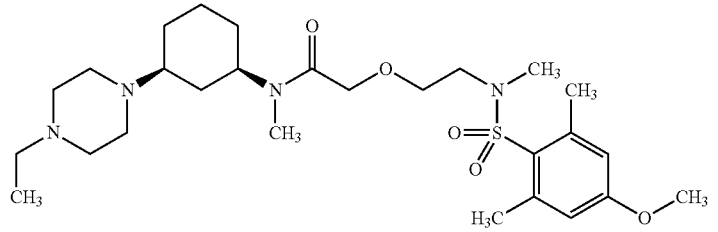 [SMILES: CCN1CCN([C@H]2CCC[C@@H](N(C)C(=O)COCCN(C)S(=O)(=O)c3c(C)cc(OC)cc3C)C2)CC1] |
| (19) | 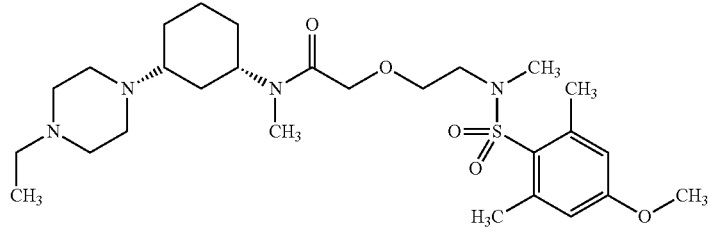 |

-continued

| No. | Structure |
|---|---|
| (20) | 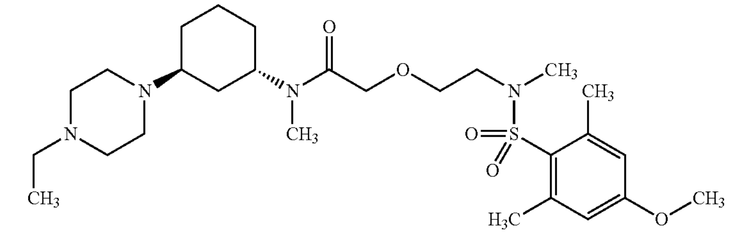 [SMILES: CCN1CCN([C@H]2CCC[C@H](N(C)C(=O)COCCN(C)S(=O)(=O)c3c(C)cc(OC)cc3C)C2)CC1] |
| (21) | 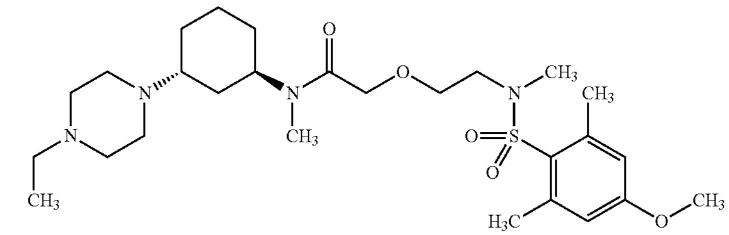 [SMILES: CCN1CCN([C@@H]2CCC[C@@H](N(C)C(=O)COCCN(C)S(=O)(=O)c3c(C)cc(OC)cc3C)C2)CC1] |
| (22) | 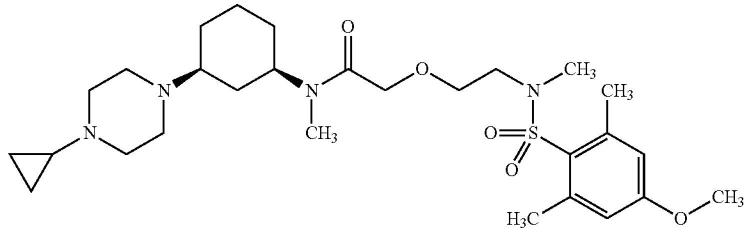 [SMILES: COc1cc(C)c(S(=O)(=O)N(C)CCOCC(=O)N(C)[C@@H]2CCC[C@H](N3CCN(C4CC4)CC3)C2)c(C)c1] |
| (23) | 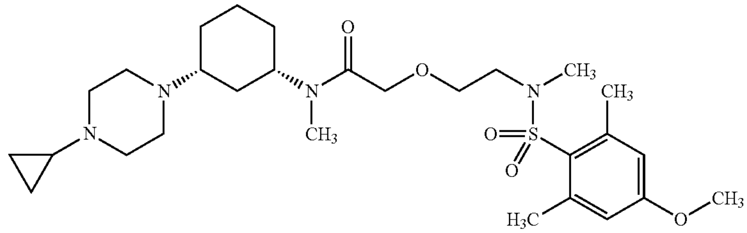 [SMILES: COc1cc(C)c(S(=O)(=O)N(C)CCOCC(=O)N(C)[C@H]2CCC[C@@H](N3CCN(C4CC4)CC3)C2)c(C)c1] |
| (24) | 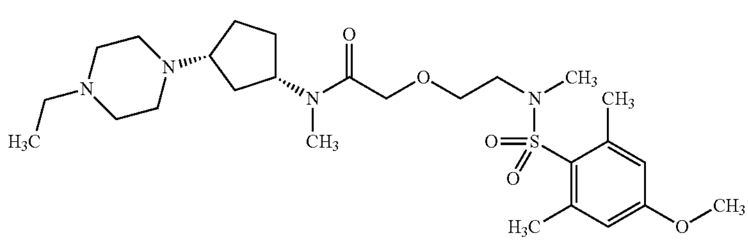 [SMILES: CCN1CCN([C@@H]2CC[C@H](N(C)C(=O)COCCN(C)S(=O)(=O)c3c(C)cc(OC)cc3C)C2)CC1] |
| (25) | 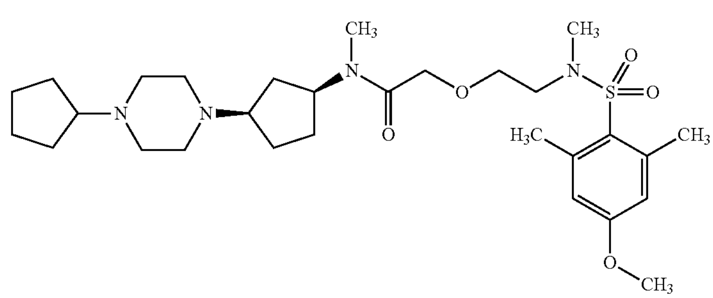 [SMILES: COc1cc(C)c(S(=O)(=O)N(C)CCOCC(=O)N(C)[C@H]2CC[C@@H](N3CCN(C4CCCC4)CC3)C2)c(C)c1] |

-continued

| No. | Structure |
|---|---|
| (26) | 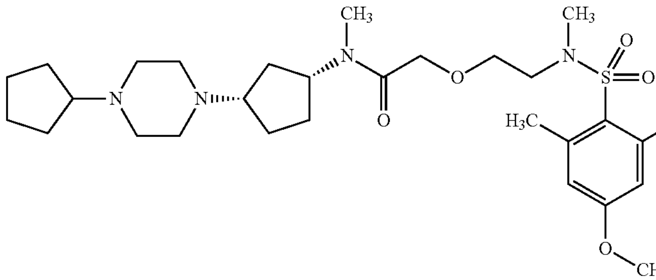 |
| (27) | 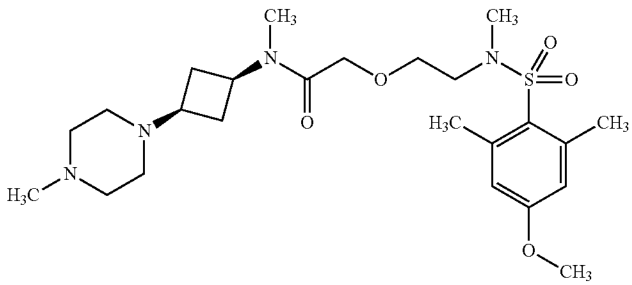 |
| (28) | 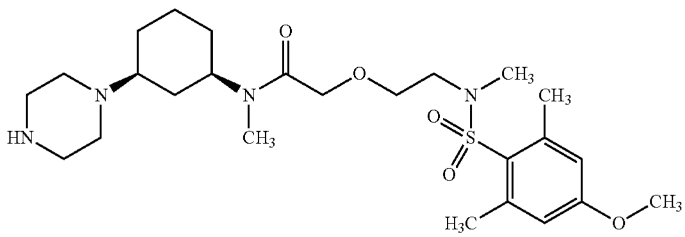 [SMILES: COc1cc(C)c(S(=O)(=O)N(C)CCOCC(=O)N(C)[C@@H]2CCC[C@H](N3CCNCC3)C2)c(C)c1] |
| (29) | 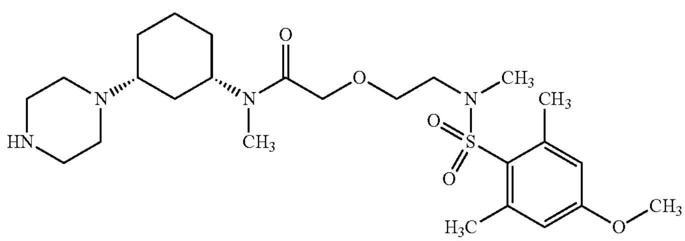 [SMILES: COc1cc(C)c(S(=O)(=O)N(C)CCOCC(=O)N(C)[C@H]2CCC[C@@H](N3CCNCC3)C2)c(C)c1] |
| (30) | 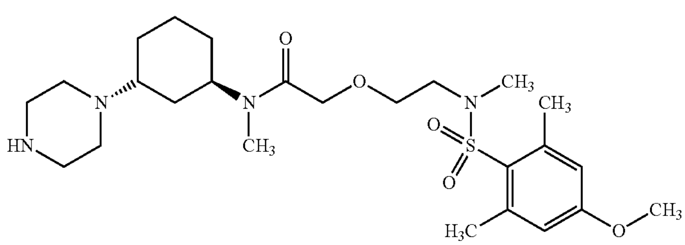 |
| (31) | | the enantiomers, the diastereomers, the mixtures thereof and the salts thereof, particularly the physiologically acceptable salts thereof with organic or inorganic acids or bases.

In another aspect the present invention relates to the compounds of general formula Ia

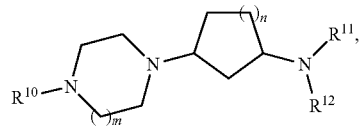
(Ia)

wherein
m denotes one of the numbers 1 or 2,
n denotes one of the numbers 0, 1 or 2,
$R^{10}$ denotes H, $C_{1-4}$-alkyl, $C_{3-6}$-cycloalkyl, $C_{1-4}$-alkyl-O—C(O), benzyl-O—C(O) or benzyl, and
$R^{11}$, $R^{12}$ independently of one another denote
  (a) H,
  (b) $C_{1-4}$-alkyl, $C_{3-6}$-cycloalkyl,
  (c) benzyl,
  (d) $C_{1-4}$-alkyl-O—C(O) or benzyl-O—C(O)—,
the enantiomers, the diastereomers and the salts thereof, preferably the hydrochlorides thereof, which are particularly suitable for preparing compounds of general formula I.

The intermediate compounds of general formula Ia may be prepared analogously to the methods described in International Patent Application No. PCT/EP2007/058408 and optionally separated into their diastereomers or enantiomers using known methods.

In another preferred aspect the present invention relates to the compounds of general formula Ia, wherein
m denotes one of the numbers 1 or 2,
n denotes one of the numbers 0, 1 or 2,
$R^{10}$ denotes H, $C_{1-4}$-alkyl, $C_{3-6}$-cycloalkyl, $C_{1-4}$-alkyl-O—C(O), benzyl-O—C(O) or benzyl, and
$R^{11}$ denotes
  (a) H,
  (b) benzyl,
  (c) $C_{1-4}$-alkyl-O—C(O) or benzyl-O—C(O), and
$R^{12}$ denotes
  (a) H,
  (b) $C_{1-4}$-alkyl, $C_{3-6}$-cycloalkyl,
  (c) benzyl,
  (d) $C_{1-4}$-alkyl-O—C(O) or benzyl-O—C(O)—,
the enantiomers, the diastereomers and the salts thereof, preferably the hydrochlorides thereof.

The compounds of general formula Ia are valuable starting materials for synthesising the compounds of general formula I which have B1-antagonistic properties.

The following are mentioned, for example, as more preferred compounds of general formula Ia:

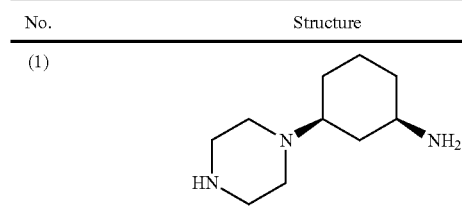

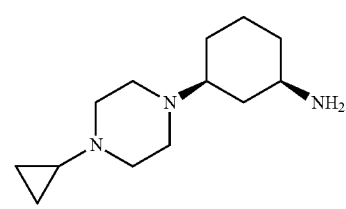

| No. | Structure |
|---|---|
| (10) | [cyclohexane with cyclopropyl-piperazine and NH2] |
| (11) | [cyclohexane with cyclopropyl-piperazine and NH2] |
| (12) | [cyclohexane with cyclopropyl-piperazine and NH2] |
| (13) | [cyclohexane with piperazine (HN) and NHCH3] |
| (14) | [cyclohexane with piperazine (HN) and NHCH3] |
| (15) | [cyclohexane with piperazine (HN) and NHCH3] |
| (16) | [cyclohexane with piperazine (HN) and NHCH3] |
| (17) | [cyclohexane with N-methylpiperazine and NHCH3] |
| (18) | [cyclohexane with N-methylpiperazine and NHCH3] |
| (19) | [cyclohexane with N-methylpiperazine and NHCH3] |
| (20) | [cyclohexane with N-methylpiperazine and NHCH3] |
| (21) | [cyclohexane with N-ethylpiperazine and NHCH3] |
| (22) | [cyclohexane with N-ethylpiperazine and NHCH3] |
| (23) | [cyclohexane with N-ethylpiperazine and NHCH3] |
| (24) | [cyclohexane with N-ethylpiperazine and NHCH3] |
| (25) | [cyclohexane with N-isopropylpiperazine and NHCH3] |

| No. | Structure |
|---|---|
| (26) | 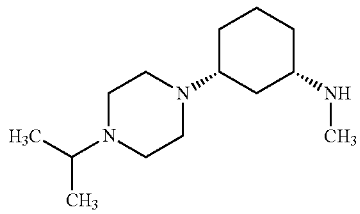 [SMILES: CN[C@H]1CCC[C@@H](N2CCN(C(C)C)CC2)C1] |
| (27) | 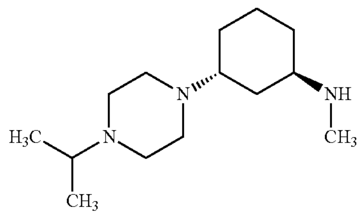 [SMILES: CN[C@@H]1CCC[C@@H](N2CCN(C(C)C)CC2)C1] |
| (28) | 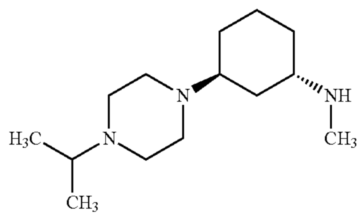 [SMILES: CN[C@H]1CCC[C@H](N2CCN(C(C)C)CC2)C1] |
| (29) | 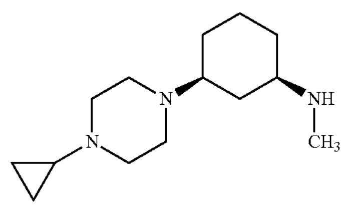 [SMILES: CN[C@@H]1CCC[C@H](N2CCN(C3CC3)CC2)C1] |
| (30) | 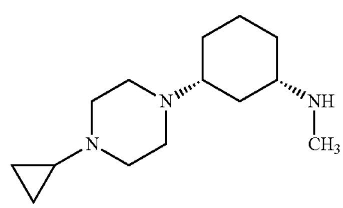 [SMILES: CN[C@H]1CCC[C@@H](N2CCN(C3CC3)CC2)C1] |
| (31) | 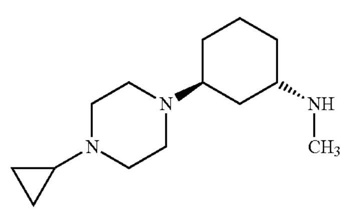 |
| (32) | 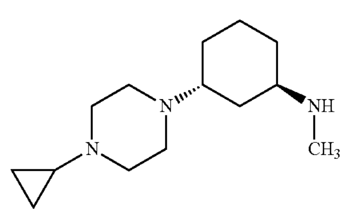 [SMILES: CN[C@@H]1CCC[C@@H](N2CCN(C3CC3)CC2)C1] |

| No. | Structure |
|---|---|
| (33) | 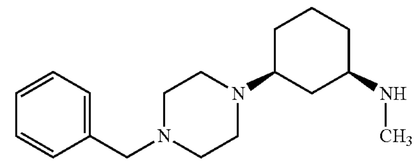 [SMILES: CN[C@@H]1CCC[C@H](N2CCN(Cc3ccccc3)CC2)C1] |
| (34) | 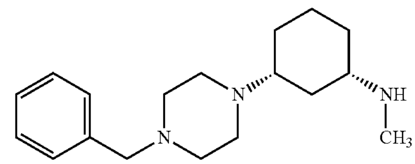 [SMILES: CN[C@H]1CCC[C@@H](N2CCN(Cc3ccccc3)CC2)C1] |
| (35) | 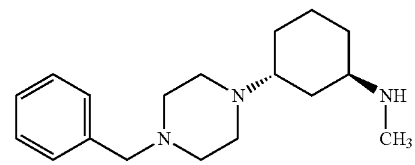 [SMILES: CN[C@@H]1CCC[C@@H](N2CCN(Cc3ccccc3)CC2)C1] |
| (36) | 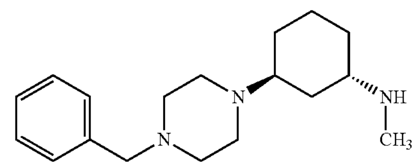 [SMILES: CN[C@H]1CCC[C@H](N2CCN(Cc3ccccc3)CC2)C1] |
| (37) | 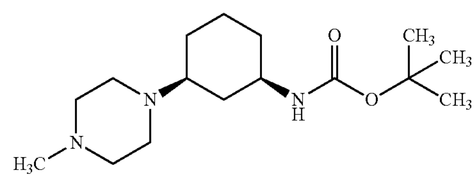 [SMILES: CN1CCN([C@H]2CCC[C@@H](NC(=O)OC(C)(C)C)C2)CC1] |
| (38) | 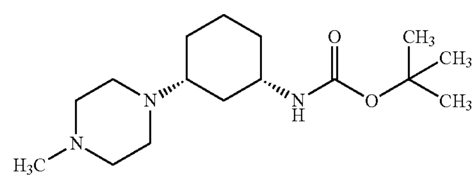 [SMILES: CN1CCN([C@@H]2CCC[C@H](NC(=O)OC(C)(C)C)C2)CC1] |
| (39) | 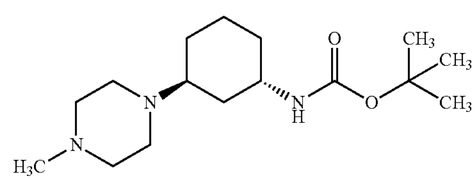 [SMILES: CN1CCN([C@H]2CCC[C@H](NC(=O)OC(C)(C)C)C2)CC1] |
| (40) | 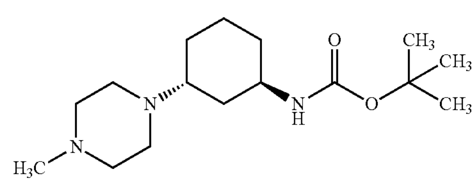 [SMILES: CN1CCN([C@@H]2CCC[C@@H](NC(=O)OC(C)(C)C)C2)CC1] |
| (41) | 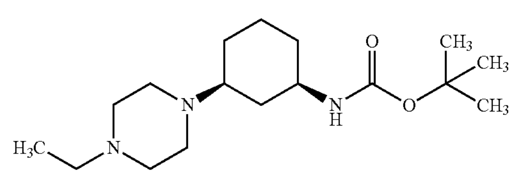 [SMILES: CCN1CCN([C@H]2CCC[C@@H](NC(=O)OC(C)(C)C)C2)CC1] |

| No. | Structure |
|---|---|
| (42) | 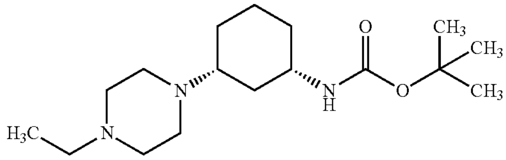 [SMILES: CCN1CCN([C@@H]2CCC[C@H](NC(=O)OC(C)(C)C)C2)CC1] |
| (43) | 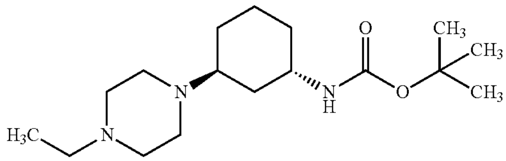 [SMILES: CCN1CCN([C@H]2CCC[C@H](NC(=O)OC(C)(C)C)C2)CC1] |
| (44) | 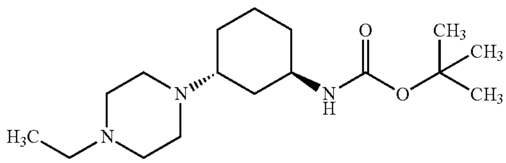 [SMILES: CCN1CCN([C@@H]2CCC[C@@H](NC(=O)OC(C)(C)C)C2)CC1] |
| (45) | 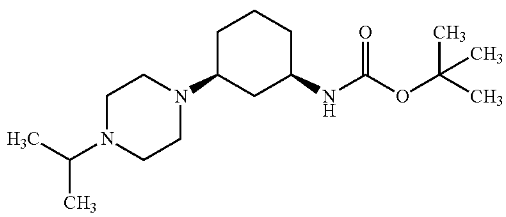 [SMILES: CC(C)N1CCN([C@H]2CCC[C@@H](NC(=O)OC(C)(C)C)C2)CC1] |
| (46) | 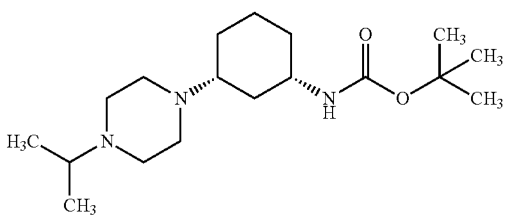 [SMILES: CC(C)N1CCN([C@@H]2CCC[C@H](NC(=O)OC(C)(C)C)C2)CC1] |
| (47) | 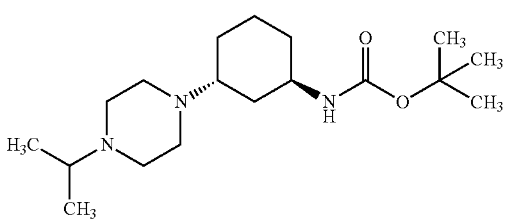 [SMILES: CC(C)N1CCN([C@@H]2CCC[C@@H](NC(=O)OC(C)(C)C)C2)CC1] |
| (48) | 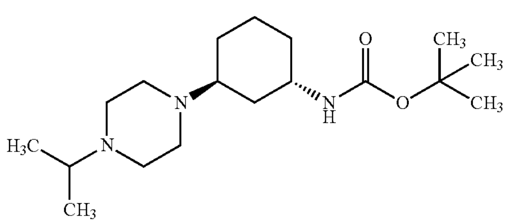 [SMILES: CC(C)N1CCN([C@H]2CCC[C@H](NC(=O)OC(C)(C)C)C2)CC1] |

| No. | Structure |
|---|---|
| (49) | 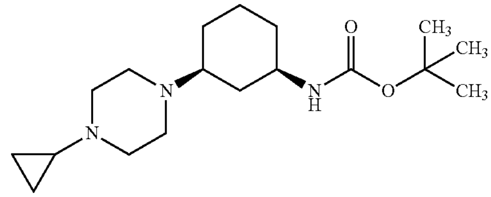 [SMILES: CC(C)(C)OC(=O)N[C@@H]1CCC[C@H](N2CCN(C3CC3)CC2)C1] |
| (50) | 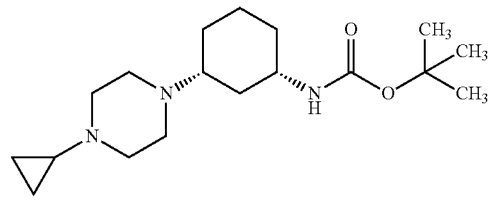 [SMILES: CC(C)(C)OC(=O)N[C@H]1CCC[C@@H](N2CCN(C3CC3)CC2)C1] |
| (51) | 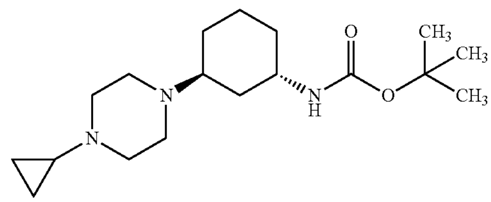 [SMILES: CC(C)(C)OC(=O)N[C@H]1CCC[C@H](N2CCN(C3CC3)CC2)C1] |
| (52) | 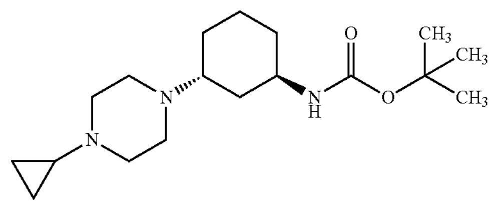 [SMILES: CC(C)(C)OC(=O)N[C@@H]1CCC[C@@H](N2CCN(C3CC3)CC2)C1] |
| (53) | 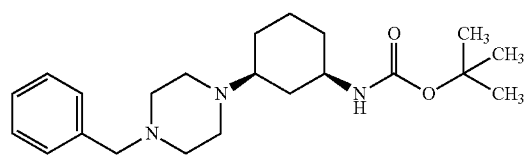 [SMILES: CC(C)(C)OC(=O)N[C@@H]1CCC[C@H](N2CCN(Cc3ccccc3)CC2)C1] |
| (54) | 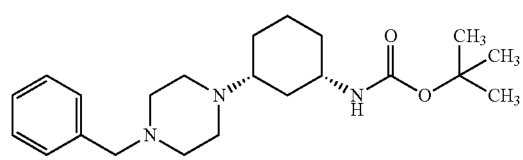 [SMILES: CC(C)(C)OC(=O)N[C@H]1CCC[C@@H](N2CCN(Cc3ccccc3)CC2)C1] |
| (55) | 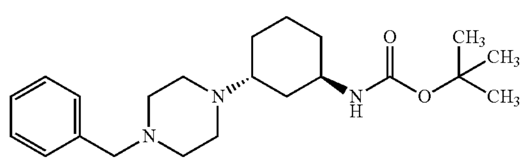 [SMILES: CC(C)(C)OC(=O)N[C@@H]1CCC[C@@H](N2CCN(Cc3ccccc3)CC2)C1] |
| (56) | 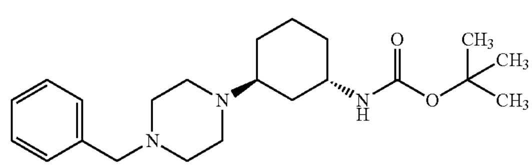 [SMILES: CC(C)(C)OC(=O)N[C@H]1CCC[C@H](N2CCN(Cc3ccccc3)CC2)C1] |

| No. | Structure |
|-----|-----------|
| (57) | 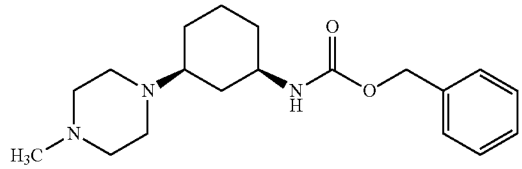 [SMILES: CN1CCN([C@H]2CCC[C@@H](NC(=O)OCc3ccccc3)C2)CC1] |
| (58) | 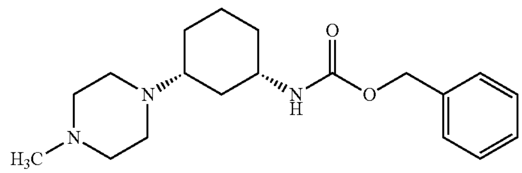 [SMILES: CN1CCN([C@@H]2CCC[C@H](NC(=O)OCc3ccccc3)C2)CC1] |
| (59) | 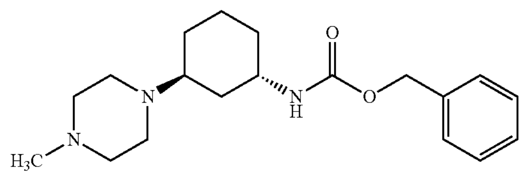 [SMILES: CN1CCN([C@H]2CCC[C@H](NC(=O)OCc3ccccc3)C2)CC1] |
| (60) | 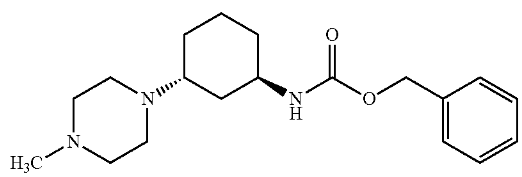 [SMILES: CN1CCN([C@@H]2CCC[C@@H](NC(=O)OCc3ccccc3)C2)CC1] |
| (61) | 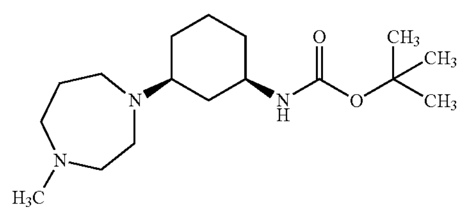 [SMILES: CN1CCCN([C@H]2CCC[C@@H](NC(=O)OC(C)(C)C)C2)CC1] |
| (62) | 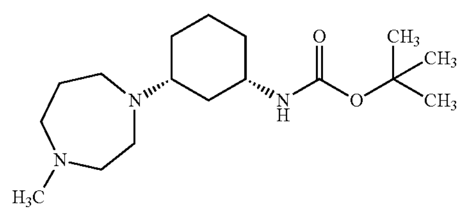 [SMILES: CN1CCCN([C@@H]2CCC[C@H](NC(=O)OC(C)(C)C)C2)CC1] |
| (63) | 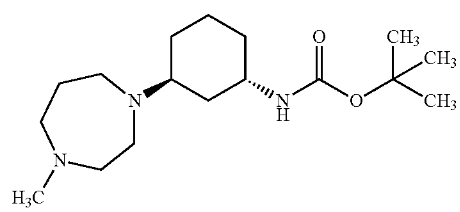 [SMILES: CN1CCCN([C@H]2CCC[C@H](NC(=O)OC(C)(C)C)C2)CC1] |
| (64) | 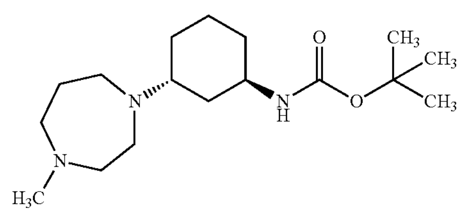 [SMILES: CN1CCCN([C@@H]2CCC[C@@H](NC(=O)OC(C)(C)C)C2)CC1] |

| No. | Structure |
|-----|-----------|
| (65) | 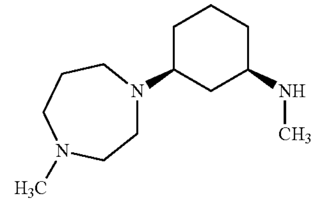 |
| (66) | 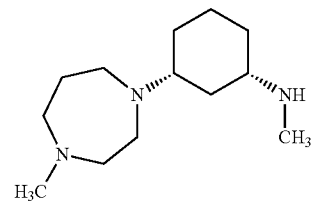 |
| (67) | 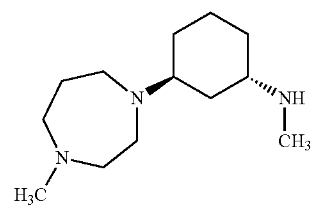 |
| (68) | 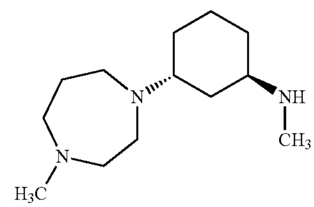 |
| (69) | 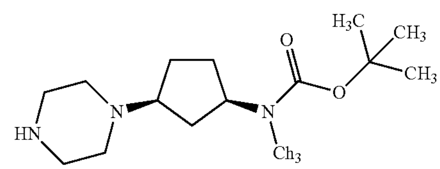 |
| (70) | 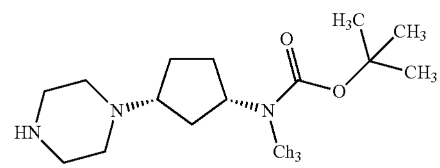 |
| (71) | 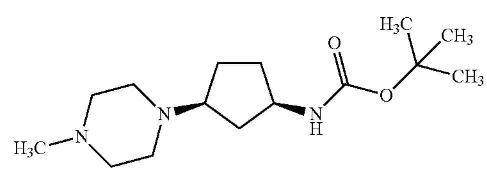 [SMILES: CN1CCN([C@H]2CC[C@@H](NC(=O)OC(C)(C)C)C2)CC1] |
| (72) | 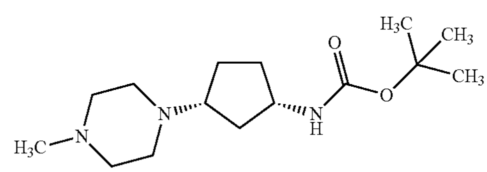 [SMILES: CN1CCN([C@@H]2CC[C@H](NC(=O)OC(C)(C)C)C2)CC1] |

| No. | Structure |
|---|---|
| (73) | 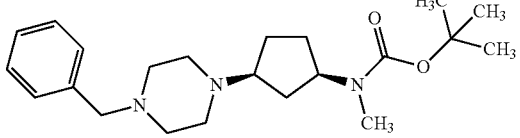 |
| (74) | 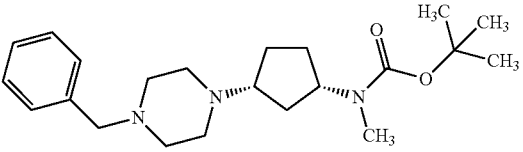 [SMILES: CN(C(=O)OC(C)(C)C)[C@H]1CC[C@@H](N2CCN(Cc3ccccc3)CC2)C1] |
| (75) | 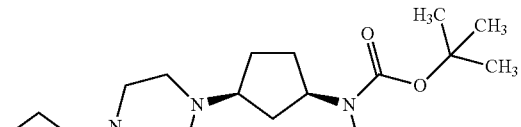 |
| (76) | 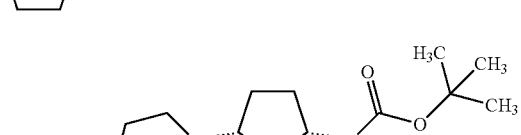 |
| (77) | 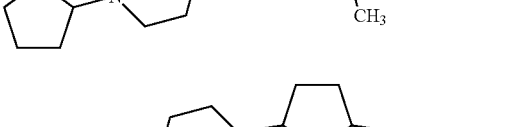 |
| (78) | 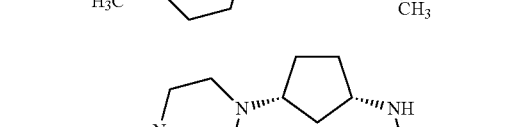 |
| (79) | 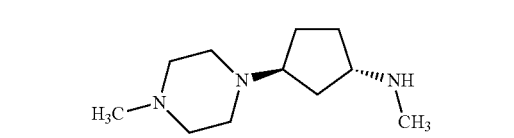 |
| (80) | 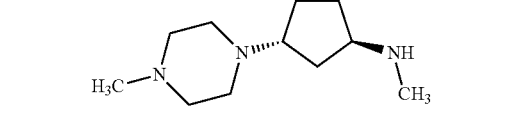 |
| (81) | 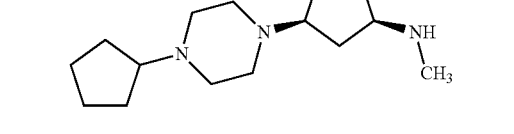 |
| (82) | 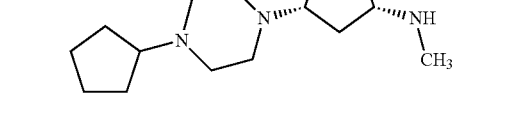 |
| (83) | 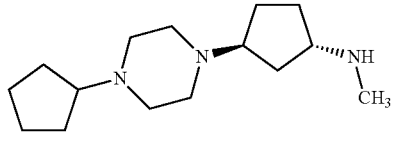 [SMILES: CN[C@H]1CC[C@H](N2CCN(C3CCCC3)CC2)C1] |
| (84) | 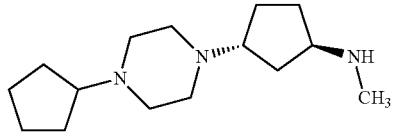 [SMILES: CN[C@@H]1CC[C@@H](N2CCN(C3CCCC3)CC2)C1] |
| (85) | 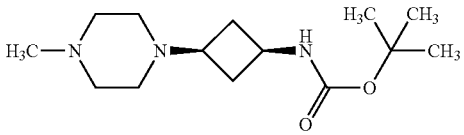 [SMILES: CN1CCN([C@H]2C[C@@H](NC(=O)OC(C)(C)C)C2)CC1] |
| (86) | 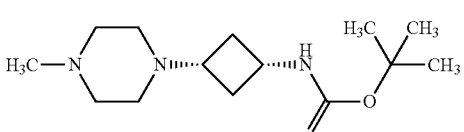 |
| (87) | 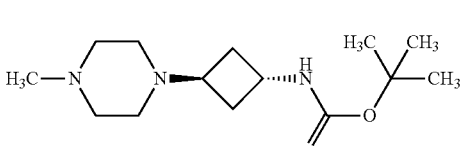 |
| (88) | 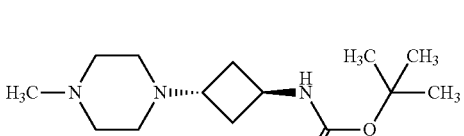 |
| (89) | 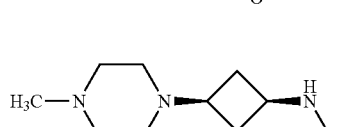 |
| (90) | 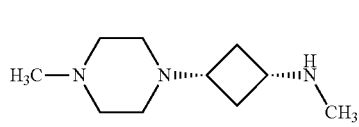 |
| (91) | 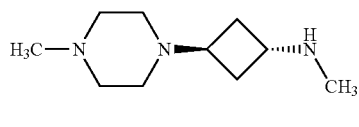 |
| (92) | 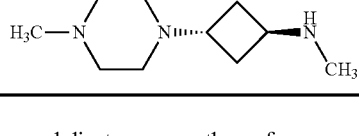 |
the enantiomers and diastereomers thereof.

In another aspect the present invention relates to the use of the previously mentioned compounds of general formula Ia, wherein m, n, $R^1$ and $R^2$ are as hereinbefore defined, as intermediate products for preparing compounds of general formula I wherein A, B, D, Y, $R^1$, $R^2$, $R^3$, $R^4$ and $R^5$ are as hereinbefore defined.

Terms and Definitions Used

Unless otherwise stated, all the substituents are independent of one another. If for example there are a plurality of $C_{1-6}$-alkyl groups as substituents in one group, in the case of three $C_{1-6}$-alkyl substituents, independently of one another, one may represent methyl, one n-propyl and one tert-butyl.

Within the scope of this application, in the definition of possible substituents, these may also be represented in the form of a structural formula. If present, an asterisk (*) in the structural formula of the substituent is to be understood as being the linking point to the rest of the molecule.

The subject-matter of this invention also includes the compounds according to the invention, including the salts thereof, wherein one or more hydrogen atoms, for example one, two, three, four or five hydrogen atoms, are replaced by deuterium.

By the term "$C_{1-3}$-alkyl" (including those which are part of other groups) are meant alkyl groups with 1 to 3 carbon atoms and by the term "$C_{1-4}$-alkyl" are meant alkyl groups with 1 to 4 carbon atoms. Examples include: methyl, ethyl, n-propyl, iso-propyl, n-butyl, iso-butyl and tert.butyl. The following abbreviations may also optionally be used for the abovementioned groups: Me, Et, n-Pr, i-Pr, n-Bu, i-Bu, t-Bu, etc. etc. Unless stated otherwise, the definition propyl includes all the possible isomeric forms of the group. Thus, for example, propyl includes n-propyl and iso-propyl.

Moreover, the terms mentioned above also include those groups wherein each methylene group may be substituted by up to two fluorine atoms and each methyl group may be substituted by up to three fluorine atoms.

By the term "$C_{3-5}$-cycloalkyl" (including those which are part of other groups) are meant cyclic alkyl groups with 3 to 5 carbon atoms and by the term "$C_{3-6}$-alkyl" are meant alkyl groups with 3 to 6 carbon atoms. Examples include: cyclopropyl, cyclobutyl, cyclopentyl or cyclohexyl. Unless otherwise stated, the cyclic alkyl groups may be substituted by one or more groups selected from among methyl, ethyl, iso-propyl, tert-butyl, hydroxy, fluorine, chlorine, bromine and iodine.

By the term "$C_{4-6}$-cycloalkylene" (including those which are part of other groups) are meant cyclic alkylene groups with 4 to 6 carbon atoms. Examples include: cyclobutylene, cyclopentylene or cyclohexylene. Unless otherwise stated, the cyclic alkylene groups may be substituted by one or more groups selected from among methyl, ethyl, iso-propyl, tert-butyl, hydroxy, fluorine, chlorine, bromine and iodine.

A $C_4$- or a $C_5$-cycloalkylene group may be linked in the 1,2 position or in the 1,3 position to the remainder of the molecule, preferably in the 1,3 position. A $C_6$-cycloalkylene group may be linked in the 1,2 position, in the 1,3 position or in the 1,4 position to the remainder of the molecule, preferably in the 1,3 position.

By the term "saturated diaza-heterocycles" are meant six- or seven-membered heterocyclic rings which contain two nitrogen atoms. The ring is linked via both nitrogen atoms to the remainder of the molecule. Examples include:

If they contain suitable basic functions, for example amino groups, compounds of general formula I may be converted, particularly for pharmaceutical use, into the physiologically acceptable salts thereof with inorganic or organic acids. Examples of inorganic acids for this purpose include hydrobromic acid, phosphoric acid, nitric acid, hydrochloric acid, sulphuric acid, methanesulphonic acid, ethanesulphonic acid, benzenesulphonic acid or p-toluenesulphonic acid, while organic acids that may be used include malic acid, succinic acid, acetic acid, fumaric acid, maleic acid, mandelic acid, lactic acid, tartaric acid or citric acid. In addition, any tertiary amino groups present in the molecule may be quaternised. Alkyl halides are used for the reaction. According to the invention methyl iodide is preferably used for the quaternisation.

In addition, the compounds of general formula I, if they contain suitable carboxylic acid functions, may if desired be converted into the addition salts thereof with inorganic or organic bases. Examples of inorganic bases include alkali or alkaline earth metal hydroxides, e.g. sodium hydroxide or potassium hydroxide, or carbonates, ammonia, zinc or ammonium hydroxides; examples of organic amines include diethylamine, triethylamine, ethanolamine, diethanolamine, triethanolamine, cyclohexylamine or dicyclohexylamine.

The compounds according to the invention may be present as racemates, provided that they have only one chiral element, but may also be obtained as pure enantiomers, i.e. in the (R) or (S) form.

However, the application also includes the individual diastereomeric pairs of antipodes or mixtures thereof, which are obtained if there is more than one chiral element in the compounds of general formula I, as well as the individual optically active enantiomers of which the above-mentioned racemates are made up.

The invention relates to the compounds in question, optionally in the form of the individual optical isomers, mixtures of the individual enantiomers or racemates, in the form of the tautomers as well as in the form of the free bases or the corresponding acid addition salts with pharmacologically acceptable acids—such as for example acid addition salts with hydrohalic acids—for example hydrochloric or hydrobromic acid—or organic acids—such as for example oxalic, fumaric, diglycolic or methanesulphonic acid.

Methods of Preparation

According to the invention the compounds of general formula I are obtained by methods known per se, for example by the following methods:

Scheme 1

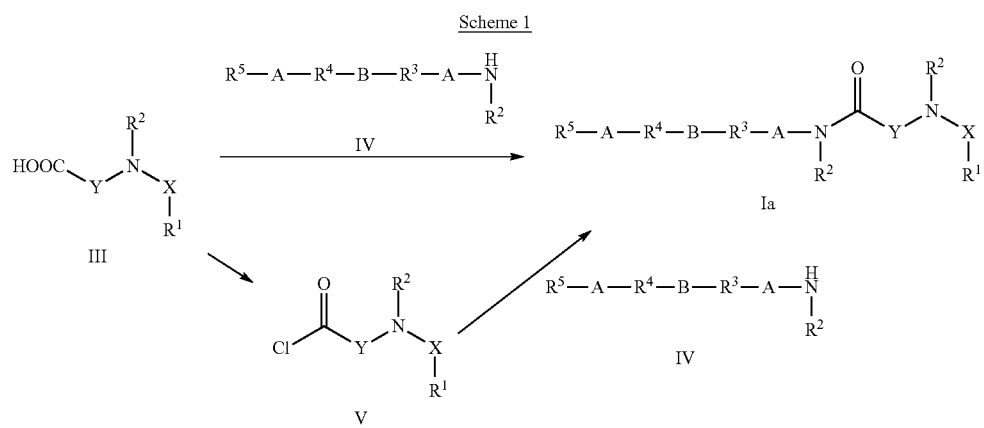

The linking of carboxylic acids of general formula III shown in Scheme 1 wherein all the groups are as hereinbefore defined, with amines of general formula IV, wherein all the groups are as hereinbefore defined, forming carboxylic acid amides of general formula Ia, wherein all the groups are as hereinbefore defined, may be carried out using conventional methods of amide formation.

The coupling is preferably carried out using methods known from peptide chemistry (cf. e.g. Houben-Weyl, Methoden der Organischen Chemie, Vol. 15/2), for example using carbodiimides such as e.g. dicyclohexylcarbodiimide (DCC), diisopropyl carbodiimide (DIC) or ethyl-(3-dimethylaminopropyl)-carbodiimide, O-(1H-benzotriazol-1-yl)-N,N-N',N'-tetramethyluronium hexafluorophosphate (HBTU) or tetrafluoroborate (TBTU) or 1H-benzotriazol-1-yl-oxy-tris-(dimethylamino)-phosphonium hexafluorophosphate (BOP). By adding 1-hydroxybenzotriazole (HOBt) or 3-hydroxy-4-oxo-3,4-dihydro-1,2,3-benzotriazine (HOObt) the reaction speed can be increased. The couplings are normally carried out with equimolar amounts of the coupling components as well as the coupling reagent in solvents such as dichloromethane, tetrahydrofuran, acetonitrile, dimethyl formamide (DMF), dimethyl acetamide (DMA), N-methylpyrrolidone (NMP) or mixtures thereof and at temperatures between −30° C. and +30° C., preferably −20° C. and +25° C. If necessary, N-ethyl-diisopropylamine (Hünig base) is preferably used as an additional auxiliary base.

An alternative method of attachment consists in converting a carboxylic acid of general formula III, wherein all the groups are as hereinbefore defined, into a carboxylic acid chloride of general formula V, wherein all the groups are as hereinbefore defined, and subsequent reaction with an amine of general formula IV, wherein all the groups are as hereinbefore defined. The synthesis of a carboxylic acid chloride of general formula V is carried out using methods known from the literature (see e.g. Houben-Weyl, Methoden der Organischen Chemie, vol. E5/1).

The carboxylic acids of general formula III used as starting materials, wherein all the groups are as hereinbefore defined, are obtained using methods known per se from the literature, for example by the methods of synthesis shown in Schemes 2 to 7.

Scheme 2

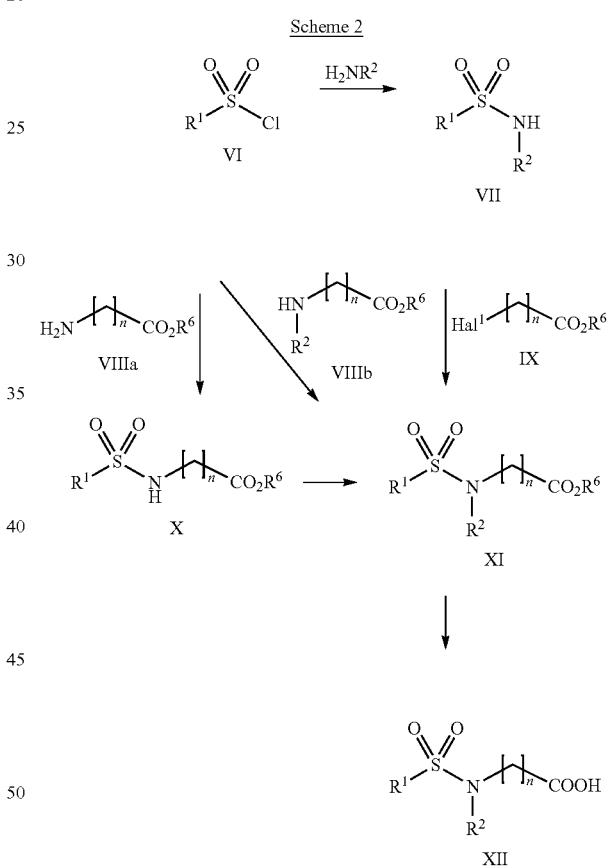

The sulphonic acid chlorides of general formula VI, wherein $R^1$ is as hereinbefore defined, are either known from the literature or commercially obtainable. They are reacted under standard reaction conditions with an amine of general formulae $H_2N$—$R^2$, VIIIa or VIIIb to obtain sulphonic acid amides of general formulae VII, X or XI, wherein $R^1$ and $R^2$ are hereinbefore defined and n denotes a number 1, 2, 3 or 4 and $R^6$ denotes a $C_{1-6}$-alkyl group. The reaction is optionally carried out in the presence of a base such as triethylamine, DIPEA or pyridine and an inert solvent such as dichloromethane or tetrahydrofuran at a temperature of 0° C. to 100° C. with a typical reaction time of one to 24 hours.

The reaction of the sulphonic acid amides of general formula VII with a halide of general formula IX, wherein Hal$^1$ denotes chlorine or bromine, is carried out using methods known from the literature, for example with the aid of a base such as potassium or sodium carbonate in dimethylformamide or tetrahydrofuran at 0° C. to 100° C.

The hydrolysis of the carboxylic acid esters of general formula XI, wherein R$^1$ and R$^2$ are as hereinbefore defined, n denotes a number 1, 2, 3 or 4 and R$^6$ denotes a C$_{1-3}$-alkyl group, to obtain carboxylic acids of general formula XII, wherein R$^1$ and R$^2$ are as hereinbefore defined and n denotes a number 1, 2, 3 or 4 and R$^6$ denotes a C$_{1-3}$-alkyl group, is carried out under known conditions, for example with lithium or sodium carbonate and water in methanol and/or tetrahydrofuran.

Scheme 3

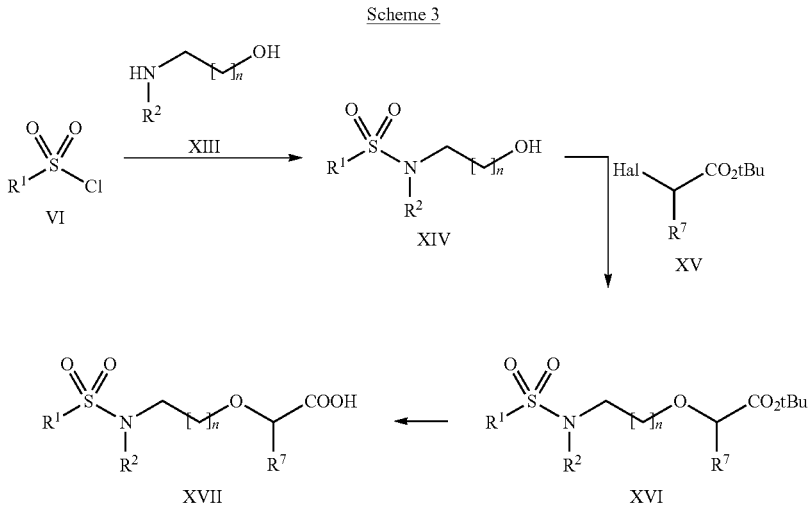

The preparation of sulphonic acid amides of general formula XIV is carried out as described under Scheme 2.

The alkylation of the hydroxyl function of the sulphonic acid amides of general formula XIV, wherein R$^1$ and R$^2$ are as hereinbefore defined with the proviso that R$^2$ does not denote a hydrogen atom, and n denotes a number 1, 2, 3 or 4 and R$^6$ denotes a C$_{1-3}$-alkyl group, is carried out under reaction conditions known from the literature, for example under 2-phase conditions using a phase transfer catalyst in the presence of a strong inorganic base such as sodium hydroxide solution or potassium hydroxide solution and in an inert solvent such as toluene at 0° C. to 100° C.

The cleaving of the tert-butylester of general formula XVI, wherein R$^1$ and R$^2$ are as hereinbefore defined, n denotes a number 1, 2, 3 or 4 and R$^6$ denotes a C$_{1-3}$-alkyl group and R$^7$ denotes a hydrogen atom or a C$_{1-3}$-alkyl group, is carried out using methods known from the literature (see e.g. Philip J. Kocieński, Protecting Groups, 3rd Edition, 2005, published by Georg Thieme).

Scheme 4

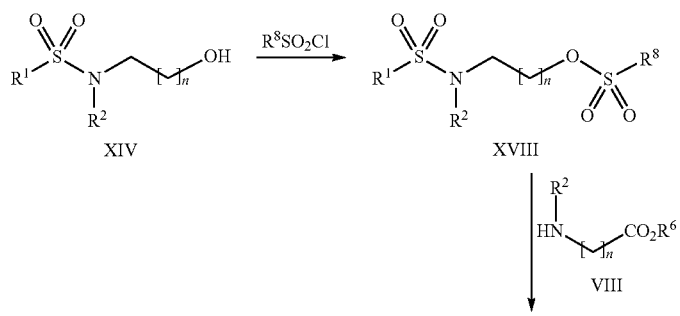

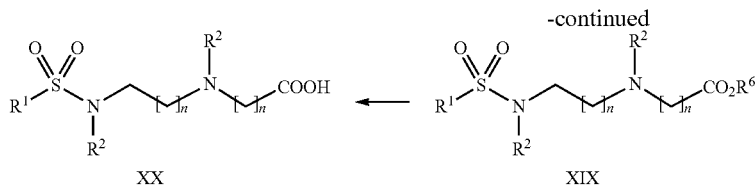

The sulphonation of the hydroxyl function of a compound of general formula XIV, wherein $R^1$ and $R^2$ are as hereinbefore defined, with the proviso that $R^2$ does not denote a hydrogen atom, and n denotes a number 1, 2, 3 or 4 and $R^6$ denotes a $C_{1-3}$-alkyl group, with a sulphonic acid chloride of general formula $R^8SO_2Cl$, wherein $R^8$ denotes a $C_{1-3}$-alkyl group or a phenyl group optionally substituted by a $C_{1-3}$-alkyl group, to form compounds of general formula XVIII, wherein all the groups are as hereinbefore defined, is carried out under standard reaction conditions, typically in the presence of a base such as DMAP and/or pyridine and an inert solvent such as dichloromethane or THF at −5° C. to 35° C. A liquid base such as pyridine may be used as the base and solvent simultaneously.

The subsequent alkylation of the amines of general formula VII to form compounds of general formula XIX, wherein $R^1$ and $R^2$ are as hereinbefore defined, n denotes a number 1, 2, 3 or 4 and $R^6$ denotes a $C_{1-3}$-alkyl group and $R^6$ denotes a $C_{1-6}$-alkyl group, is conveniently carried out in a solvent such as toluene, chlorobenzene, dimethylformamide, dimethylsulphoxide (DMSO), dichloromethane, acetonitrile or pyridine, for example at temperatures between 0° C. and 150° C. and conveniently in the presence of bases such as pyridine, triethylamine, DIPEA, potassium carbonate, potassium-tert-butoxide or sodium methoxide, the alkylsulphonate serving as the leaving group.

The hydrolysis of the carboxylic acid esters of general formula XIX to form carboxylic acids of general formula XX is carried out as described under Scheme 2.

The Finkelstein reaction of compounds of general formula XVIII, wherein $R^1$ and $R^2$ are as hereinbefore defined, n denotes a number 1, 2, 3 or 4 and $R^6$ denotes a $C_{1-3}$-alkyl group and $R^8$ denotes a $C_{1-3}$-alkyl group or a phenyl group optionally substituted by a $C_{1-3}$-alkyl group, to form halides of general formula XXI, wherein $R^1$ and $R^2$ are as hereinbefore defined and n denotes a number 1, 2, 3 or 4 and $R^6$ denotes a $C_{1-3}$-alkyl group, is carried out under known reaction conditions (see e.g. H. Finkelstein, Berichte der Deutschen Chemischen Gesellschaft 43, 1910, 1528).

The subsequent alkylation of the glycine ester is carried out as described under Scheme 4 ($R^2 \neq H$).

The amino function in the compounds of general formula XXIII is protected by a conventional protective group PG by known methods. The selected protective group is one which can be cleaved under non-hydrogenolytic conditions. A preferred protective group is the Boc group. An overview of the chemistry of protective groups can be found in Theodora W. Greene and Peter G. M. Wuts, Protective Groups in Organic Synthesis, Second Edition, 1991, published by John Wiley and Sons, and in Philip J. Kociénski, Protecting Groups, 3rd Edition, 2005, published by Georg Thieme.

The cleaving of the carboxylic acid esters of general formula XXIII to form carboxylic acids of general formula XXIV is carried out as described under Scheme 2.

Scheme 5

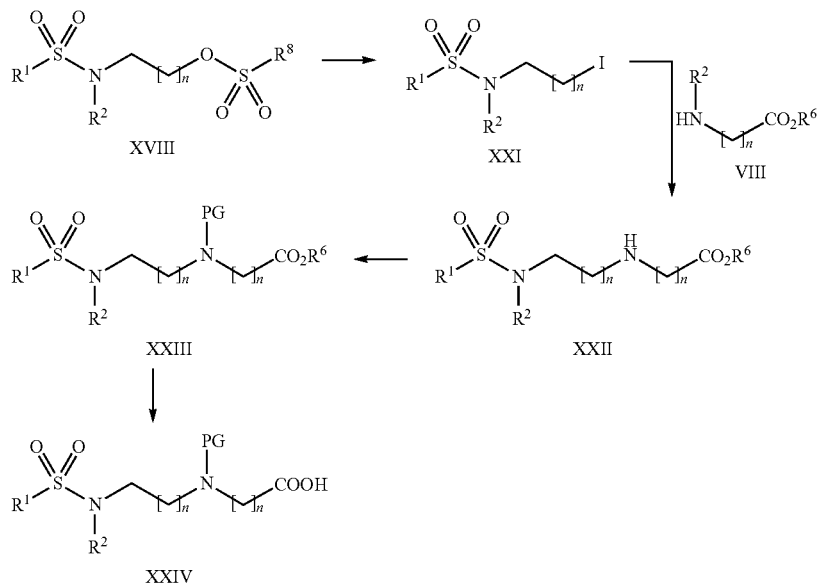

Scheme 6

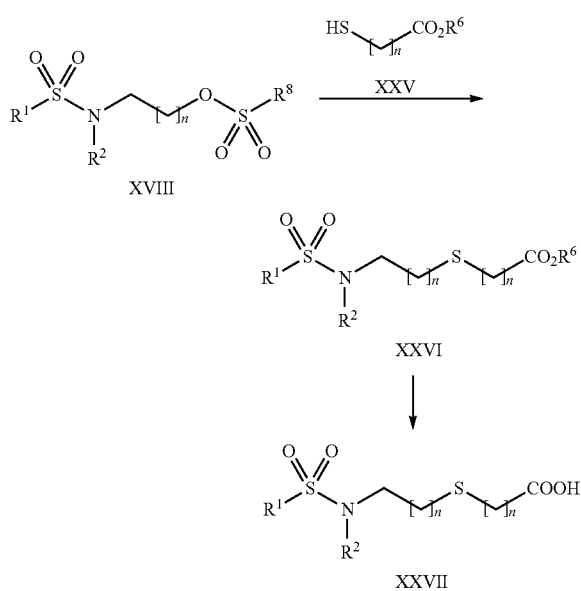

The alkylation of a thiol of general formula XXV, wherein n denotes a number 1, 2, 3 or 4 and $R^6$ denotes a $C_{1-6}$-alkyl group, to obtain compounds of general formula XXVI, wherein $R^1$ and $R^2$ are as hereinbefore defined, n denotes a number 1, 2, 3 or 4 and $R^6$ denotes a $C_{1-6}$-alkyl group, is conveniently carried out in a solvent such as toluene, chlorobenzene, DMF, DMSO, dichloromethane, acetonitrile or pyridine, for example at temperatures between 0° C. and 150° C. and conveniently in the presence of bases such as pyridine, triethylamine, DIPEA, potassium carbonate, potassium-tert-butoxide or sodium methoxide, while the alkylsulphonate serves as leaving group.

The hydrolysis of the carboxylic acid esters of general formula XXVI to form carboxylic acids of general formula XVII, wherein all the groups are as hereinbefore defined, is carried out as described under Scheme 2.

Scheme 7

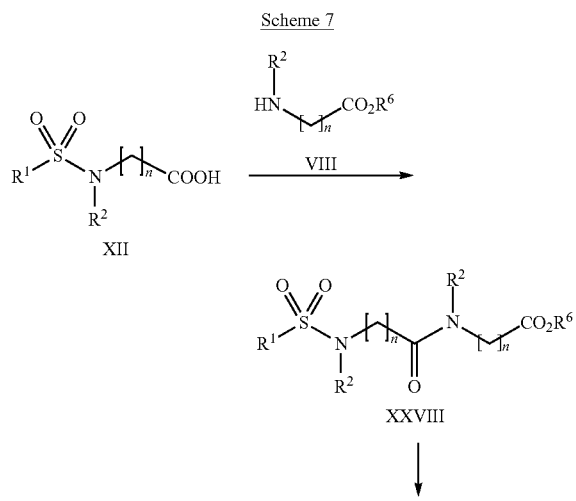

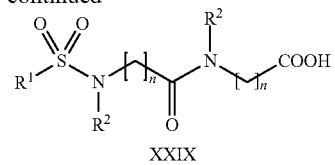

The amide linking of carboxylic acids of general formula XII, wherein $R^1$ and $R^2$ are as hereinbefore defined and n denotes a number 1, 2, 3 or 4, and amino acids of general formula VIII, wherein $R^1$ and $R^2$ are as hereinbefore defined, n denotes a number 1, 2, 3 or 4 and $R^6$ denotes a $C_{1-6}$-alkyl group, to obtain carboxylic acid amides of general formula XVIII, wherein $R^1$ and $R^2$ are as hereinbefore defined, n denotes a number 1, 2, 3 or 4 and $R^6$ denotes a $C_{1-6}$-alkyl group, is carried out as described under Scheme 1.

As mentioned under Scheme 2, the carboxylic acid ester of general formula XVIII is cleaved to form carboxylic acid of general formula XXIX, wherein $R^1$ and $R^2$ are as hereinbefore defined and n denotes a number 1, 2, 3 or 4.

The amines of general formula IV used as starting materials are either commercially obtainable, or are obtained using methods known per se from the literature, for example by the methods of synthesis represented in Schemes 8 to 12, wherein $R^{1.1}$ is as hereinbefore defined, $Hal^1$ denotes a chlorine or bromine atom and $Hal^2$ denotes a fluorine, chlorine or bromine atom or a group $R^9$.

Scheme 8

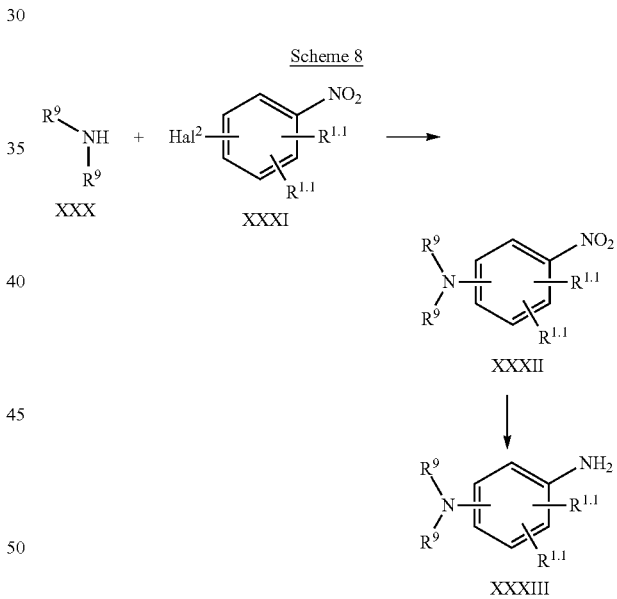

The reaction of an amine of general formula XXX, wherein $R^9$ denotes a $C_{1-3}$-alkyl group, with a halo-nitrobenzene of general formula XXXI, wherein $R^{1.1}$ is as hereinbefore defined and $Hal^2$ denotes a fluorine, chlorine or bromine atom or a group $R^9$, is carried out using known methods, for example in a solvent such as tetrahydrofuran, dimethylformamide or dimethylsulphoxide and conveniently in the presence of a suitable base such as triethylamine or potassium carbonate, at a temperature of 20° C. to 160° C. If the amine of general formula XXX is liquid, the reaction may also be carried out without a solvent and additional base.

The reduction of the nitro group to form anilines of general formula XXXIII, wherein $R^{1.1}$ is as hereinbefore defined and $R^9$ denotes a $C_{1-3}$-alkyl group, is carried out under standard reaction conditions (see e.g. Richard C. Larock, Comprehensive Organic Transformations, 1989, VCH), preferably under standard conditions of catalytic hydrogenolysis with a catalyst such as palladium on charcoal or Raney nickel in a solvent such as methanol or ethanol.

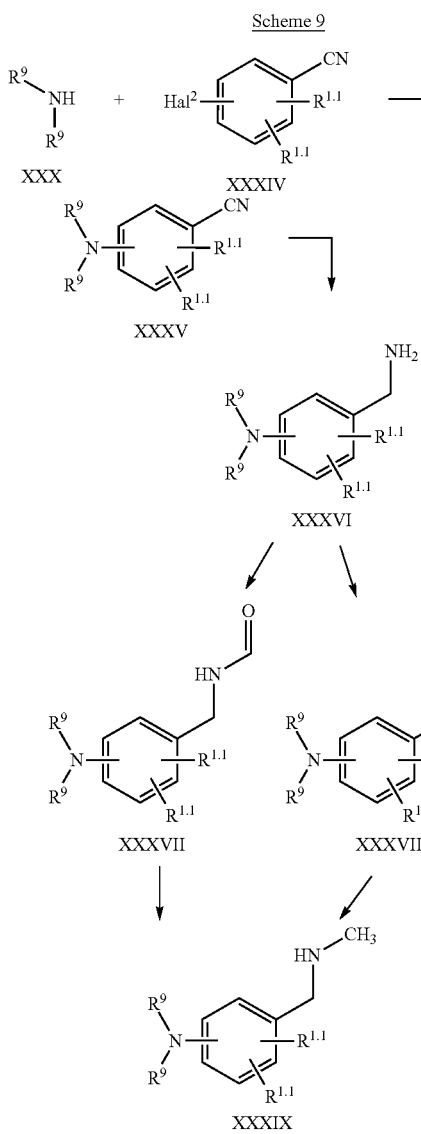

The reaction of compounds of general formulae XXX, wherein $R^9$ denotes a $C_{1-3}$-alkyl group, with a compound of general formula XXXIV, wherein $R^{1.1}$ is as hereinbefore defined and $Hal^2$ denotes a fluorine, chlorine or bromine atom or a group $R^9$, to obtain compounds of general formula XXXV, wherein $R^{1.1}$ is as hereinbefore defined and $R^9$ denotes a $C_{1-3}$-alkyl group, is carried out as described under Scheme 8.

The reduction of a nitrile of general formula XXXV to form an amine of general formula XXXVI, wherein $R^{1.1}$ is as hereinbefore defined and $R^9$ denotes a $C_{1-3}$-alkyl group, may be carried out under standard conditions of catalytic hydrogenolysis with a catalyst such as for example Raney nickel in a solvent such as ammoniacal methanol or ethanol or with a reducing agent such as lithium aluminium hydride or sodium borohydride in a solvent such as tetrahydrofuran, optionally in the presence of aluminium chloride.

The formylation of an amine of general formula XXXVI to obtain a compound of general formula XXXVII, wherein $R^{1.1}$ is as hereinbefore defined and $R^9$ denotes a $C_{1-3}$-alkyl group, is conveniently carried out in a solvent such as dichloromethane, for example at temperatures from 40° C. to 70° C. and in the presence of acetic anhydride and formic acid.

The carbamate formation to obtain compounds of general formula XXXVIII, wherein $R^{1.1}$ is as hereinbefore defined, $R^6$ denotes a $C_{1-6}$-alkyl and $R^9$ denotes a $C_{1-3}$-alkyl group is carried out by known methods, for example with a chloroformic acid ester or Boc-anhydride in the presence of a base such as triethylamine or sodium hydroxide solution and a solvent such as THF or dioxane.

The reduction of the formyl or of the carbamate to obtain compounds of general formula XXXIX, wherein $R^{1.1}$ is as hereinbefore defined and $R^9$ denotes a $C_{1-3}$-alkyl group, is carried out under standard reaction conditions, preferably with a reducing agent such as lithium aluminium hydride and in a solvent such as tetrahydrofuran at a temperature of 50° C. to 100° C.

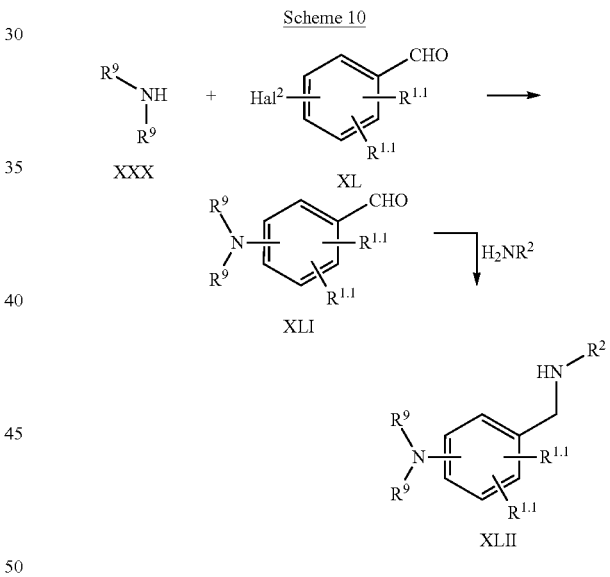

The halogen-nitrogen exchange in compounds of general formulae XXX, wherein $R^9$ denotes a $C_{1-3}$-alkyl group, and XL, wherein $R^{1.1}$ is as hereinbefore defined and $Hal^2$ denotes a fluorine, chlorine or bromine atom or a group $R^9$, for preparing compounds of general formula XLI, wherein $R^{1.1}$ is as hereinbefore defined and $R^9$ denotes a $C_{1-3}$-alkyl group, is carried out as described under Scheme 8.

The reaction of benzaldehydes of general formula XLI, wherein $R^{1.1}$ is as hereinbefore defined and $R^9$ denotes a $C_{1-3}$-alkyl group, with an amine of general formula $H_2NR^2$, wherein $R^2$ is as hereinbefore defined, to obtain a compound of general formula XLII, wherein $R^{1.1}$ and $R^2$ are as hereinbefore defined and $R^9$ denotes a $C_{1-3}$-alkyl group, is a reductive amination. It is carried out by known methods, for example with a reducing agent such as sodium triacetoxyborohydride, sodium borohydride or sodium cyanoborohydride, conveniently in a solvent such as tetrahydrofuran or dichloromethane, optionally with the addition of acetic acid.

Scheme 11

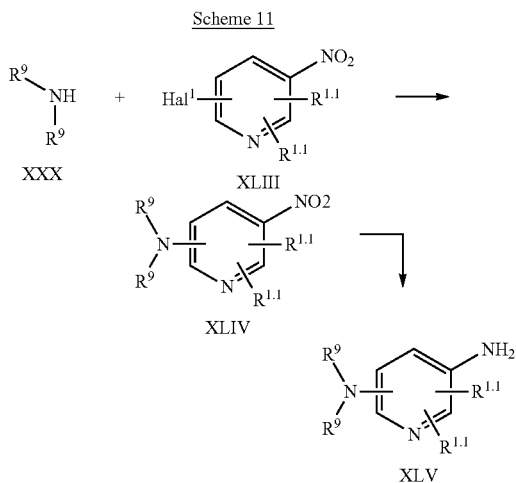

The reaction of an amine of general formula XXX, wherein $R^9$ denotes a $C_{1-3}$-alkyl group, with a halogen-nitropyridine of general formula XLIII, wherein $R^{1.1}$ is as hereinbefore defined and $Hal^1$ denotes a chlorine or bromine atom, is carried out by known methods, for example in a solvent such as tetrahydrofuran, dichloromethane, methanol or DMSO and conveniently in the presence of a suitable base such as triethylamine, sodium hydroxide solution or potassium carbonate and at a temperature of 20° C. to 100° C.

The subsequent reduction of the nitro group of a compound of general formula XLIV, wherein $R^{1.1}$ is as hereinbefore defined and $R^9$ denotes a $C_{1-3}$-alkyl group, to obtain compounds of general formula XLV, wherein $R^{1.1}$ is as hereinbefore defined and $R^9$ denotes a $C_{1-3}$-alkyl group, is carried out as described under Scheme 8.

Scheme 12

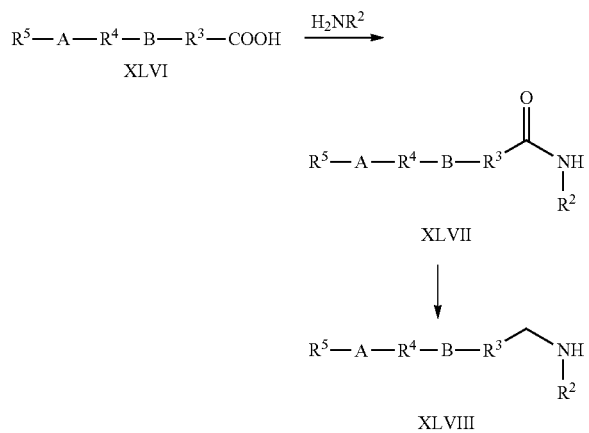

The amide linking of carboxylic acids of general formula XLVI, wherein all the groups are as hereinbefore defined, and amines of general formula $H_2NR^2$, wherein $R^2$ is as hereinbefore defined, to form carboxylic acid amides of general formula XLVII, wherein all the groups are as hereinbefore defined, is carried out as described under Scheme 1.

The reduction of carboxylic acid amides of general formula XLVII to obtain amines of general formula XLVIII, wherein all the groups are as hereinbefore defined, is carried out under standard reaction conditions, preferably in the presence of a reducing agent such as lithium aluminium hydride and a solvent such as tetrahydrofuran at 40° C. to 100° C.

Description of the Method of hBK1 Receptor Binding

CHO cells expressing the hBK1 receptor are cultivated in Dulbecco's modified medium. The medium from confluent cultures is removed and the cells are washed with PBS buffer, scraped off and isolated by centrifugation. The cells are then homogenized in suspension and the homogenate is centrifuged and resuspended. The protein content is determined and the membrane preparation obtained in this manner is then frozen at −80° C.

After thawing, 200 µl of the homogenate (50 to 100 µg of proteins/assay) are incubated at room temperature with 0.5 to 1.0 nM of kallidin (DesArg10, Leu9), [3,4-prolyl-3,43H(N)] and increasing concentrations of the test substance in a total volume of 250 µl for 60 minutes. The incubation is terminated by rapid filtration through GF/B glass fibre filters which had been pretreated with polyethyleneimine (0.3%). The protein-bound radioactivity is measured in a TopCount NXT. Non-specific binding is defined as radioactivity bound in the presence of 1.0 µM of kallidin (DesArg10, Leu9), [3,4-prolyl-3, 43H(N)]. The concentration/binding curve is analysed using a computer-assisted nonlinear curve fitting. The $K_i$ which corresponds to the test substance is determined using the data obtained in this manner.

To demonstrate that the compounds of general formula I with different structural elements show good to very good bradykinin-B1-receptor antagonistic effects, the following Table gives the $K_i$ values obtained according to the test method described above. It is pointed out that the compounds were selected for their different structural elements and not in order to emphasise specific compounds:

| Example | $K_i$ [nM] |
| --- | --- |
| (1) | 8.7 |
| (3) | 5.1 |

Indications

By virtue of their pharmacological properties, the novel compounds and their physiologically acceptable salts are suitable for treating diseases and symptoms of diseases caused at least to some extent by stimulation of bradykinin-B1 receptors.

In view of their pharmacological effect the substances are suitable for the treatment of (a) acute pain such as e.g. toothache, peri- and postoperative pain, traumatic pain, muscle pain, the pain caused by burns, sunburn, trigeminal neuralgia, pain caused by colic, as well as spasms of the gastro-intestinal tract or uterus;

(b) visceral pain such as e.g. chronic pelvic pain, gynaecological pain, pain before and during menstruation, pain caused by pancreatitis, peptic ulcers, interstitial cystitis, renal colic, angina pectoris, pain caused by irritable bowel, non-ulcerative dyspepsia and gastritis, non-cardiac thoracic pain and pain caused by myocardial ischaemia and cardiac infarct;

(c) neuropathic pain such as e.g. painful neuropathies, pain of diabetic neuropathy, AIDS-associated neuropathic pain, pain of lumbago, non-herpes-associated neuralgia, post-zoster neuralgia, nerve damage, cerebro-cranial trauma, pain of nerve damage caused by toxins or chemotherapy, phantom pain, pain of multiple sclerosis, nerve root tears and painful traumatically-caused damage to individual nerves;

(d) inflammatory/pain receptor-mediated pain in connection with diseases such as osteoarthritis, rheumatoid arthritis, rheumatic fever, tendo-synovitis, tendonitis, gout, vulvodynia, damage to and diseases of the muscles and fascia (muscle injury, fibromyalgia), osteoarthritis, juvenile arthritis, spondylitis, gout-arthritis, psoriasis-arthritis, fibromyalgia, myositis, migraine, dental disease, influenza and other virus infections such as colds, systemic lupus erythematodes, (e) tumour pain associated with cancers such as lymphatid or myeloid leukaemia, Hodgkin's disease, non-Hodgkin's lymphomas, lymphogranulomatosis, lymphosarcomas, solid malignant tumours and extensive metastases;

(f) headache diseases such as e.g. headache of various origins, cluster headaches, migraine (with or without aura) and tension headaches.

The compounds are also suitable for treating (g) inflammatory changes connected with diseases of the airways such as bronchial asthma, including allergic asthma (atopic and non-atopic) as well as bronchospasm on exertion, occupationally induced asthma, viral or bacterial exacerbation of an existing asthma and other non-allergically induced asthmatic diseases;

chronic obstructive pulmonary disease (COPD) including pulmonary emphysema, acute adult respiratory distress syndrome (ARDS), bronchitis, lung inflammation, allergic rhinitis (seasonal and all year round), vasomotor rhinitis and diseases caused by dust in the lungs such as aluminosis, anthracosis, asbestosis, chalicosis, siderosis, silicosis, tabacosis and byssinosis;

(h) inflammatory phenomena caused by sunburn and burns, oedema after burns trauma, cerebral oedema and angiooedema, intestinal complaints including Crohn's diseases and ulcerative colitis, irritable bowel syndrome, pancreatitis, nephritis, cystitis (interstitial cystitis), uveitis; inflammatory skin diseases (such as e.g. psoriasis and eczema), vascular diseases of the connective tissue, lupus, sprains and fractures;

(i) diabetes mellitus and its effects (such as e.g. diabetic vasculopathy, diabetic neuropathy, diabetic retinopathy) and diabetic symptoms in insulitis (e.g. hyperglycaemia, diuresis, proteinuria and increased renal excretion of nitrite and kallikrein);

(j) neurodegenerative diseases such as Parkinson's disease and Alzheimer's disease;

(k) sepsis and septic shock after bacterial infections or after trauma;

(l) syndromes that cause itching and allergic skin reactions;

(m) osteoporosis;

(n) epilepsy;

(o) damage to the central nervous system;

(p) wounds and tissue damage;

(q) inflammation of the gums;

(r) benign prostatic hyperplasia and hyperactive bladder;

(s) pruritus;

(t) vitiligo;

(u) disorders of the motility of respiratory, genito-urinary, gastro-intestinal or vascular regions and (v) post-operative fever.

In addition to being suitable as human therapeutic agents, these substances are also useful in the veterinary treatment of domestic animals, exotic animals and farm animals.

For treating pain, it may be advantageous to combine the compounds according to the invention with stimulating substances such as caffeine or other pain-alleviating active compounds. If active compounds suitable for treating the cause of the pain are available, these can be combined with the compounds according to the invention. If, independently of the pain treatment, other medical treatments are also indicated, for example for high blood pressure or diabetes, the active compounds required can be combined with the compounds according to the invention.

The following compounds may be used for combination therapy, for example:

Non-steroidal antirheumatics (NSAR): COX-2 inhibitors such as propionic acid derivatives (alminoprofen, benoxaprofen, bucloxic acid, carprofen, fenhufen, fenoprofen, fiuprofen, fiulbiprofen, ibuprofen, indoprofen, ketoprofen, miroprofen, naproxen, oxaprozin, pirprofen, pranoprofen, suprofen, tiaprofenic acid, tioxaprofen), acetic acid derivatives (indomethacin, acemetacin, alcofenac, isoxepac, oxpinax, sulindac, tiopinac, tolmetin, zidometacin, zomepirac) fenamic derivatives (meclofenamic acid, mefenamic acid, tolfenamic acid), biphenyl-carboxylic acid derivatives, oxicams (isoxicam, meloxicam, piroxicam, sudoxicam and tenoxicam), salicylic acid derivatives (acetylsalicylic acid, sulphasalazin, mesalazine, and olsalazine), pyrazolone (apazone, bezpiperylone, feprazone, mofebutazone, oxyphenbutazone, phenylbutazone, propyphenazone and metamizol), and coxibs (celecoxib, valecoxib, rofecoxib, etoricoxib).

Opiate receptor agonists such as e.g. morphine, propoxyphen (Darvon), tramadol, buprenorphine.

Cannabinoid agonists such as e.g. GW-1000, KDS-2000, SAB-378, SP-104, NVP001-GW-843166, GW-842166X, PRS-211375.

Sodium channel blockers such as e.g. carbamazepine, mexiletin, lamotrigin, pregabalin, tectin, NW-1029, CGX-1002.

N-type calcium channel blockers such as e.g. ziconitide, NMED-160, SP1-860.

Serotonergic and noradrenergic modulators such as e.g. SR-57746, paroxetine, duloxetine, clonidine, amitriptyline, citalopram.

Corticosteroids such as e.g. betamethasone, budesonide, cortisone, dexamethasone, hydrocortisone, methylprednisolone, prednisolone, prednisone and triamcinolone.

Histamine H1-receptor antagonists such as e.g. bromopheniramine, chlorpheniramine, dexchlorpheniramine, triprolidine, clemastine, diphenhydramine, diphenylpyraline, tripelennamine, hydroxyzine, methdilazine, promethazine, trimeprazine azatadine, cyproheptadine, antazoline, pheniramine, pyrilamine, astemizole, terfenadine, loratadine, cetirizine, desloratadine, fexofenadine, levocetirizine.

Histamine H2-receptor antagonists such as e.g. cimetidine, famotidine, and ranitidine.

Proton pump inhibitors such as e.g. omeprazole, pantoprazole, esomeprazole.

Leukotriene antagonists and 5-lipoxygenasehemmer such as e.g. zafirlukast, montelukast, pranlukast and zileuton.

Local anaesthetics such as e.g. ambroxol, lidocaine.

VR1 agonists and antagonists such as e.g. NGX-4010, WL-1002, ALGRX-4975, WL-10001, AMG-517.

Nicotine receptor agonists such as e.g. ABT-202, A-366833, ABT-594, BTG-102, A-85380, CGX1204.

P2X3-receptor antagonists such as e.g. A-317491, ISIS-13920, AZD-9056.

NGF agonists and antagonists such as e.g. RI-724, RI-1024, AMG-819, AMG-403, PPH 207.

NK1 and NK2 antagonists such as e.g. DA-5018, R-116301, CP-728663, ZD-2249.

NMDA antagonists such as e.g. NER-MD-11, CNS-5161, EAA-090, AZ-756, CNP-3381.

potassium channel modulators such as e.g. CL-888, ICA-69673, retigabin.

GABA modulators such as e.g. lacosamide.

Serotonergic and noradrenergic modulators such as e.g. SR-57746, paroxetine, duloxetine, clonidine, amitriptyline, citalopram, flibanserine.

Anti-migraine drugs such as e.g. sumatriptan, zolmitriptan, naratriptan, eletriptan.

The dosage necessary for obtaining a pain-alleviating effect is, in the case of intravenous administration, expediently from 0.01 to 3 mg/kg of body weight, preferably from 0.1 to 1 mg/kg, and, in the case of oral administration, from 0.1 to 8 mg/kg of body weight, preferably from 0.5 to 3 mg/kg, in each case 1 to 3 times per day. The compounds prepared according to the invention can be administered intravenously, subcutaneously, intramuscularly, intrarectally, intranasally, by inhalation, transdermally or orally, aerosol formulations being particularly suitable for inhalation. They can be incorporated into customary pharmaceutical preparations, such as tablets, coated tablets, capsules, powders, suspensions, solutions, metered-dose aerosols or suppositories, if appropriate together with one or more customary inert carriers and/or diluents, for example with maize starch, lactose, cane sugar, microcrystalline cellulose, magnesium stearate, polyvinylpyrrolidone, citric acid, tartaric acid, water, water/ethanol, water/glycerol, water/sorbitol, water/polyethylene glycol, propylene glycol, cetylstearyl alcohol, carboxymethylcellulose or fatty substances, such as hardened fat, or suitable mixtures thereof.

Experimental Section

Generally, there are IR, $^1$H NMR and/or mass spectra for the compounds that were prepared. The ratios given for the eluants are in volume units of the solvents in question. For ammonia, the given volume units are based on a concentrated solution of ammonia in water.

Unless indicated otherwise, the acid, base and salt solutions used for working up the reaction solutions are aqueous systems having the stated concentrations. For chromatographic purification, silica gel from Millipore (MATREX™, 35-70 μm) or Alox (E. Merck, Darmstadt, Alumina 90 standardized, 63-200 μm, article No. 1.01097.9050) are used.

In the descriptions of the experiments, the following abbreviations are used:

Alox aluminium oxide
BOC tert.butoxycarbonyl
TLC thin layer chromatogram
DCM dichloromethane
DIPEA diisopropylethylamine
DMAP 4-dimethylaminopyridine
DMF dimethylformamide
DMSO dimethylsulphoxide
EE ethyl acetate
HCl hydrochloric acid
MeOH methanol
NaOH sodium hydroxide solution
TEA triethylamine
tert tertiary
TBTU 2-(1H-benzotriazol-1-yl)-1.1.3.3-tetramethyluronium-tetrafluoroborate
TFA trifluoroacetic acid
THF tetrahydrofuran The following analytical HPLC method was used:

| Method 1: | Column: | Zorbax Stable Bond C18, 3.5 μM, 4.6 × 75 mm |
| --- | --- | --- |
| | Detection: | 230-360 nm |
| | Eluant A: | water/0.1% formic acid |
| | Eluant B: | acetonitrile/0.1% formic acid |
| | Gradient: | |

| time in min | % A | % B | flow rate in mL/min |
| --- | --- | --- | --- |
| 0.0 | 95.0 | 5.0 | 1.6 |
| 0.1 | 95.0 | 5.0 | 1.6 |
| 4.5 | 10.0 | 90.0 | 1.6 |
| 5.09 | 10.0 | 90.0 | 1.6 |
| 5.5 | 90.0 | 10.0 | 1.6 |

| Method 2: | Column: | Merck Cromolith Speed ROD RP18e, 4.6 × 50 mm |
| --- | --- | --- |
| | Detection: | 190-400 nm |
| | Eluant A: | water/0.1% formic acid |
| | Eluant B: | acetonitrile/0.1% formic acid |
| | Gradient: | |

| time in min | % A | % B | flow rate in mL/min |
| --- | --- | --- | --- |
| 0.0 | 90.0 | 10.0 | 1.5 |
| 4.5 | 10.0 | 90.0 | 1.5 |
| 5.0 | 10.0 | 90.0 | 1.5 |
| 5.5 | 90.0 | 10.0 | 1.5 |

| Method 3: | Column: | Merck Cromolith Flash RP18e, 25 × 4.6 mm |
| --- | --- | --- |
| | Detection: | 190-400 nm |
| | Eluant A: | water/0.1% formic acid |
| | Eluant B: | acetonitrile/0.1% formic acid |
| | Gradient: | |

| time in min | % A | % B | flow rate in mL/min |
| --- | --- | --- | --- |
| 0.0 | 90.0 | 10.0 | 1.6 |
| 2.7 | 10.0 | 90.0 | 1.6 |
| 3.0 | 10.0 | 90.0 | 1.6 |
| 3.3 | 90.0 | 10.0 | 1.6 |

| Method 4: | Column: | Waters Xbridge C18, 2.5 μM, 3.0 × 30 mm |
| --- | --- | --- |
| | Detection: | 230-360 nm |
| | Eluant A: | water/0.1% ammonia |
| | Eluant B: | acetonitrile/0.1% ammonia |
| | Gradient: | |

| time in min | % A | % B | flow rate in mL/min |
| --- | --- | --- | --- |
| 0.0 | 95.0 | 5.0 | 1.4 |
| 1.6 | 50.0 | 5.0 | 1.4 |
| 1.8 | 10.0 | 90.0 | 1.4 |
| 2.0 | 10.0 | 90.0 | 1.4 |
| 2.2 | 95 | 10 | 1.4 |

| Method 5: | Column: | Waters Xbridge C18, 2.5 μM, 3.0 × 30 mm |
| --- | --- | --- |
| | Detection: | 230-360 nm |
| | Eluant A: | water/0.1% ammonia |
| | Eluant B: | acetonitrile/0.1% ammonia |
| | Gradient: | |

| time in min | % A | % B | flow rate in mL/min |
| --- | --- | --- | --- |
| 0.0 | 95.0 | 5.0 | 1.4 |
| 1.8 | 10.0 | 90.0 | 1.4 |
| 2.0 | 10.0 | 90.0 | 1.4 |
| 2.0 | 10.0 | 90.0 | 1.4 |

Method 6:
- Column: Waters Xbridge C18, 2.5 μM, 3.0 × 30 mm
- Detection: 230-360 nm
- Eluant A: water/0.1% ammonia
- Eluant B: acetonitrile/0.1% ammonia
- Gradient:

| time in min | % A | % B | flow rate in mL/min |
|---|---|---|---|
| 0.0 | 95.0 | 5.0 | 1.4 |
| 0.8 | 10.0 | 90.0 | 1.4 |
| 2.0 | 10.0 | 90.0 | 1.4 |
| 2.2 | 95.0 | 5.0 | 1.4 |

The following preparative methods were used for the reversed-phase chromatography:

Method 7:
- Column: Varian C18 Microsorb, 10 μM, 50 × 160 mm
- Detection: UV controlled
- Eluant A: water/0.2% TFA
- Eluant B: acetonitrile
- Gradient:

| time in min | % A | % B | flow rate in mL/min |
|---|---|---|---|
| 0.0 | 90.0 | 10.0 | 100.00 |
| 1.0 | 90.0 | 10.0 | 100.00 |
| 1.5 | 90.0 | 10.0 | 100.00 |
| 13.0 | 0 | 100.0 | 100.00 |
| 15.5 | 0 | 100.0 | 100.00 |
| 15.75 | 90.0 | 10.0 | 100.00 |
| 18.3 | 90.0 | 10.0 | 100.00 |

Method 8:
- Column: Merck Chromolith-prep RP 18 e, 100 × 25 mm
- Detection: UV controlled
- Eluant A: water/0.1% TFA
- Eluant B: acetonitrile/0.1% TFA
- Gradient:

| time in min | % A | % B | flow rate in mL/min |
|---|---|---|---|
| 0.0 | 90.0 | 10.0 | 20.00 |
| 7.5 | 10.0 | 90.0 | 20.00 |
| 9.0 | 10.0 | 90.0 | 20.00 |
| 10.0 | 90.0 | 10.0 | 20.00 |

Method 9:
- Column: Varian Pursuit XRs, 10 μM, 50 × 250 mm
- Detection: UV controlled
- Eluant A: water/0.2% TFA
- Eluant B: acetonitrile
- Gradient:

| time in min | % A | % B | flow rate in mL/min |
|---|---|---|---|
| 0.0 | 90.0 | 10.0 | 100.00 |
| 1.0 | 90.0 | 10.0 | 100.00 |
| 1.5 | 90.0 | 10.0 | 100.00 |
| 13.0 | 0 | 100.0 | 100.00 |
| 15.5 | 0 | 100.0 | 100.00 |
| 15.75 | 90.0 | 10.0 | 100.00 |
| 18.3 | 90.0 | 10.0 | 100.00 |

Method 10:
- Column: Varian C18 Pursuit XRs, 10 μM, 50 × 250 mm
- Detection: UV controlled
- Eluant A: water/0.2% ammonia
- Eluant B: acetonitrile
- Gradient:

| time in min | % A | % B | flow rate in mL/min |
|---|---|---|---|
| 0.0 | 90.0 | 10.0 | 100.00 |
| 1.0 | 90.0 | 10.0 | 100.00 |
| 1.5 | 90.0 | 10.0 | 180.00 |
| 13.0 | 0 | 100.0 | 180.00 |
| 15.5 | 0 | 100.0 | 180.00 |
| 15.75 | 90.0 | 10.0 | 180.00 |
| 19.0 | 90.0 | 10.0 | 180.00 |

Method 11:
- Column: Waters XBridge C18, 5 μM, 50 × 150 mm
- Detection: MS or UV controlled
- Eluant A: water/0.3% ammonia
- Eluant B: acetonitrile
- Gradient:

| time in min | % A | % B | flow rate in mL/min |
|---|---|---|---|
| 0.0 | 90.0 | 10.0 | 120.00 |
| 2.0 | 90.0 | 10.0 | 120.00 |
| 9.0 | 5.0 | 95.0 | 120.00 |
| 15.0 | 5.0 | 95.0 | 120.00 |
| 15.5 | 95.0 | 5.0 | 120.00 |
| 17.5 | 95.0 | 5.0 | 120.00 |

Method 12:
- Column: Varian Microsorb C18, 10 μM, 50 × 160 mm
- Detection: MS or UV controlled
- Eluant A: water/0.1% TFA
- Eluant B: methanol
- Gradient:

| time in min | % A | % B | flow rate in mL/min |
|---|---|---|---|
| 0.0 | 95.0 | 5.0 | 150.00 |
| 1.15 | 95.0 | 5.0 | 150.00 |
| 12.4 | 2.0 | 98.0 | 150.00 |
| 14.0 | 2.0 | 98.0 | 150.00 |
| 14.05 | 95.0 | 5.0 | 150.00 |
| 15.3 | 95.0 | 5.0 | 150.00 |

The following HPLC-methods were used for the preparative separation of enantiomers:

Method 13:
- Column: Daicel OJ-H, 250 × 4.6 mm, 5 μm
- Detection: 230-360 nm
- Eluant: n-hexane + 0.2% diethylamine/ethanol = 70:30
- Flow rate: 12 ml/min
- Gradient: isocratic Method 14:
- Column: Daicel AD-H, 250 * 4.6 mm, 5 μm, 10° C.
- Detection: 230-360 nm
- Eluant: n-hexane + 0.2% diethylamine/i-propyl = 85:15
- Flow rate: 1 ml/min
- Gradient: isocratic The following microwave apparatus was used: Biotage EmrysOptimizer™

PREPARATION OF THE END COMPOUNDS

Example 1

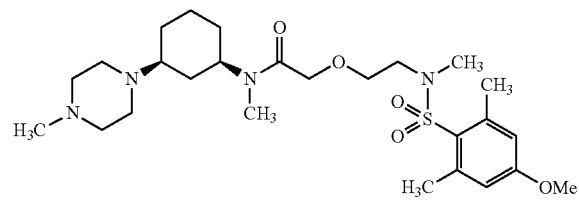 [SMILES: COc1cc(C)c(S(=O)(=O)N(C)CCOCC(=O)N(C)[C@@H]2CCC[C@H](N3CCN(C)CC3)C2)c(C)c1]

1a)

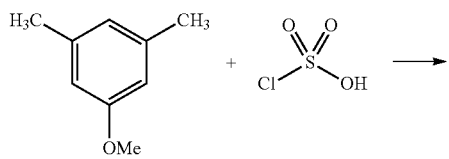

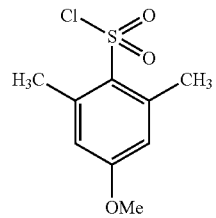

A mixture of 2.0 g (14.69 mmol) 3,5-dimethylanisol and 20 ml dichloromethane was combined with 5.85 ml (88.0 mmol) chlorosulphonic acid while cooling with an ice bath. The reaction mixture was then stirred for 20 min at ambient temperature and then poured onto 50 ml ice water. The mixture was extracted with 100 ml dichloromethane. The organic extracts were washed with 5% sodium hydrogen carbonate solution, dried on sodium sulphate and evaporated to dryness.

$C_9H_{11}ClO_3S$ (234.70)

[M+H]+=234/236

TLC: silica gel, petroleum ether/ethyl acetate 9:1, Rf value=0.46

1b)

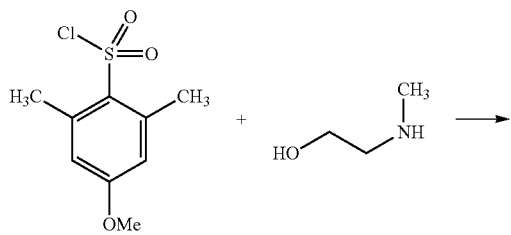

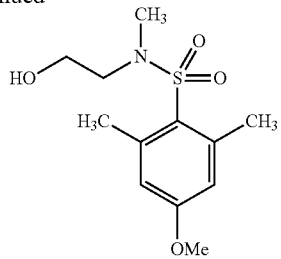

1.69 g (21.1 mmol) N-methylaminoethanol (BASF) and 6.68 ml (47.9 mmol) triethylamine were dissolved in 100 ml dichloromethane. At 0° C., 4.50 g (19.2 mmol) product of 1a dissolved in 50 ml dichloromethane were added dropwise. The cooling was removed and the mixture was stirred for 1.5 hours at ambient temperature. The reaction mixture was then washed with 1 N hydrochloric acid and 5% sodium hydrogen carbonate solution. The organic phase was dried on sodium sulphate and evaporated to dryness.

$C_{12}H_{19}NO_4S$ (273.35)

[M+H]+=274

TLC: silica gel, dichloromethane/ethanol 19:1, Rf value=0.43

1c)

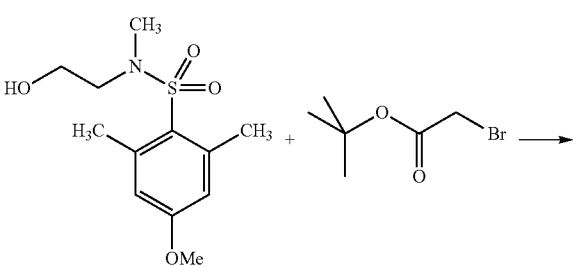

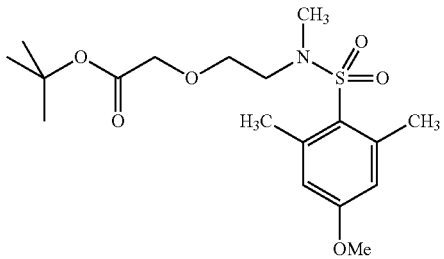

A mixture of 5.15 g (18.8 mmol) product from 1b), 1.75 g (6.60 mmol) tetrabutyl-ammonium chloride (Fluka) and 80 ml of toluene was combined first with 100 ml of 35% sodium hydroxide solution, then with 4.18 ml (28.3 mmol) tert-butyl bromoacetate in 20 ml of toluene at 0° C. The reaction mixture was then stirred for 1.5 hours at ambient temperature, then diluted with diethyl ether. After the phase separation the organic phase was washed four times with water until neutral, dried on sodium sulphate and evaporated to dryness in vacuo. The crude product thus obtained was purified by column chromatography through silica gel (eluant: petroleum ether/ethyl acetate 4:1).

$C_{18}H_{29}NO_6S$ (387.49)

[M+H]+=388

TLC: silica gel, petroleum ether/ethyl acetate 7:3, Rf value=0.59

1d)

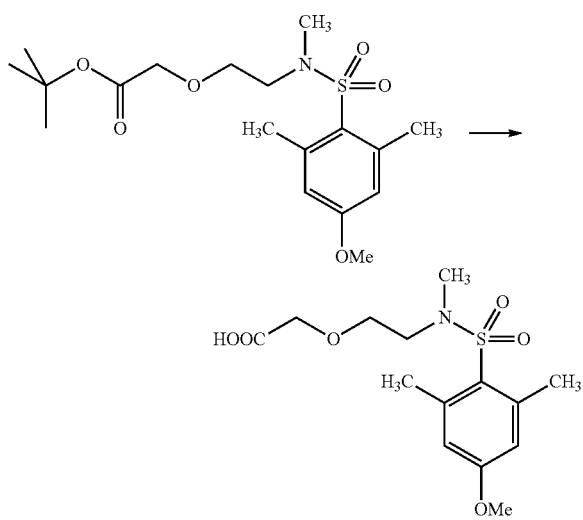

A mixture of 6.80 g (17.6 mmol) product 1c), 8 ml TFA and 100 ml dichloromethane was stirred for 2.5 hours at ambient temperature. The reaction mixture was then evaporated to dryness in vacuo. The residue was combined with 1 N sodium hydroxide solution and extracted twice with ethyl acetate (organic extracts were discarded). The aqueous phase was acidified with 2 M hydrochloric acid, then extracted again with ethyl acetate. The organic extracts were washed with water, dried on sodium sulphate and evaporated to dryness in vacuo.

$C_{14}H_{21}NO_6S$ (331.29)

[M+H]+=332 analytical HPLC (method 1): retention time=3.4 min

1e)

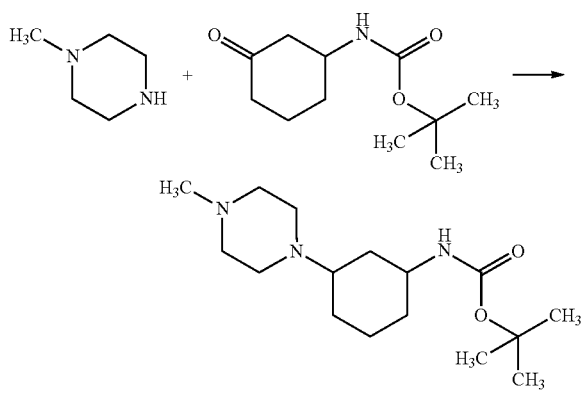

2.6 ml (23.4 mmol) 1-methylpiperazine, 1.0 g (4.69 mmol) 3-amino-N-tert-butyloxycarbonyl-cyclohexanone (AB Chem) and 2.7 ml (49 mmol) glacial acetic acid were dissolved in 10 ml of methanol and stirred for 30 minutes at ambient temperature. Then 1.99 g (9.38 mmol) sodium triacetoxyborohydride were added batchwise and the mixture was stirred for 2 hours at ambient temperature. Then the reaction solution was combined with hydrogen carbonate solution and extracted with dichloromethane. The organic phase was freed from the solvent in vacuo and the residue was chromatographed on RP phase (Varian C18 XRS, preparative HPLC method 10).

$C_{16}H_{31}N_3O_2$ (297.44)

[M+H]+=298

1f)

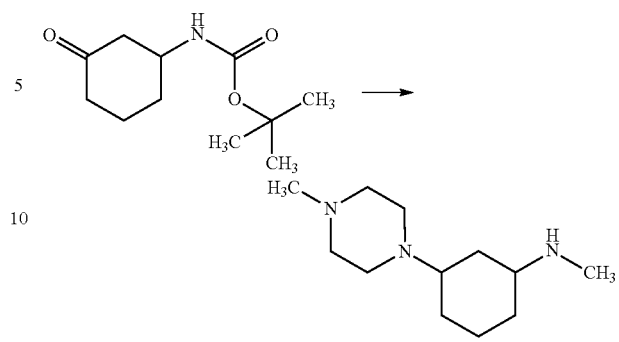

8.57 ml (8.57 mmol) of a 1 M solution of lithium aluminium hydride in toluene were dissolved in 8 ml THF and at ambient temperature 850 mg (2.86 mmol) product 1e dissolved in 2 ml THF were slowly added. The reaction solution was stirred for 2 hours at 75° C. Then 1 N sodium hydroxide solution and water were added. The precipitate was suction filtered and the reaction solution was evaporated to dryness.

$C_{12}H_{25}N_3$ (211.35)

[M+H]+=212 analytical HPLC (method 2): retention time=0.29 min

1g)

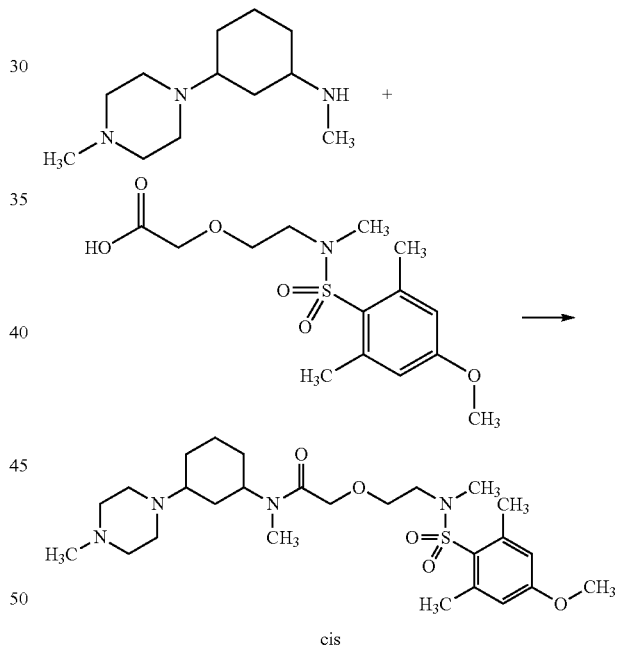

360 mg (1.01 mmol) product 1d), 384 mg (1.20 mmol) TBTU and 151 µl (1.09 mmol) triethylamine were dissolved in 5 ml DMF and the mixture was stirred for 5 minutes at ambient temperature. Then 460 mg (2.18 mmol) of product 1f) were added. The mixture was stirred for 2 hours at ambient temperature and then the solvent was eliminated in vacuo.

In order to separate the cis/trans mixture the residue was chromatographed on RP-phase (Merck Chromolith Speed ROD) (water+0.1% formic acid/acetonitrile+0.1% formic acid=90:10->0:100). In this way the racemic mixture of the cis isomers was obtained:

$C_{26}H_{44}N_4O_5S$ (524.72)

[M+H]+=525 analytical HPLC (method 2): retention time=1.53 min

1h)

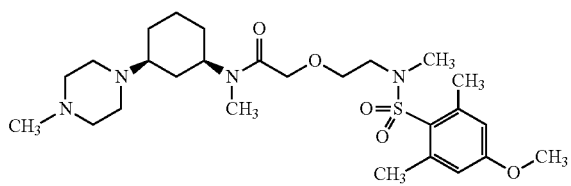
eluting fast

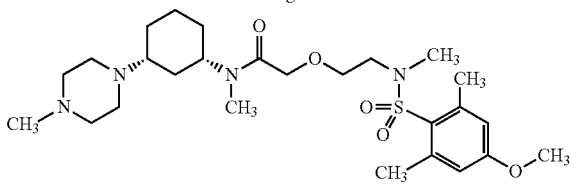
eluting slowly 31 mg of product 1g (cis diastereomer) were resolved into the enantiomers by HPLC Method 13 on the chiral phase.

HPLC (method 13): retention times=7.3 min (fast eluting enantiomer), 9.7 min (slowly eluting enantiomer)

Example 2

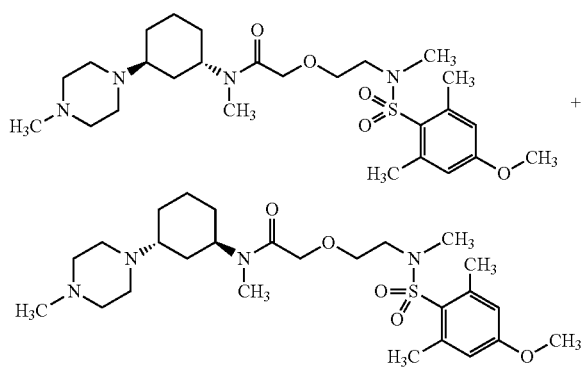

2a)

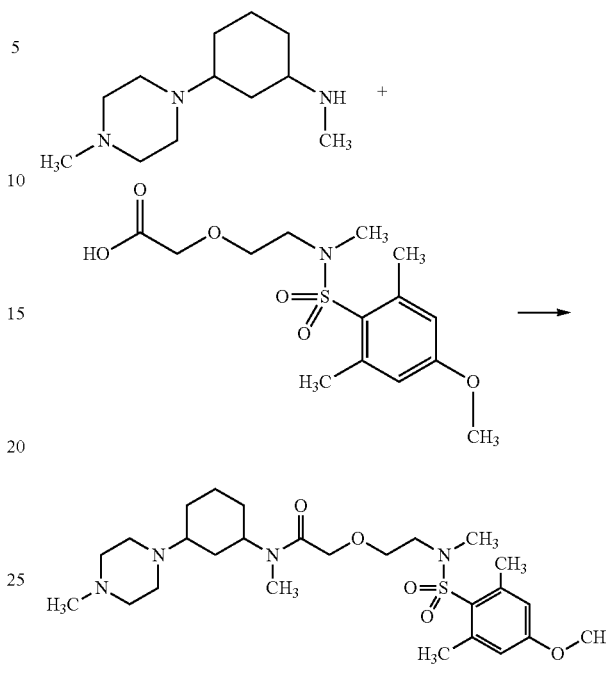
trans

Analogously to Example 1g) the title compound was prepared from product 1d) and product 1f). To separate the cis/trans mixture the residue was chromatographed on RP-phase (Merck Chromolith Speed ROD) (water+0.1% formic acid/acetonitrile+0.1% formic acid=90:10->0:100). In this way the racemic mixture of the trans-isomers was obtained:

trans-Diastereomer:

$C_{26}H_{44}N_4O_5S$ (524.72)

[M+H]+=525 analytical HPLC (method 2): retention time=1.41 min

Example 3

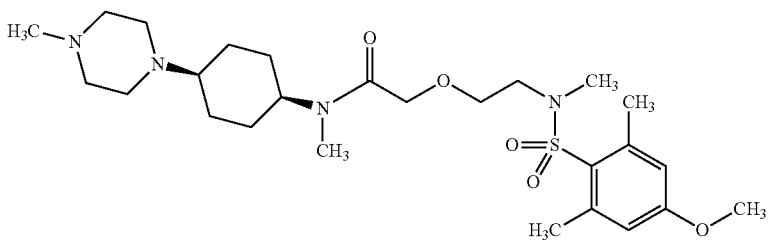

3a)

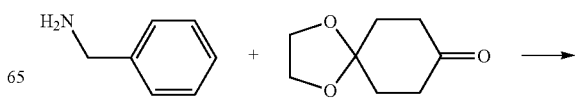

-continued

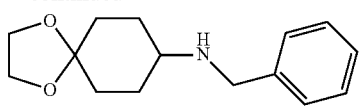

110 ml (1 mol) benzylamine and 156.2 g (1 mol) cyclohexanedione-monoethyleneketal, dissolved in 0.8 l toluene, were boiled for 2 h using the water separator. Then the reaction mixture was evaporated down and the residue was taken up in 1 l EtOH. The solution was combined batchwise with 23 g (0.61 mol) sodium borohydride at 15-20° C. and stirred overnight. Then the reaction mixture was evaporated down and the residue was combined with 500 ml of water and extracted twice with 400 ml ether. The organic phase was washed with water, dried and evaporated down. The residue was distilled under high vacuum.

$C_{15}H_{21}NO_2$ (247.33)

$[M+H]^+=248$ boiling temperature=125-127° C. (at 0.06 mbar)

3b)

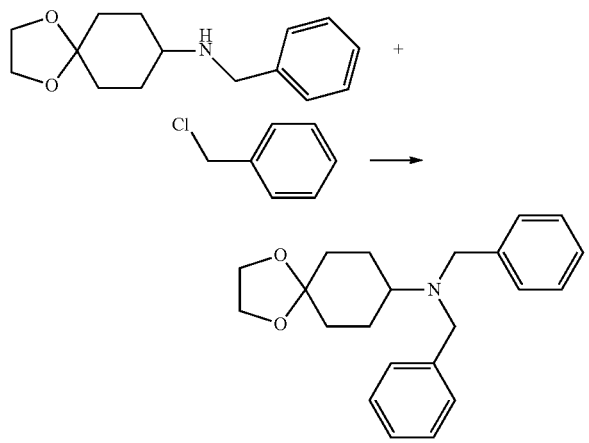

208 g (0.84 mol) product 3a), 114 g (0.9 mol) benzyl chloride, 138 g (1.0 mol) potassium carbonate and 14 g (0.08 mol) potassium iodide were suspended in 400 ml N-methylpyrrolidone and stirred for 24 h at 80° C. Then the mixture was cooled and combined with 5 l water. The crystals precipitated were suction filtered, washed with water and taken up in DCM. The organic phase was dried and evaporated down. The crystals were recrystallised from MeOH, $C_{20}H_{23}NO$ (293.40)

3c)

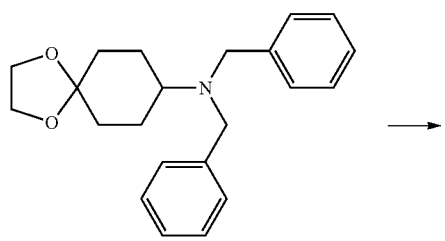

-continued

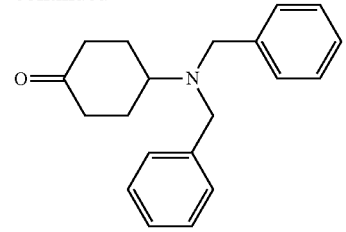

200 g (0.44 mol) product 3c) were suspended in 400 ml of water, combined with 100 ml 37% hydrochloric acid and stirred for 2 h at 60° C. Then the solution was cooled and made alkaline with 200 g (1.45 mol) potassium carbonate. The precipitated crystals were suction filtered and washed with water. The crystals were then dissolved in DCM, the organic solvent was dried and evaporated down. The residue was crystallised from petroleum ether.

$C_{20}H_{23}NO$ (293.40)

$[M+H]^+=294$

3d)

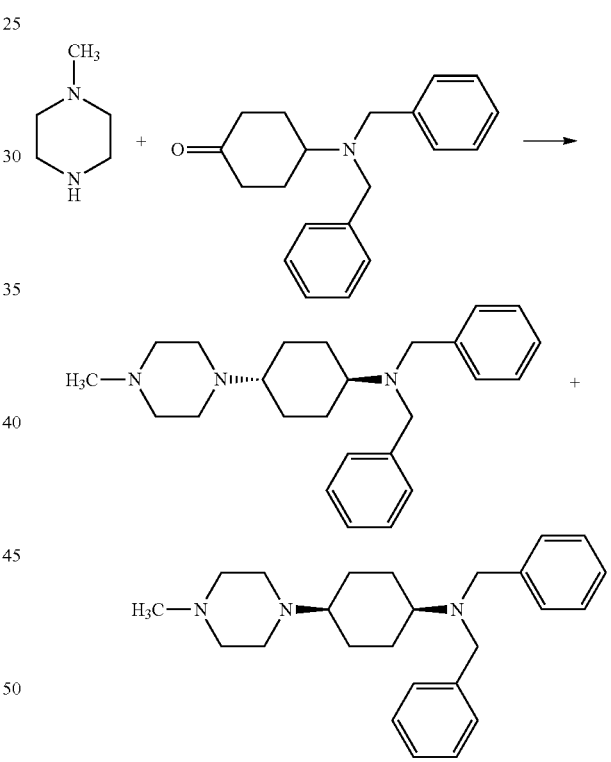

1 ml (9.02 mmol) 1-methylpiperazine and 2.65 g (9.02 mmol) product 3c) were dissolved in 40 ml THF and stirred for 1 h at 50° C. Then at RT 2.87 g (13.52 mmol) sodium triacetoxyborohydride were added and then the mixture was stirred for 2 h at RT. The mixture was then combined with approx. 150 ml DCM, extracted with $NaHCO_3$ solution and extracted three times more with DCM. The organic phase was dried and evaporated down. The residue was purified by preparative HPLC (method 10).

$C_{25}H_{35}N_3$ (377.57)

$[M+H]^+=378$ analytical HPLC (method 3): retention time=0.68 min

3e)

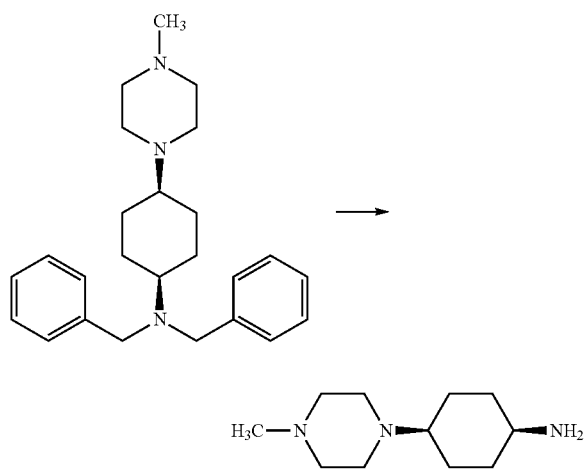

644 mg (1.063 mmol) product 3d) (cis-isomer) were dissolved in 25 ml MeOH and combined with 150 mg of palladium/C catalyst. The reaction mixture was shaken for 5 h at RT and 50 psi in a hydrogen atmosphere. Then the catalyst was filtered off and the filtrate was evaporated down.

$C_{11}H_{23}N_3X_2C_2HF_3O_2$ (425.37)

[M+H]$^+$=198

3f)

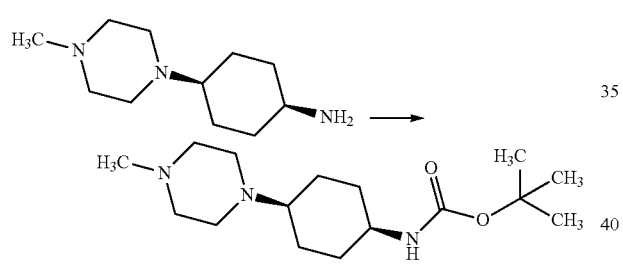

384 mg (0.9 mmol) product 3e) and 0.63 ml (4.51 mmol) TEA were dissolved in 5 ml DMF and combined with 223.4 mg di-tert-butyl-dicarbonate. The reaction mixture was stirred overnight. Then the solvent was evaporated off in vacuo and the residue was purified by preparative HPLC (method 11).

$C_{16}H_{31}N_3O_2$ (297.44)

[M+H]$^+$=298 analytical HPLC (method 3): retention time=0.29 min

3g)

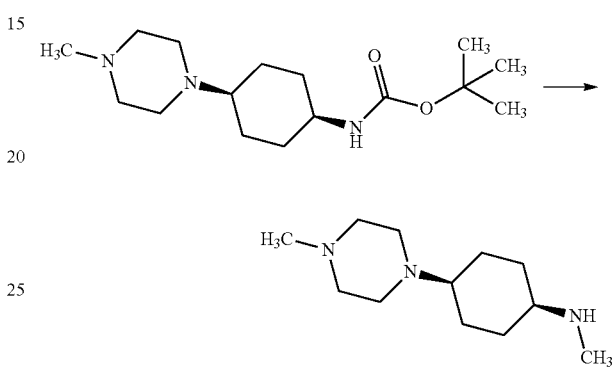

160 mg of product 3f), dissolved in 10 ml THF, were slowly added dropwise to 1.61 ml (1.61 mmol) of a 1M lithium aluminium hydride solution in THF at RT under a nitrogen atmosphere and then stirred for 3.5 h at 75° C. Then the cooled solution was stirred with a little water, combined with 4 ml 1M NaOH and filtered. The solvent was evaporated off.

$C_{12}H_{25}N_3$ (211.35)

[M+H]$^+$=212 analytical HPLC (method 3): retention time=0.30 min

3h)

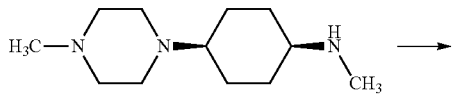

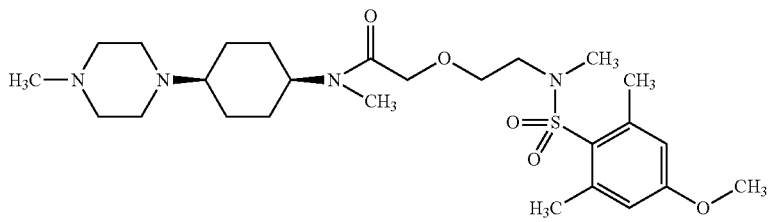

Analogously to Example 1g) the title compound was prepared from product 1d) and product 3g).

$C_{26}H_{44}N_4O_5S \times 2C_2HF_3O_2$ (752.76)

[M+H]+=525 analytical HPLC (method 3): retention time=1.41 min

Example 4

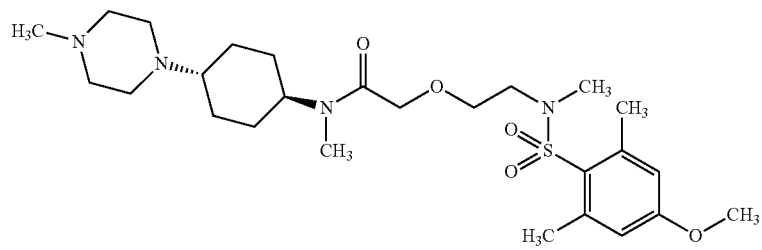

4a)

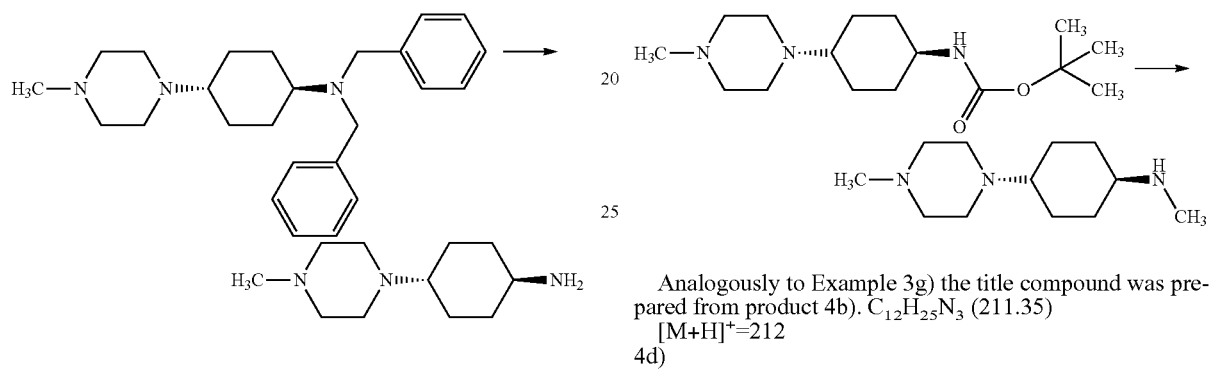

Analogously to Example 3e) the title compound was prepared from product 3d) (trans-isomer).
C₁₁H₂₃N₃×2C₂HF₃O₂ (425.37)
[M+H]⁺=198

4b)

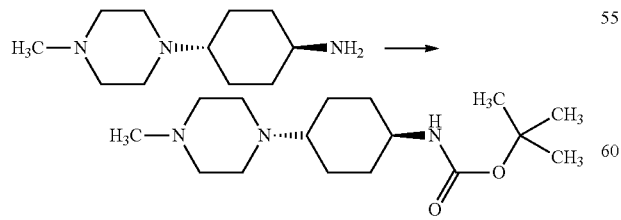

Analogously to Example 3f) the title compound was prepared from product 4a). C₁₆H₃₁N₃O₂ (297.44)
[M+H]⁺=298

4c)

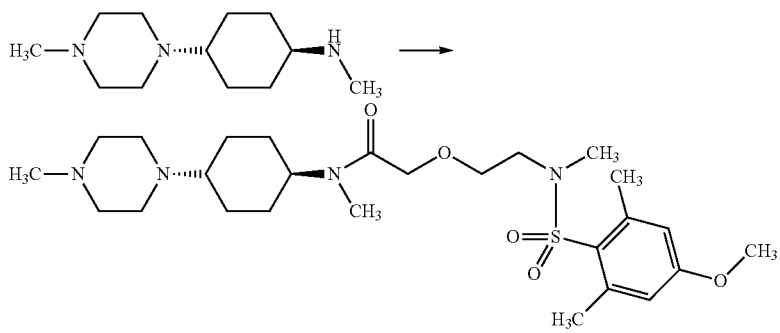

Analogously to Example 3g) the title compound was prepared from product 4b). C₁₂H₂₅N₃ (211.35)
[M+H]⁺=212

4d)

Analogously to Example 1g) the title compound was prepared from product 1d) and product 4c).
C₂₆H₄₄N₄O₅S (524.72)
[M+H]+=525
analytical HPLC (method 3): retention time=1.32 min

Example 5

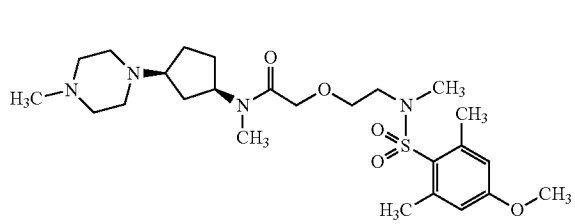

5a)

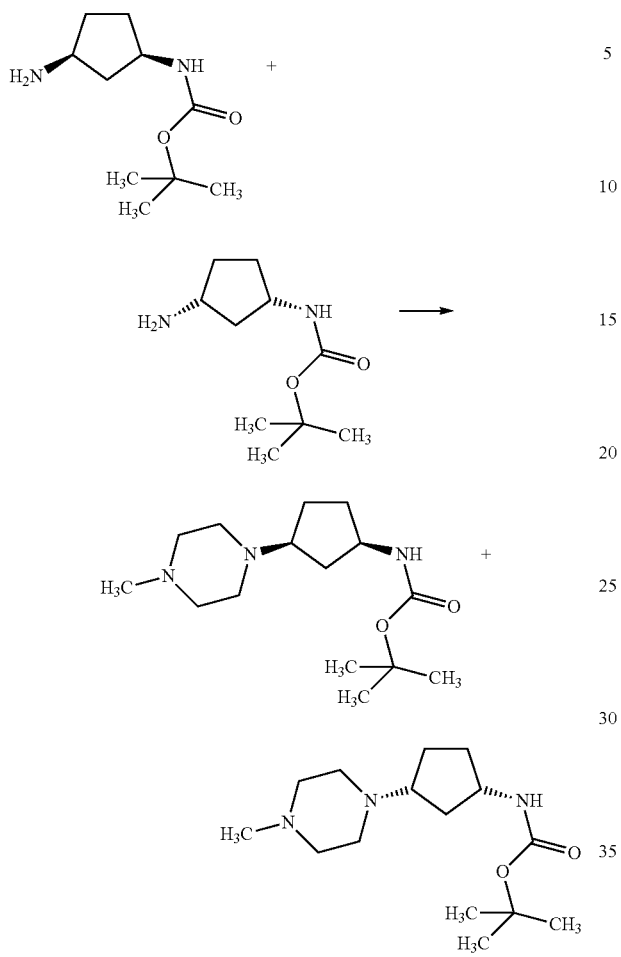

0.5 g (2.5 mmol) tert-butyl 3-amino-cyclopentyl-carbamate (racemic cis), 1.73 g (12.5 mmol) potassium carbonate and 0.01 g potassium iodide were suspended in 20 ml acetonitrile. Then 0.48 g (2.5 mmol) bis-(2-chloro-ethyl)-methylamine-hydrochloride was added and the mixture was refluxed for 4 h. After the reaction mixture had cooled, it was diluted with DCM and extracted with 1 M HCl. The organic phase was dried on sodium sulphate and concentrated by rotary evaporation. The residue was purified by preparative HPLC (method 8).

$C_{15}H_{29}N_3O_2$ (283.41)

$[M+H]^+ = 201$

5b)

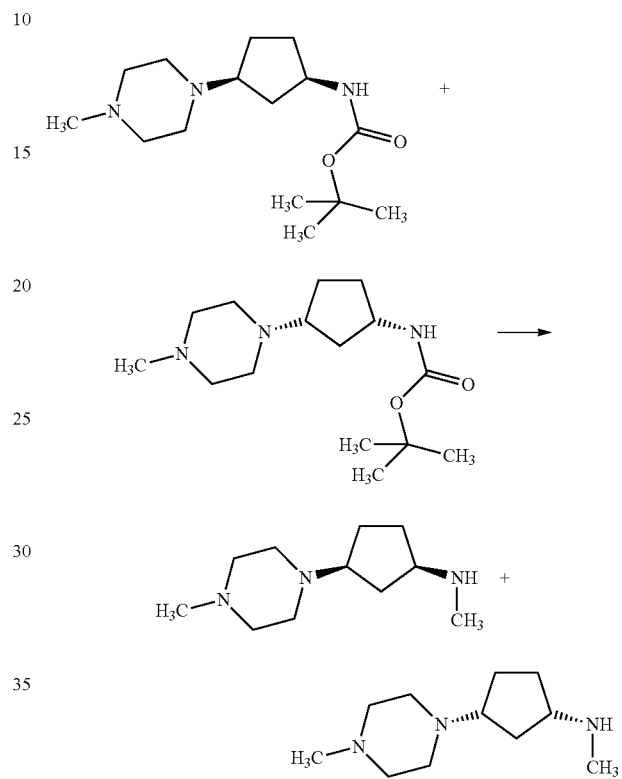

Analogously to Example 3g) the title compound was prepared from product 5a).

$C_{11}H_{23}N_3$ (197.32)

$[M+H]^+ = 198$

5c)

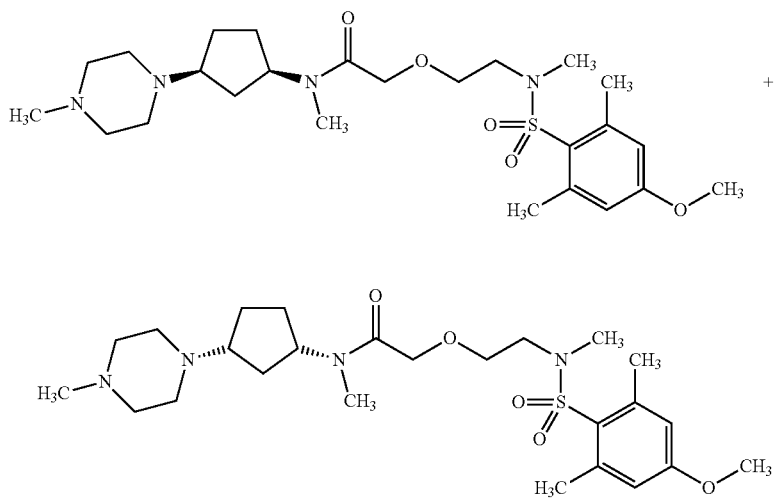

Analogously to Example 1g) the title compound was prepared from product 5b) and product 1d) as a racemic mixture of the two cis-isomers.

$C_{25}H_{42}N_4O_5S \times C_2HF_3O_2$ (624.71)
$[M+H]^+=511$
analytical HPLC (method 3): retention time=1.43 min

Example 6

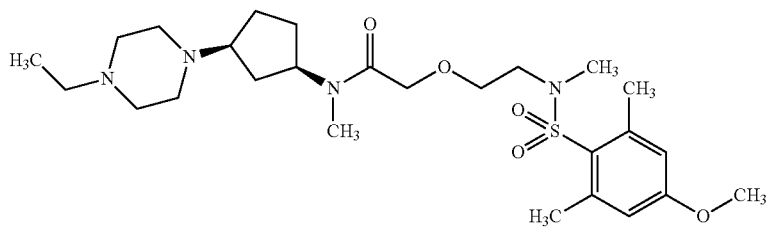 [SMILES: CCN1CCN([C@H]2CC[C@@H](N(C)C(=O)COCCN(C)S(=O)(=O)c3c(C)cc(OC)cc3C)C2)CC1]

6a)

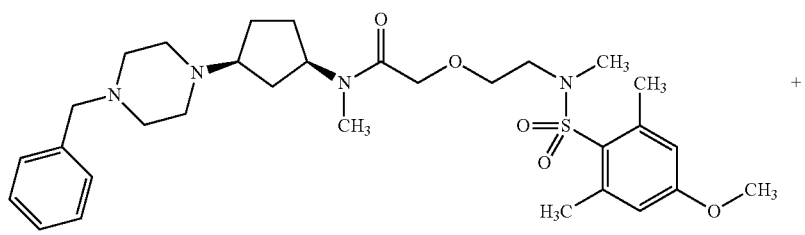

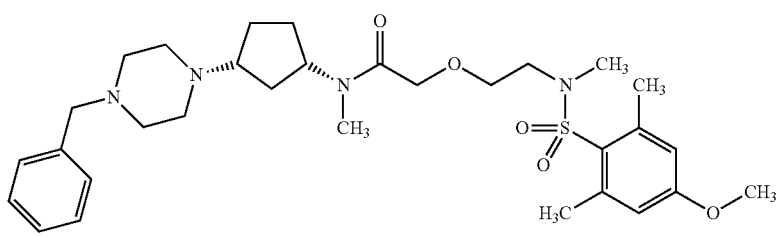

The title compound was prepared analogously to Example 1g) as a racemic mixture of the cis-isomers.
$C_{31}H_{46}N_4O_5S$ (586.79)
$[M+H]^+=587$ 6b)

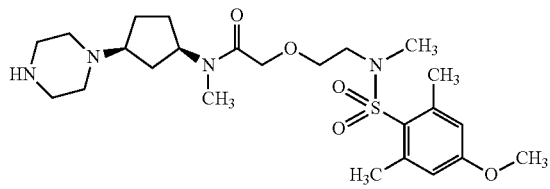

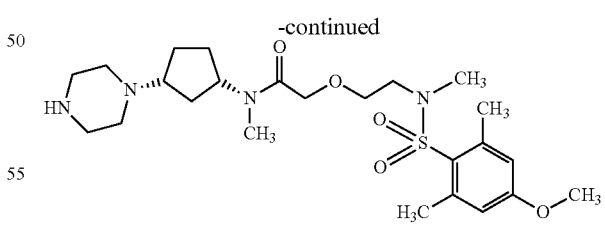

156 mg (0.266 mmol) product 6c) were dissolved in 5 ml MeOH and combined with 50 mg palladium/C catalyst. The reaction mixture was shaken overnight at RT and at 50 psi in a hydrogen atmosphere. Then the catalyst was filtered off and the filtrate was evaporated down. In this way the title compound was obtained as a racemic mixture of the cis-isomers.
$C_{24}H_{40}N_4O_5S$ (496.66)
analytical HPLC (method 3): retention time=1.39 min 6c)

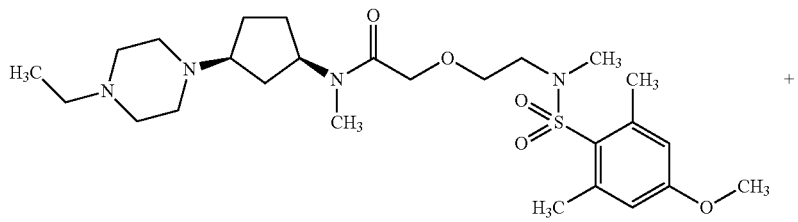

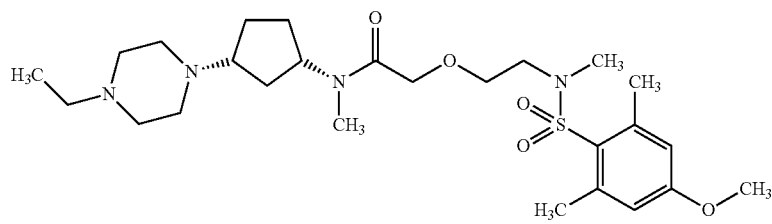

75 mg (0.15 mmol) product 6b) were dissolved in 1 ml acetonitrile and combined with 0.054 ml (0.39 mmol) TEA. The reaction mixture was stirred for 15 min at RT, then 16.5 mg (0.15 mmol) bromoethane were added dropwise and the mixture was then stirred for 24 h at RT. The mixture was purified by preparative HPLC (method 8). In this way the title compound was obtained as a racemic mixture of the cis-isomers.

$C_{26}H_{44}N_4O_5S \times C_2HF_3O_2$ (638.74)

$[M+H]^+=525$ analytical HPLC (method 3): retention time=1.41 min

6d)

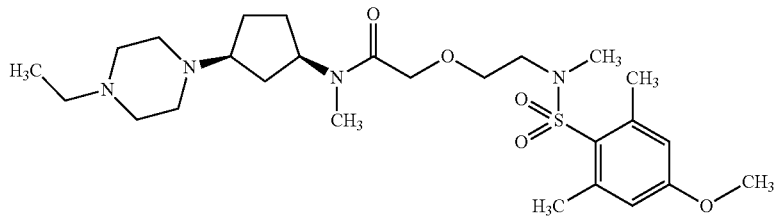 [SMILES: CCN1CCN([C@H]2CC[C@@H](N(C)C(=O)COCCN(C)S(=O)(=O)c3c(C)cc(OC)cc3C)C2)CC1]

Product 6c) (racemic mixture of the cis-isomers) was separated into the enantiomers on the chiral phase according to HPLC method 13. In this way the title compound was obtained as a slowly eluting enantiomer.

$C_{26}H_{44}N_4O_5S \times C_2HF_3O_2$ (638.74)

$[M+H]^+=525$ analytical HPLC (method 3): retention time=17.92 min

Example 7

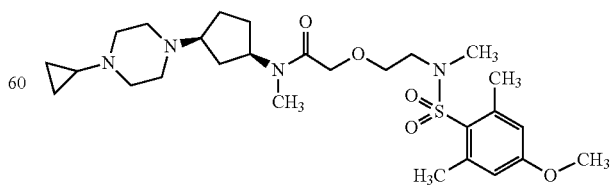

The title compound may be prepared analogously to Example 5.

Example 8
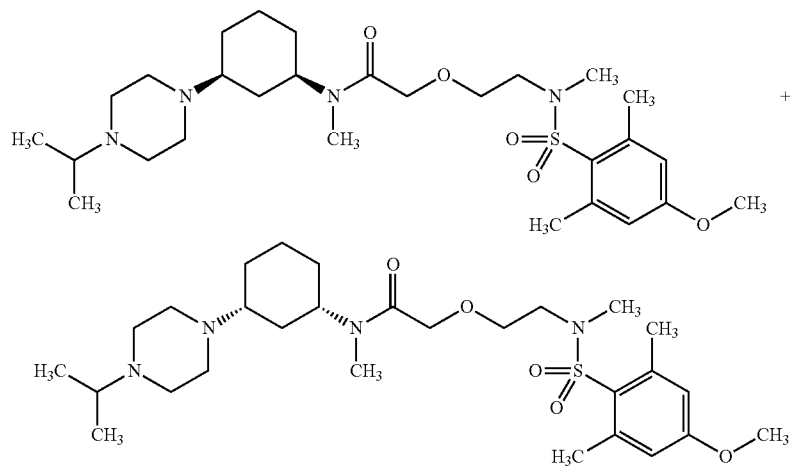
8a)
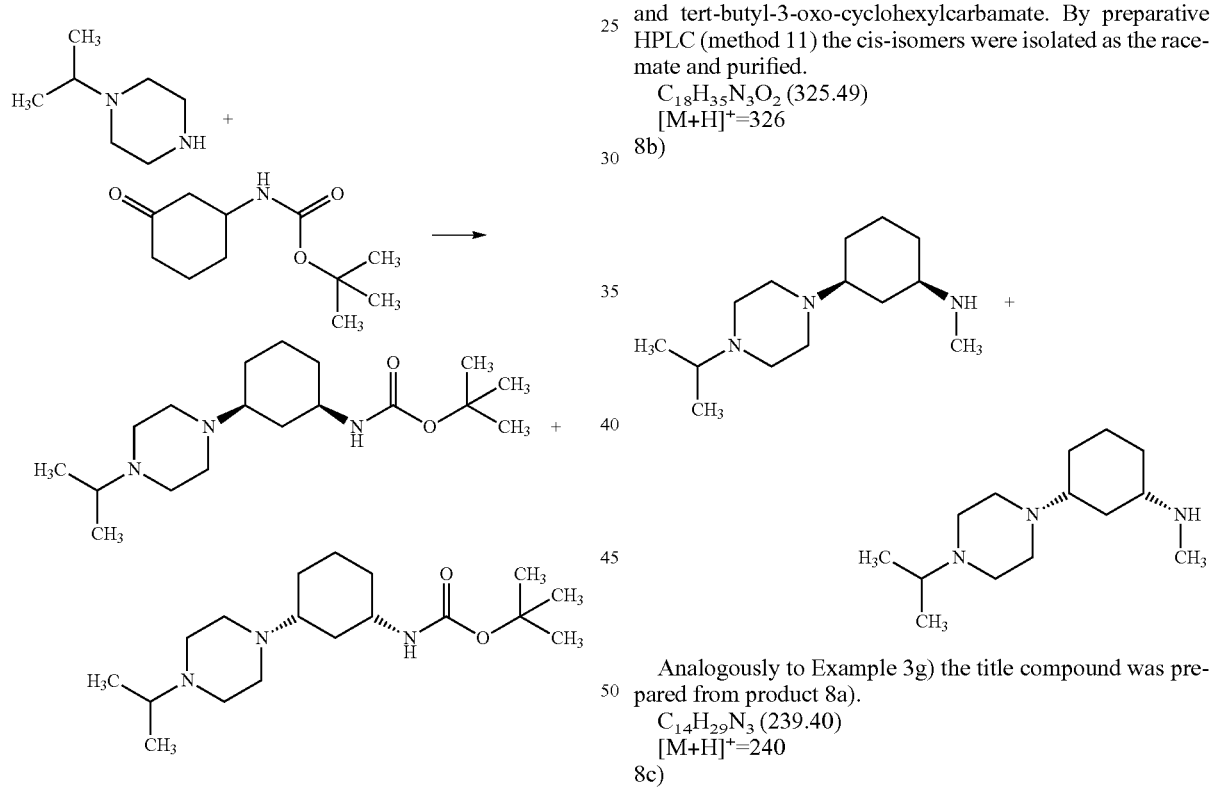
Analogously to Example 1e) the title compound was prepared as a diastereomeric mixture of 1-isopropylpiperazine and tert-butyl-3-oxo-cyclohexylcarbamate. By preparative HPLC (method 11) the cis-isomers were isolated as the racemate and purified.
$C_{18}H_{35}N_3O_2$ (325.49)
$[M+H]^+=326$
8b)
Analogously to Example 3g) the title compound was prepared from product 8a).
$C_{14}H_{29}N_3$ (239.40)
$[M+H]^+=240$
8c)
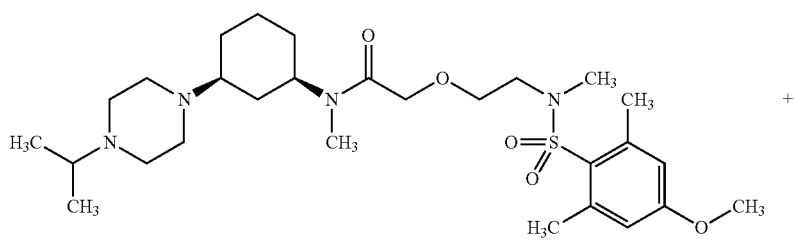

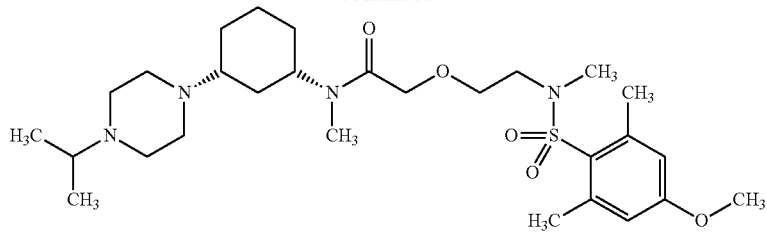

Analogously to Example 1g) the title compound was prepared as a mixture of the cis-isomers of product 8b) and product 1d).

$C_{28}H_{48}N_4O_5S \times C_2HF_3O_2$ (666.79)

$[M+H]^+$=553 analytical HPLC (method 3): retention time=1.44 min

Example 9

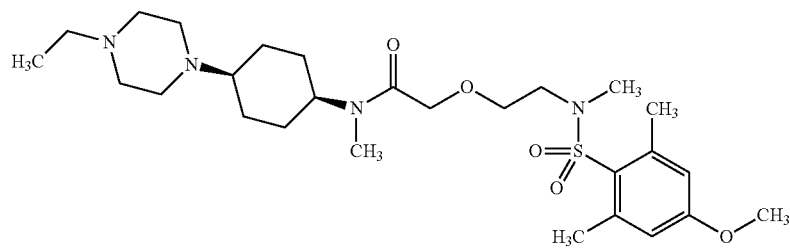 [SMILES: CCN1CCN([C@H]2CC[C@@H](N(C)C(=O)COCCN(C)S(=O)(=O)c3c(C)cc(OC)cc3C)CC2)CC1]

9a)

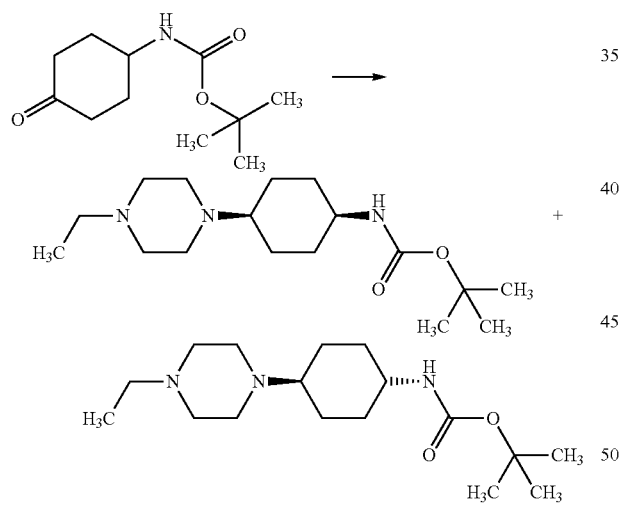

0.3 g (1.41 mmol) N-4-BOC-aminocyclohexanone and 0.18 ml (1.41 mmol) N-ethylpiperazine were placed in 5 ml THF and combined with 0.08 ml (1.41 mmol) glacial acetic acid. After approx. 30 minutes, 0.6 g (2.81 mmol) sodium triacetoxyborohydride were added and the mixture was stirred overnight at RT. Then the mixture was diluted with water and evaporated down. The residue was triturated with acetonitrile and separated from the precipitate by suction filtering. The filtrate was evaporated down.

$C_{17}H_{33}N_3O_2$ (311.46)

$[M+H]^+$=312 analytical HPLC (method 3): retention time=0.45 min

9b)

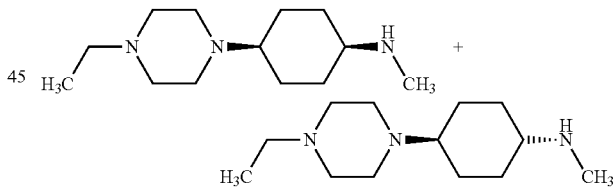

Analogously to Example 3g) the title compound was prepared as a mixture of cis/trans-isomers from product 9a).

$C_{13}H_{27}N_3$ (225.37)

$[M+H]^+$=226

9c)

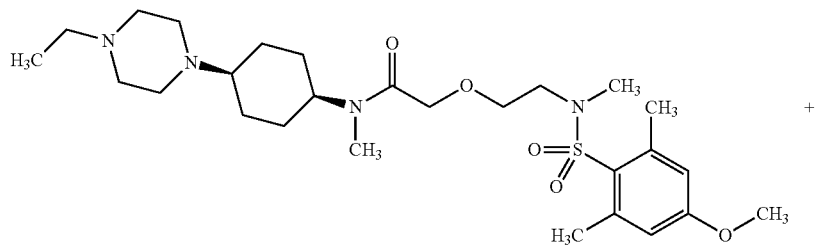

-continued

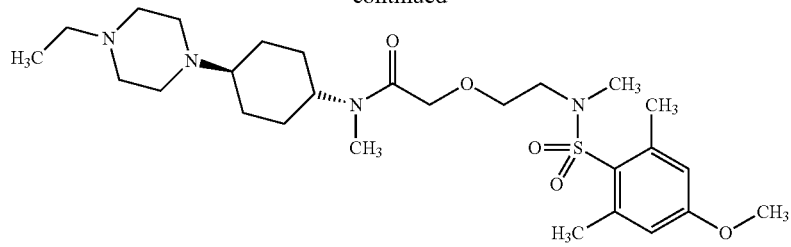

Analogously to Example 1g) the title compound was prepared from product 9b) and product 1d) as a mixture of cis/trans isomers.

9d)

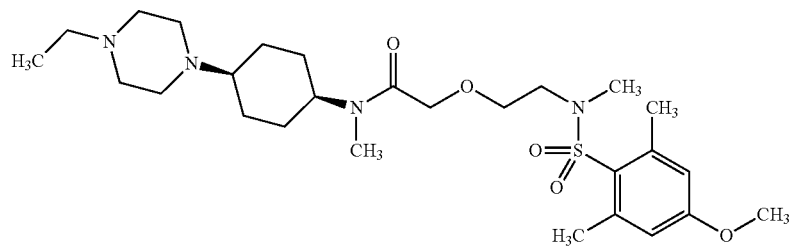 [SMILES: CCN1CCN([C@H]2CC[C@@H](N(C)C(=O)COCCN(C)S(=O)(=O)c3c(C)cc(OC)cc3C)CC2)CC1]

The title compound was separated off from the mixture 9c) by preparative HPLC (method 9).
$C_{27}H_{46}N_4O_5S \times C_2HF_3O_2$ (652.77) cis-product
analytical HPLC (method 3): retention time=1.43 min Example 10

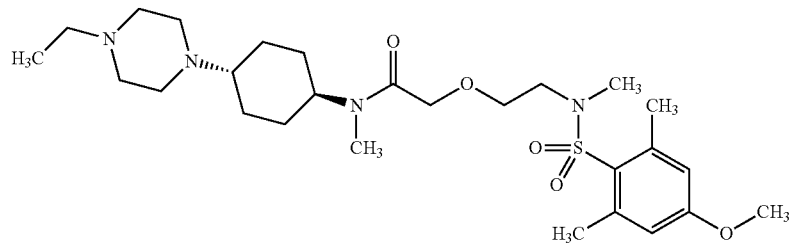 [SMILES: CCN1CCN([C@H]2CC[C@H](N(C)C(=O)COCCN(C)S(=O)(=O)c3c(C)cc(OC)cc3C)CC2)CC1]

The title compound was separated off from the mixture 9c) by preparative HPLC (method 9).
$C_{27}H_{46}N_4O_5S \times C_2HF_3O_2$ (652.77) trans-product
analytical HPLC (method 3): retention time=1.33 min Example 11

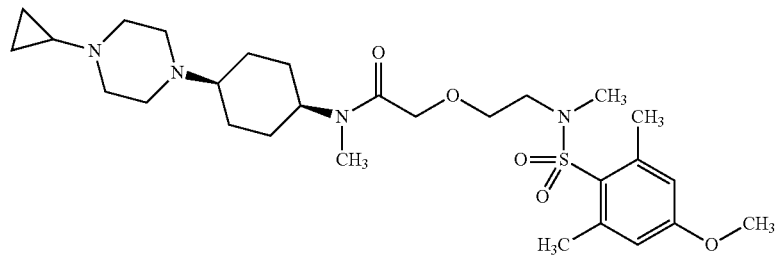 [SMILES: COc1cc(C)c(S(=O)(=O)N(C)CCOCC(=O)N(C)[C@H]2CC[C@@H](N3CCN(C4CC4)CC3)CC2)c(C)c1]

11a)

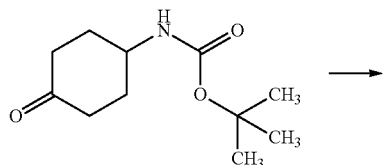

Analogously to Example 9a) the title compound was prepared from N-4-BOC-aminocyclohexanone and N-cyclopropylpiperazine as a mixture of cis/trans isomers.

$C_{18}H_{33}N_3O_2$ (323.47)

[M+H]$^+$=324 analytical HPLC (method 3): retention time=1.08 min

11b)

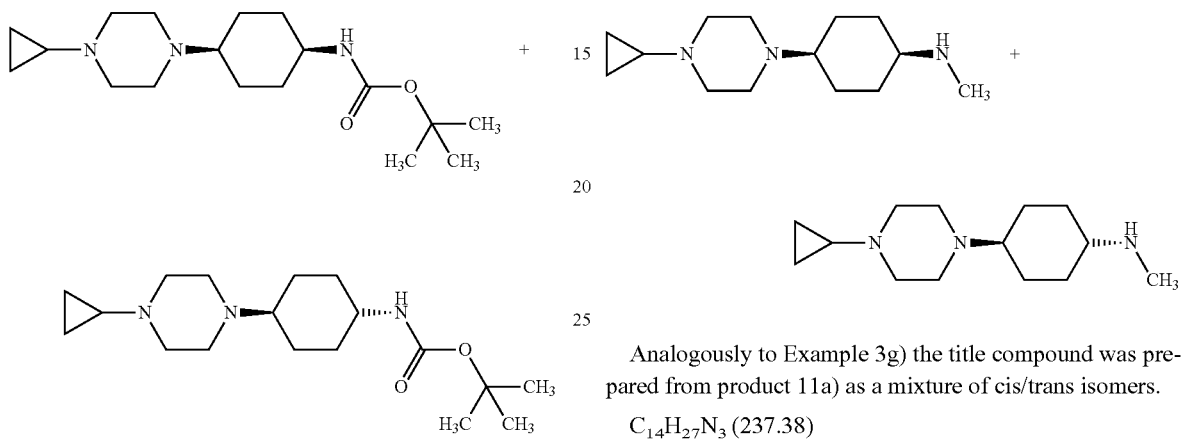

Analogously to Example 3g) the title compound was prepared from product 11a) as a mixture of cis/trans isomers.

$C_{14}H_{27}N_3$ (237.38)

11c)

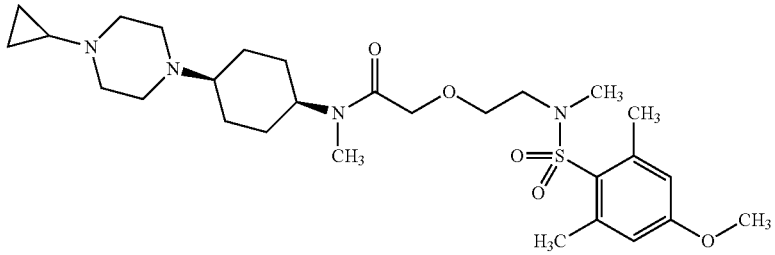 [SMILES: COc1cc(C)c(S(=O)(=O)N(C)CCOCC(=O)N(C)[C@H]2CC[C@@H](N3CCN(C4CC4)CC3)CC2)c(C)c1]

Analogously to Example 1g) the title compound was prepared from product 11b) and product 1d). The cis-isomer was isolated by HPLC (method 9).

$C_{28}H_{46}N_4O_5S$ (550.76)

[M+H]$^+$=551 analytical HPLC (method 3): retention time=1.57 min

Example 12

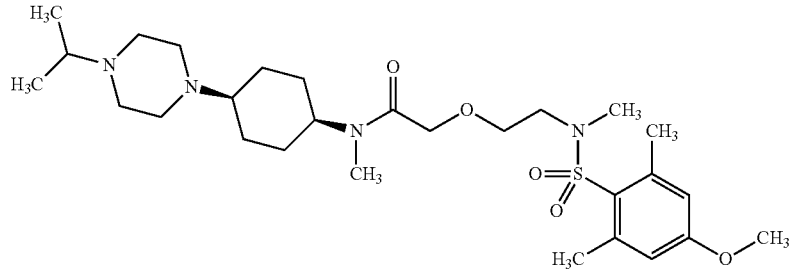 [SMILES: COc1cc(C)c(S(=O)(=O)N(C)CCOCC(=O)N(C)[C@H]2CC[C@@H](N3CCN(C(C)C)CC3)CC2)c(C)c1]

12a)

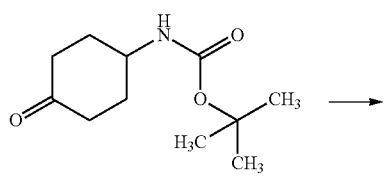

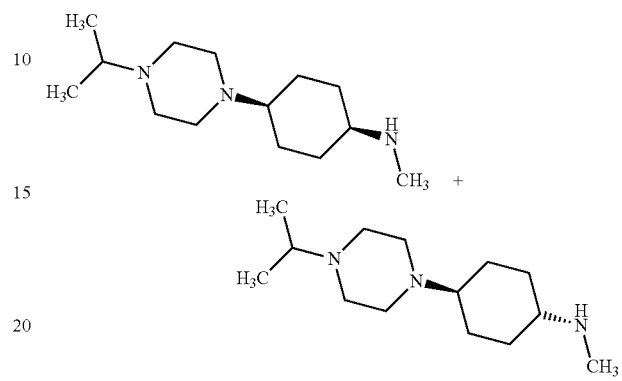

Analogously to Example 9a) the title compound was prepared from N-4-BOC-aminocyclohexanone and N-isopropylpiperazine as a mixture of cis/trans isomers.
C$_{18}$H$_{35}$N$_3$O$_2$ (325.49)
[M+H]$^+$=326

12b)

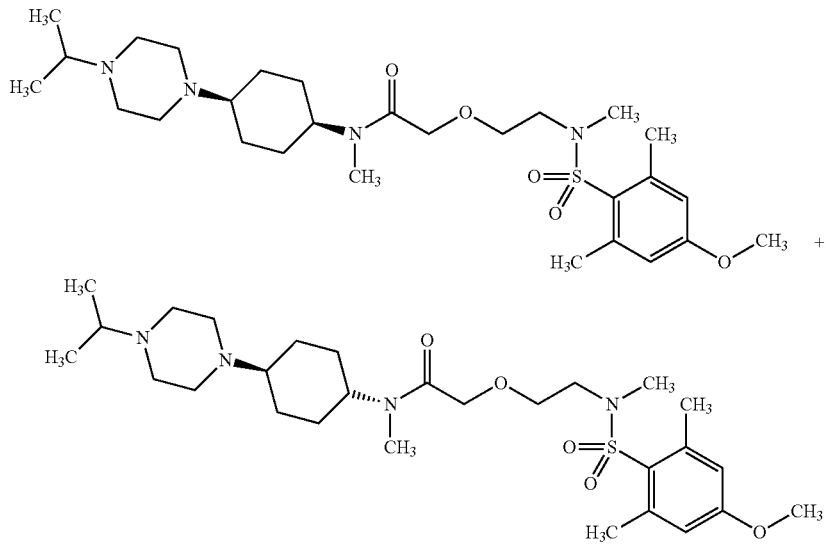

Analogously to Example 3g) the title compound was prepared from product 12a) as a mixture of cis/trans isomers.
C$_{14}$H$_{29}$N$_3$ (239.40)
[M+H]$^+$=240

12c)

Analogously to Example 1g) the title compound was prepared from product 12b) and product 1d) as a mixture of cis/trans isomers.

12d)

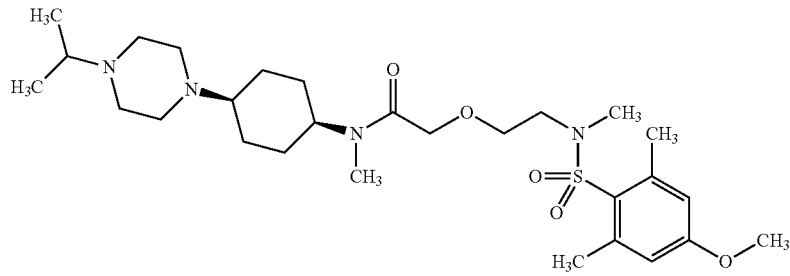 [SMILES: COc1cc(C)c(S(=O)(=O)N(C)CCOCC(=O)N(C)[C@H]2CC[C@@H](N3CCN(C(C)C)CC3)CC2)c(C)c1]

The title compound was isolated from the mixture 12c) by HPLC.

$C_{28}H_{48}N_4O_5S$ (55277) cis-product
$[M+H]^+=553$
analytical HPLC (method 5): retention time=1.87 min Example 13

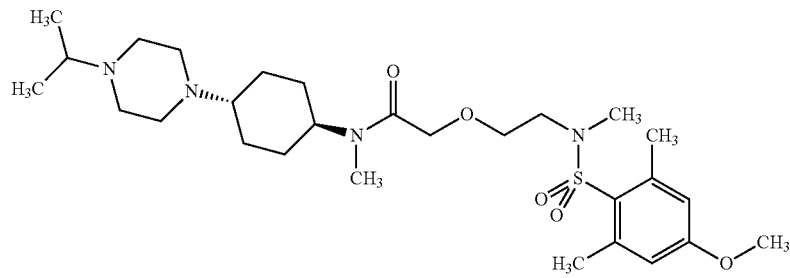 [SMILES: COc1cc(C)c(S(=O)(=O)N(C)CCOCC(=O)N(C)[C@H]2CC[C@H](N3CCN(C(C)C)CC3)CC2)c(C)c1]

The title compound was isolated from the mixture 12c) by HPLC.

$C_{28}H_{48}N_4O_5S$ (552.77) trans-product
$[M+H]^+=553$
analytical HPLC (method 5): retention time=1.66 min Example 14

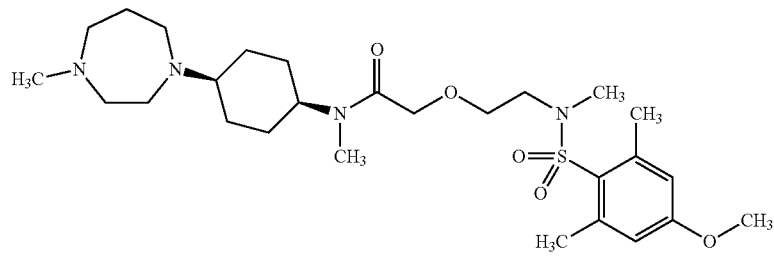

14a)

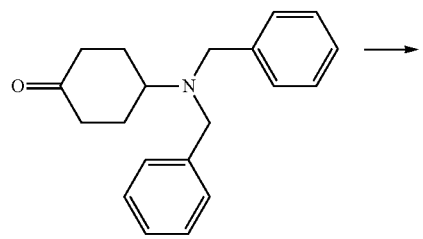

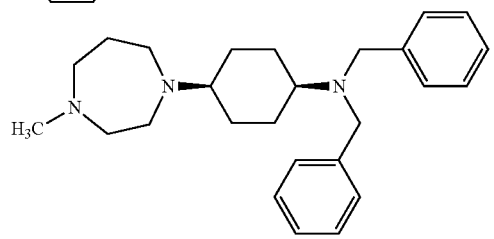

1.1 ml (6.87 mmol) 2-ethylenehexanoic acid were slowly added dropwise to 90 mg (2.38 mmol) sodium borohydride in approx. 3 ml THF and then stirred overnight at RT. The hydride solution thus prepared was slowly added dropwise to a solution of 0.27 ml (2.19 mmol) N-methylhomopiperazine and 642 mg (2.19 mmol) 4-dibenzylamino-cyclohexanone in approx. 27 ml THF and stirred for 2 h at RT. Then the mixture was evaporated down and the title compound was isolated as a cis-isomer from the crude product thus obtained by HPLC (method 11).

$C_{26}H_{37}N_3$ (391.59)
$[M+H]^+=392$
analytical HPLC (method 3): retention time=1.30 min 14b)

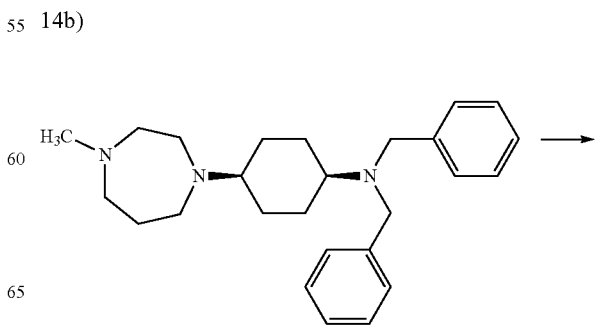

-continued

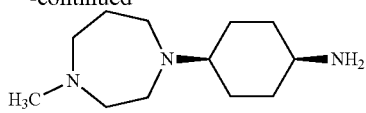

Analogously to Example 3e) the title compound was prepared from product 14a).

$C_{12}H_{25}N_3$ (211.35)
[M+H]$^+$=212

14c)

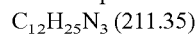

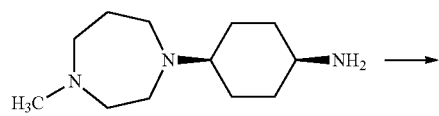

A solution of 135 mg (0.64 mmol) product 14b), 160 mg (0.73 mmol) BOC-anhydride and 0.09 ml (0.65 mmol) TEA in 10 ml of methanol was stirred for 48 h at RT. Then the mixture was evaporated down and the product was isolated by HPLC.

$C_{17}H_{33}N_3O_2$ (311.46)
[M+H]$^+$=312
analytical HPLC (method 4): retention time=1.21 min 14d)

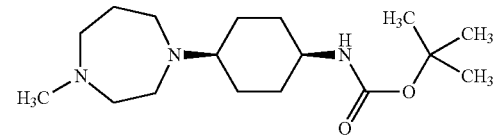

1 ml (2 mmol) 2M lithium aluminium hydride solution in THF was slowly added dropwise to 0.18 g (0.58 mmol) product 14c) in 10 ml THF and then refluxed for 3 h at reflux temperature. Then the mixture was cooled and slowly combined with a little water. The precipitated residue was suction filtered, washed with acetonitrile and the filtrate was evaporated down in vacuo.

$C_{13}H_{27}N_3$ (225.37)
[M+H]$^+$=226

14e)

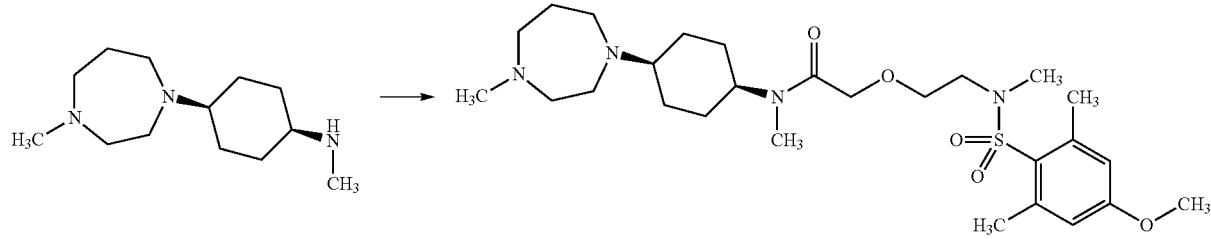

Analogously to Example 1g) the title compound was prepared from product 14d) and product 1d).

$C_{27}H_{46}N_4O_5S \times C_2HF_3O_2$ (652.77)
[M+H]$^+$=539
analytical HPLC (method 3): retention time=1.29 min Example 15

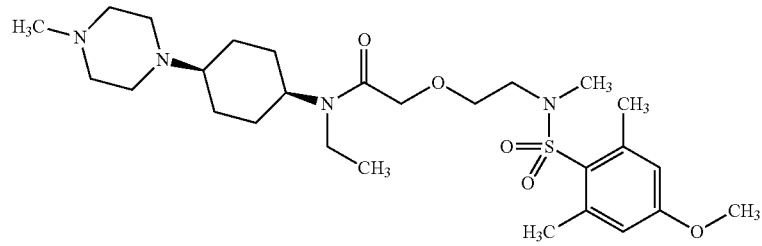

15a)

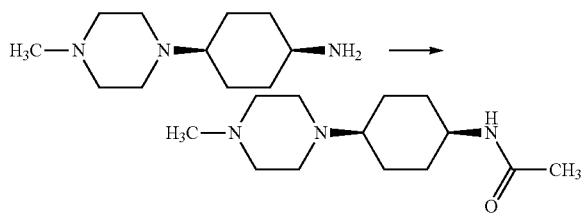

844 mg (1.57 mmol) product 3e), 0.11 ml (1.57 mmol) acetyl chloride and 1.36 ml (7.82 mmol) DIPEA were dissolved in 20 ml DCM and stirred for 2 h at RT. Then the solvent was evaporated down and the residue was purified by preparative HPLC (method 10).

$C_{13}H_{25}N_3O$ (239.36)

$[M+H]^+=240$

15b)

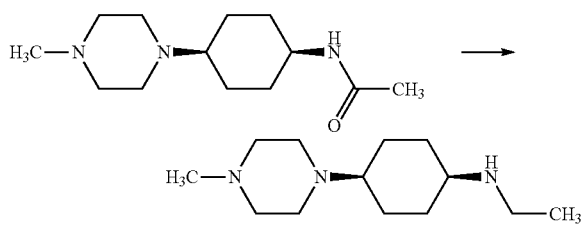

124 mg (0.52 mmol) product 15a), dissolved in 10 ml THF, were slowly added dropwise to 0.69 ml (1.4 mmol) of a 2M lithium aluminium hydride solution in THF. The mixture was stirred for 4 h at 75° C. Then the solution was combined with a little water, the precipitate formed was filtered off and the filtrate was evaporated down.

$C_{13}H_{27}N_3$ (225.37)

$[M+H]^+=226$

15c)

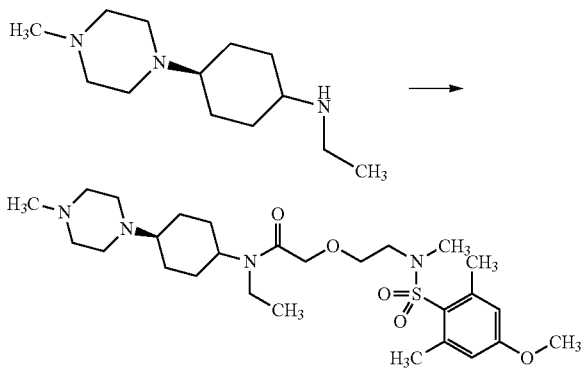

Analogously to Example 1g) the title compound was prepared from product 1d) and product 15g).

$C_{27}H_{46}N_4O_5S$ (538.74)

$[M+H]^+=539$ analytical HPLC (method 3): retention time=1.47 min

Example 16

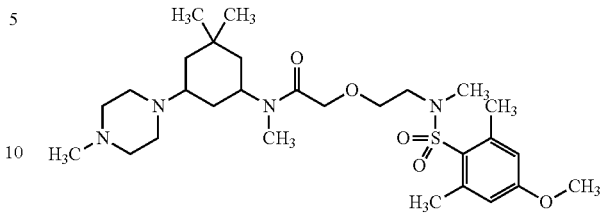

16a)

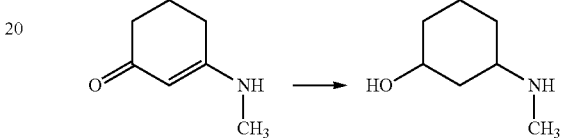

1 g (6.53 mmol) 5,5-dimethyl-3-(methylamino)-2-cyclohexen-1-one, dissolved in 15 ml EtOH, were combined with 100 mg Raney nickel and hydrogenated for 24 h at RT. Then the mixture was heated to 50° C. and hydrogenated for a further 24 h. Then palladium/charcoal was added and the mixture was hydrogenated for a further 24 h at RT. Finally 3 ml of 6 M NaOH were added and the mixture was again hydrogenated for 24 h. Then the catalyst was suction filtered and the filtrate was evaporated down. The crude product thus obtained was reacted further without purification.

$C_9H_{17}NO$ (155.24)

analytical HPLC (method 3): retention time=0.61 min

16b)

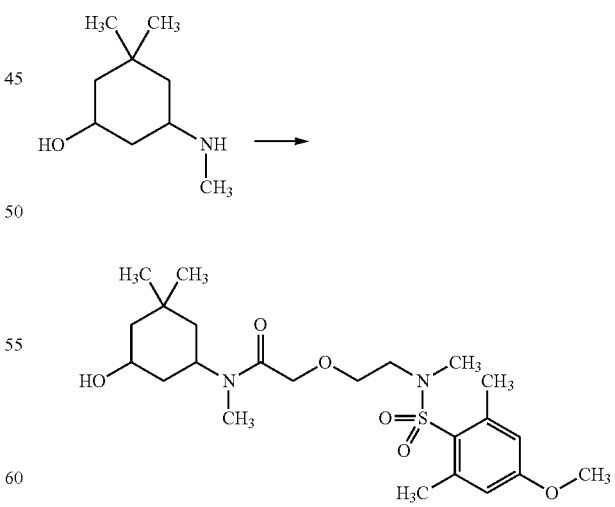

Analogously to Example 1g) the title compound was prepared from product 16a) and product 1d).

$C_{23}H_{38}N_2O_6S$ (470.62)

$[M+H]^+=471$

16c)

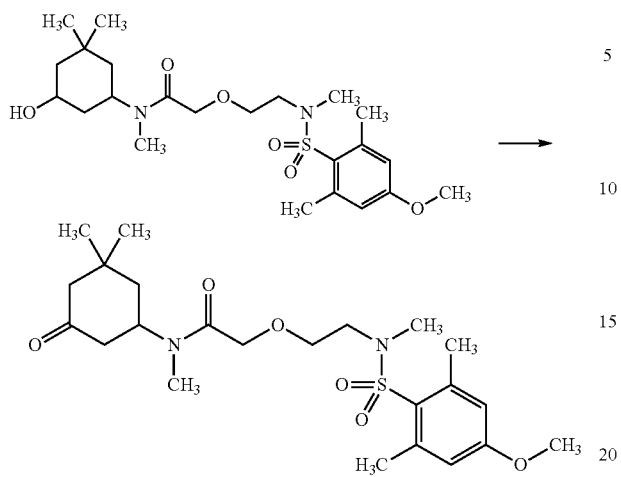

42 mg (0.1 mmol) Dess-Martin-periodinane were added to a solution of 42 mg (0.09 mmol) product 16b) in 5 ml acetonitrile and the mixture was stirred at RT. After oxidation had ended the mixture was combined with a little water and evaporated down. The residue was triturated with DCM and suction filtered to separate off the precipitated solid. The filtrate was evaporated down.

$C_{23}H_{36}N_2O_6S$ (468.61)
analytical HPLC (method 3): retention time=2.22 min 16d)

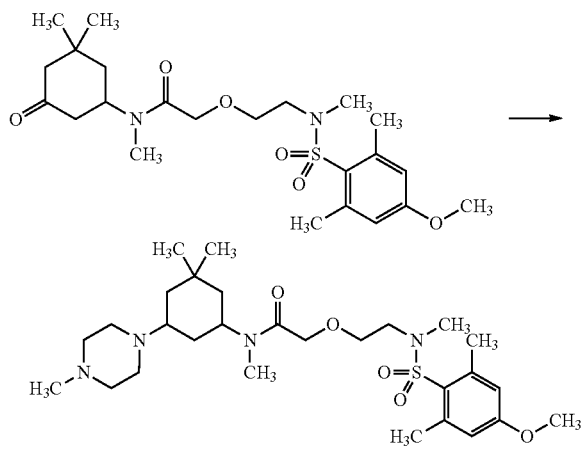

5.25 μl (0.092 mmol) acetic acid were added to a solution of 43 mg (0.092 mmol) product 16c) and 10.2 μl (0.092 mmol) 1-methylpiperazine in 5 ml anhydrous THF and the mixture was stirred for 30 min at RT. Then 58.34 mg (0.28 mmol) sodium triacetoxyborohydride were added and the mixture was stirred for a further 24 h at RT. Then a few drops of 1-methylpiperazine, acetic acid, sodium triacetoxyborohydride were added several times within a week and after 4 days molecular sieve was added. Then the molecular sieve and the precipitated solid were suction filtered, washed with acetonitrile and the filtrate was evaporated down. The residue was extracted with DCM and sodium hydrogen carbonate solution. The organic phase was separated off, dried on magnesium sulphate and concentrated by rotary evaporation. The residue was purified by preparative HPLC (method 9).

$C_{28}H_{48}N_4O_5S$ (552.77)
$[M+H]^+=553$
analytical HPLC (method 3): retention time=1.76 min Example 17

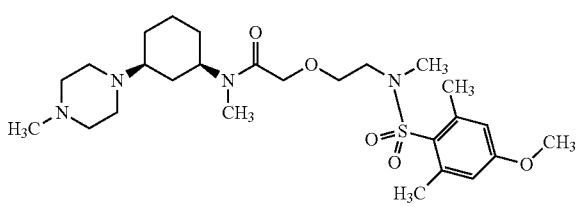

Product 1g) (racemic mixture of the cis-isomers) was separated into the enantiomers on the chiral phase according to HPLC method 13. In this way the title compound was obtained as the fast eluting enantiomer.

$C_{26}H_{44}N_4O_5S$ (524.72
$[M+H]^+=525$
HPLC (method 13): retention time=7.3 min Example 18

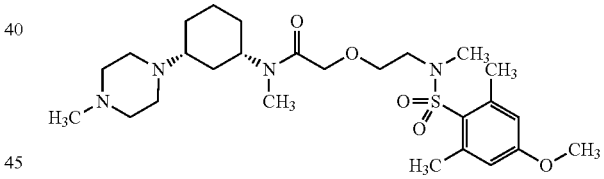

Product 1g) (racemic mixture of the cis-isomers) was separated into the enantiomers on the chiral phase according to HPLC method 13. In this way the title compound was obtained as the slowly eluting enantiomer.

$C_{26}H_{44}N_4O_5S$ (524.72
$[M+H]^+=525$
HPLC (method 13): retention time=9.7 min Example 19

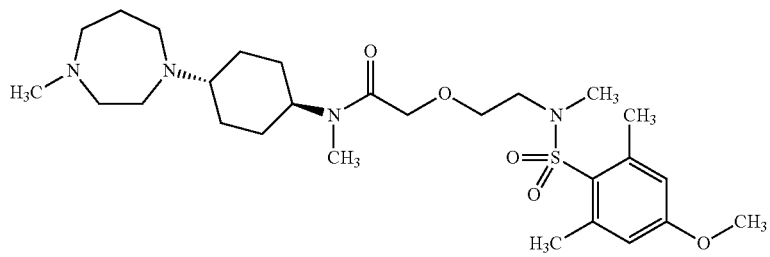

19a)

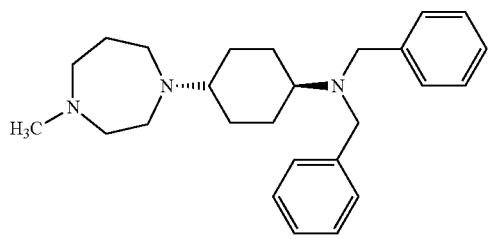

The trans-isomer was isolated from the crude product 14a) by chromatography (preparative HPLC method 11).
$C_{26}H_{37}N_3$ (391.59) trans compound
$[M+H]^+=392$ 19b)

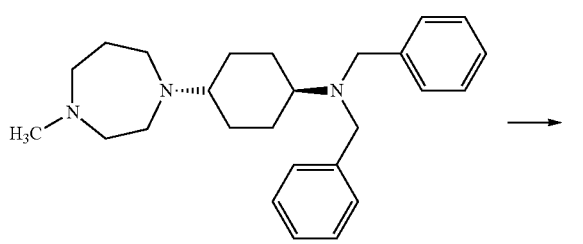

Analogously to Example 3e) the title compound was prepared from product 19a).
$C_{12}H_{25}N_3 \times 3HCl$ (320.73)
$[M+H]^+=212$ 19c)

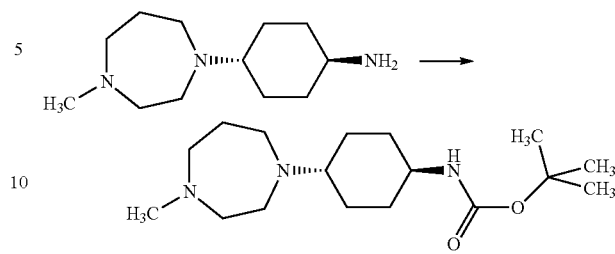

Analogously to Example 14c) the title compound was prepared from product 19b).
$C_{17}H_{33}N_3O_2 \times 3HCl$ (420.85)
$[M+H]^+=312$ 19d)

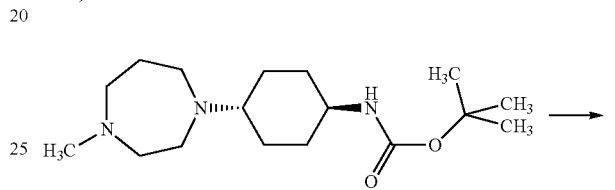

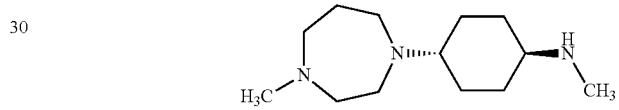

Analogously to Example 14d) the title compound was prepared from product 19c).
$C_{17}H_{33}N_3O_2 \times_3 HCl$ (420.85)
$C_{13}H_{27}N_3$ (225.37)
analytical HPLC (method 3): retention time=0.304 min 19e)

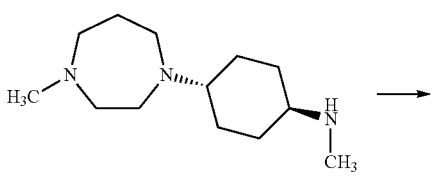

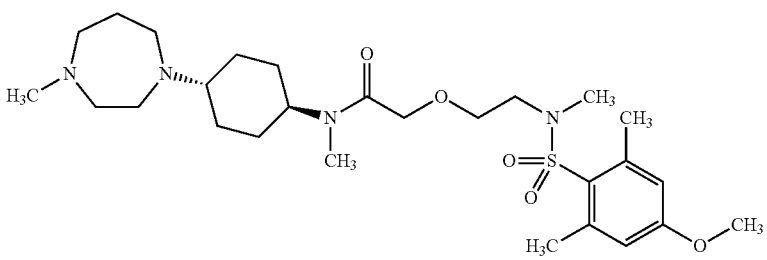

Analogously to Example 1g) the title compound was prepared from product 19d) and product 1d).
$C_{27}H_{46}N_4O_5S \times C_2HF_3O_2$ (652.77)
$[M+H]^+=539$
HPLC (method 3): retention time=1.30 min

Example 20
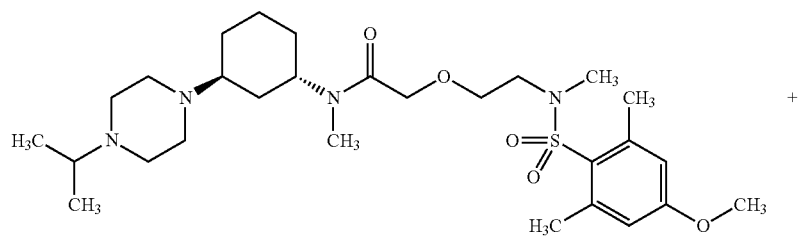
20a)
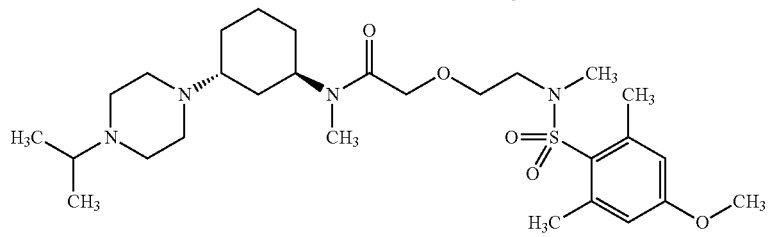
20b)
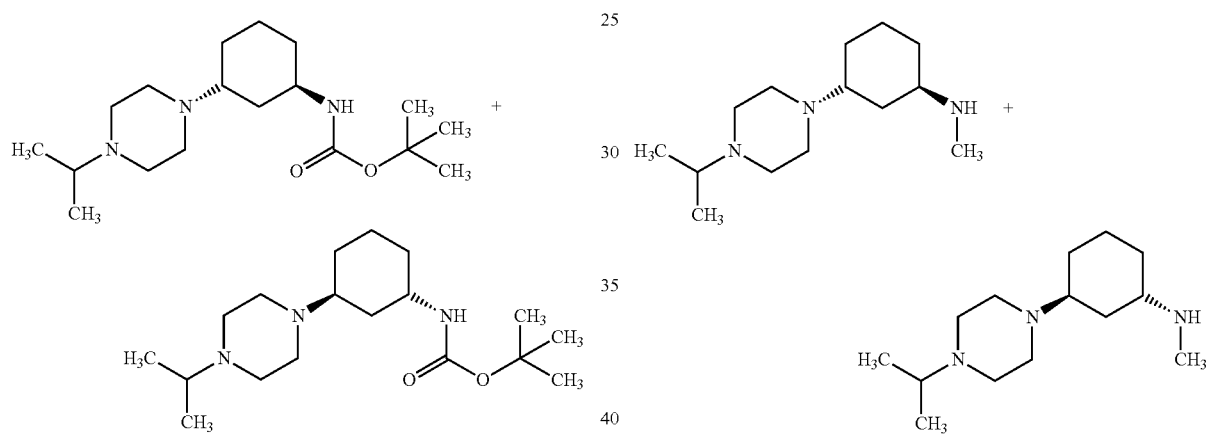
The trans-isomers were isolated from the crude product 8a) as a racemic mixture by preparative HPLC (method 11).
$C_{18}H_{35}N_3O_2$ (325.49) trans-compound
[M+H]$^+$=326
Analogously to Example 3g) the title compound was prepared as a mixture of the trans-isomers from product 20a).
$C_{14}H_{29}N_3$ (239.40)
[M+H]$^+$=240
20c)
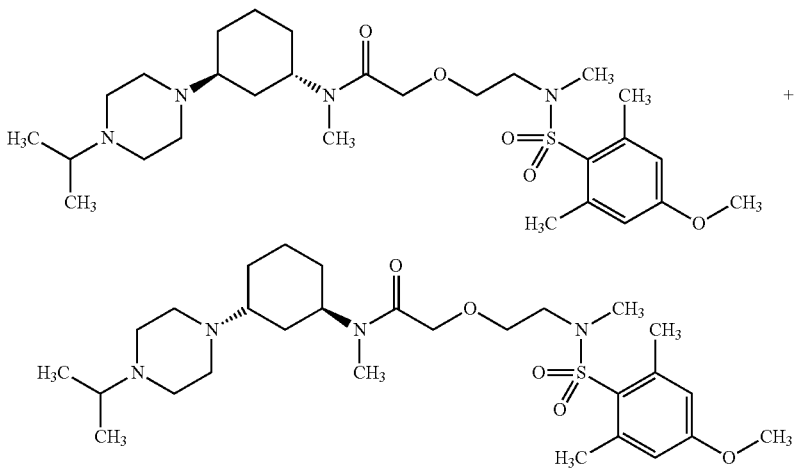

Analogously to Example 1g) the title compound was prepared from product 20b) and product 1d).

$C_{28}H_{48}N_4O_5S \times 2C_2HF_3O_2$ (780.82)

[M+H]$^+$=553 analytical HPLC (method 3): retention time=1.53 min

Example 21

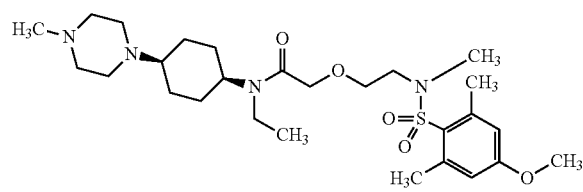

21a)

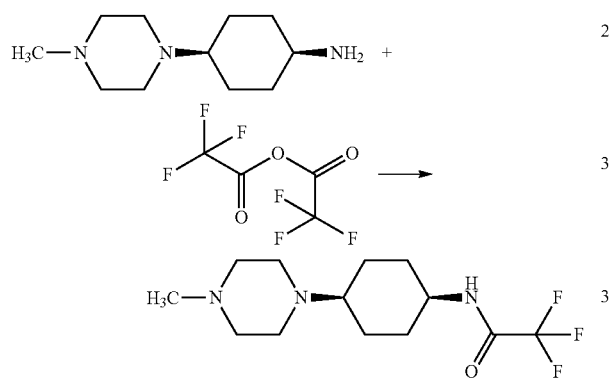

Analogously to Example 15a) the title compound was prepared from product 3e) and trifluoroacetic anhydride.

$C_{13}H_{22}F_3N_3O$ (293.33)

[M+H]$^+$=294 analytical HPLC (method 5): retention time=1.16 min

21b)

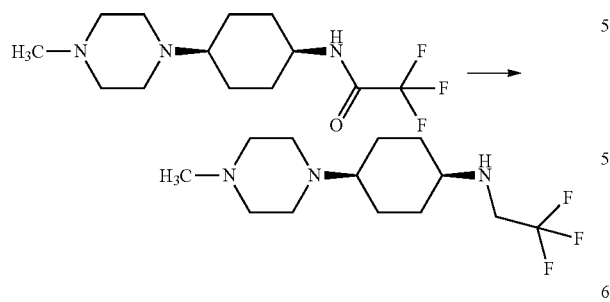

Analogously to Example 15b) the title compound was prepared from product 21a).

$C_{13}H_{24}F_3N_3$ (279.35)

[M+H]$^+$=280 analytical HPLC (method 5): retention time=1.36 min

21c)

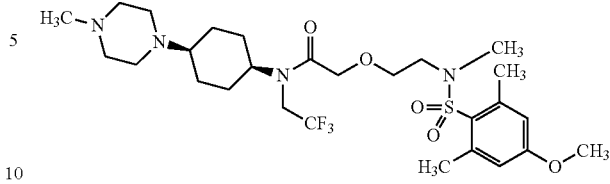

Analogously to Example 15c) the title compound was prepared from product 21b) and product 1d) and purified by HPLC (method 9).

$C_{27}H_{43}F_3N_4O_5S \times C_2HF_3O_2$ (706.74)

[M+H]$^+$=593

Example 22

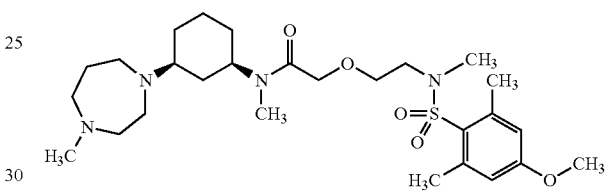

22a)

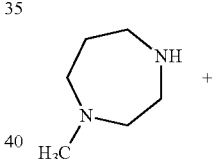

+

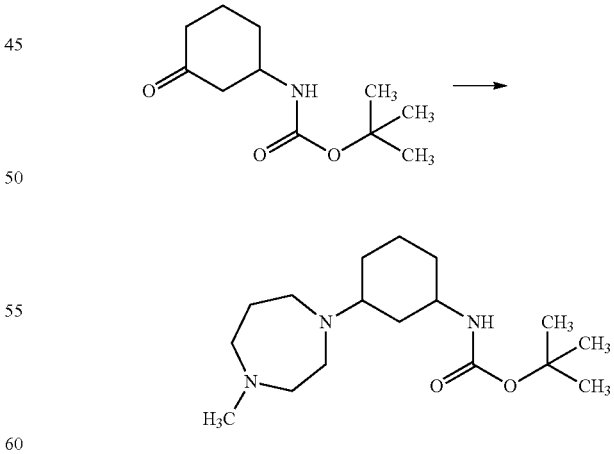

Analogously to Example 1e) the title compound was prepared from N-methyl-homopiperazine and tert-butyl (3-oxo-cyclohexyl)-carbamate as a mixture of diastereomers.

$C_{17}H_{33}N_3O_2$ (311.46)

analytical HPLC (method 3): retention time=0.42 min

22b)

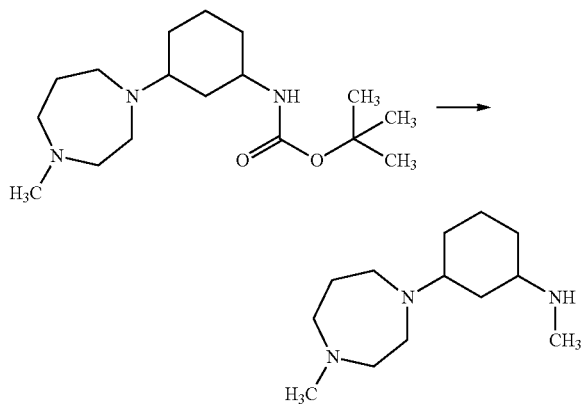

Analogously to Example 1f) the title compound was prepared from product 22a) as a mixture of diastereomers.

$C_{13}H_{27}N_3$ (225.37)

analytical HPLC (method 3): retention time=0.26 min

22c)

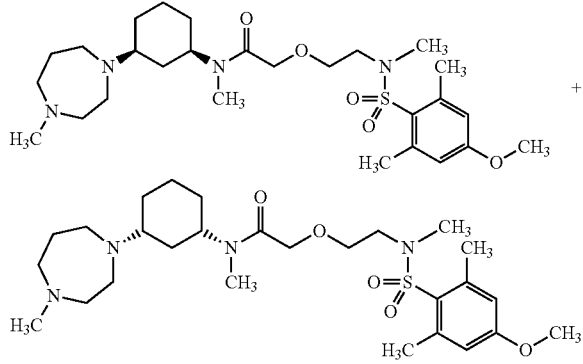

Analogously to Example 1g) the title compound was prepared as a racemic mixture of the cis-isomers.

$C_{27}H_{46}N_4O_5S$ (538.74)

$[M+H]^+$=539

22d)

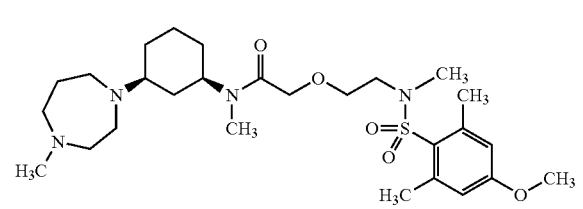

The racemic mixture of Example 22c) was separated into the enantiomers on the chiral phase according to HPLC method 14. In this way the title compound was obtained as a fast eluting enantiomer.

$C_{27}H_{46}N_4O_5S$ (538.74)

$[M+H]^+$=539

HPLC (method 14): retention time=1.31 min

Example 23

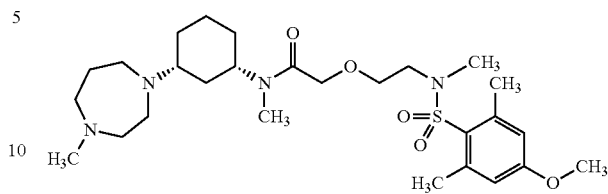

The racemic mixture of Example 22c) was separated into the enantiomers on the chiral phase according to HPLC method 14. In this way the title compound was obtained as a slowly eluting enantiomer.

$C_{27}H_{46}N_4O_5S$ (538.74)

$[M+H]^+$=539

HPLC (method 14): retention time=1.57 min

Example 24

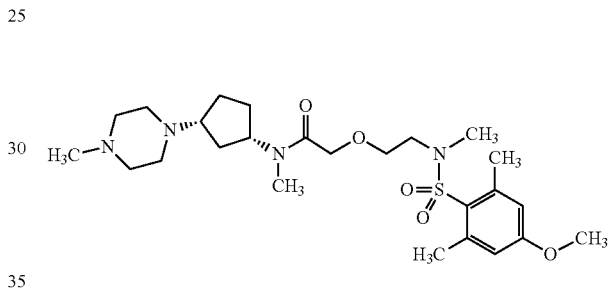

The racemic mixture of the cis-isomers from Example 5c) was separated into the enantiomers on the chiral phase according to HPLC method 13. In this way the title compound was obtained as a slowly eluting enantiomer.

$C_{25}H_{42}N_4O_5S$ (510.69)

$[M+H]^+$=511

HPLC (method 13): retention time=12.37 min

Example 25

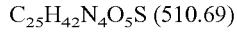

The racemic mixture of the cis-isomers from Example 5c) was separated into the enantiomers on the chiral phase according to HPLC method 13. In this way the title compound was obtained as a fast eluting enantiomer.

$C_{25}H_{42}N_4O_5S$ (510.69)

$[M+H]^+$=511

HPLC (method 13): retention time=6.96 min

Example 26

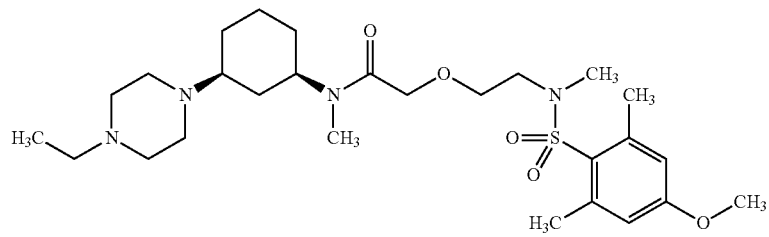 [SMILES: CCN1CCN([C@H]2CCC[C@@H](N(C)C(=O)COCCN(C)S(=O)(=O)c3c(C)cc(OC)cc3C)C2)CC1]

26a)

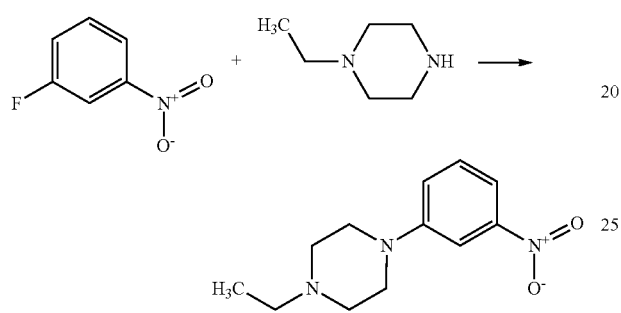

1.0 ml (9.4 mmol) 3-fluoronitrobenzene, 2 g (14.1 mmol) potassium carbonate and 1.2 ml (9.4 mmol) N-ethylpiperazine in 20 ml DMF were refluxed for 48 h at 185° C. Then another 1.2 ml (9.4 mmol) N-ethylpiperazine was added and the mixture was refluxed for a further 30 h. Then the carbonate was filtered off and the filtrate was evaporated down. The residue was purified by preparative HPLC (method 10).

$C_{12}H_{17}N_3O_2$ (235.28)

$[M+H]^+=236$ analytical HPLC (method 3): retention time=0.77 min

26b)

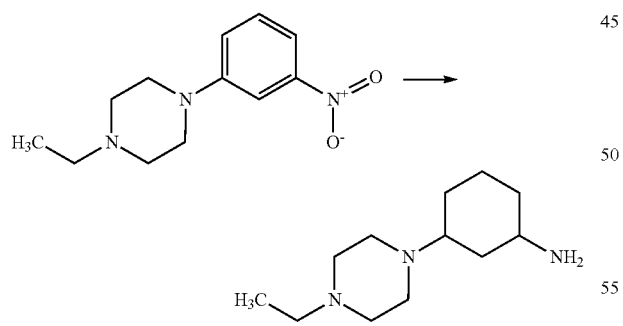

550 mg (2.34 mmol) product 26a) and 300 mg Nishimura-catalyst (Rh/Pt) were suspended in 25 ml MeOH and shaken for 24 h at RT and 5 bar in a hydrogen atmosphere. Then the catalyst was filtered off and the filtrate was evaporated down. In this way the title compound was obtained as a mixture of diastereomers.

$C_{12}H_{25}N_3$ (211.35)

$[M+H]^+=212$ analytical HPLC (method 5): retention time=1.19 min

26c)

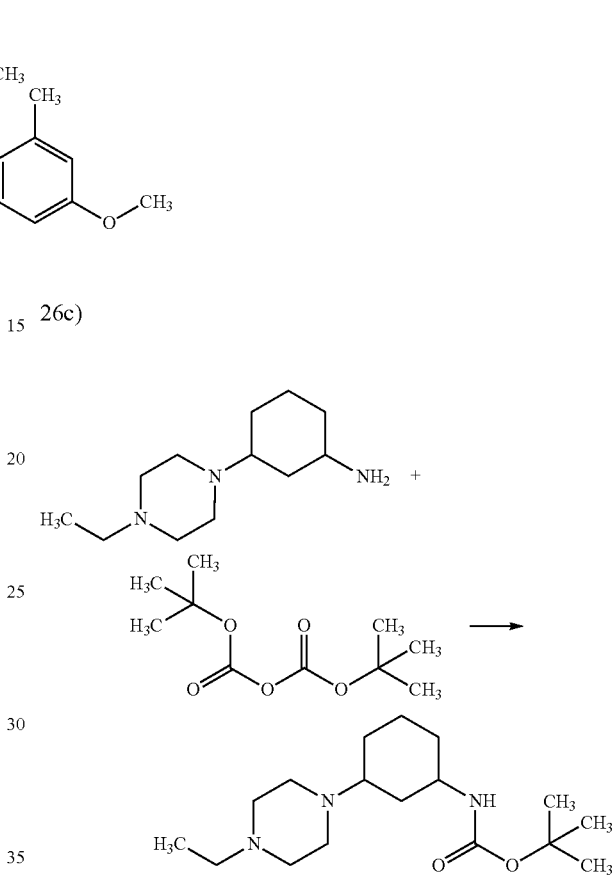

613 mg (2.81 mmol) BOC-anhydride and 0.71 ml (5.15 mmol) TEA were added to a solution of 550 mg (2.34 mmol) product 26a) in 15 ml DCM and the mixture was stirred for 48 h at RT. Then the precipitate formed was suction filtered and washed with DCM. The filtrate was evaporated down and purified by preparative HPLC (method 10). The two products were combined. In this way the title compound was obtained as a mixture of diastereomers.

$C_{17}H_{33}N_3O_2$ (311.46)

$[M+H]^+=312$ analytical HPLC (method 5): retention time=1.50 min

26d)

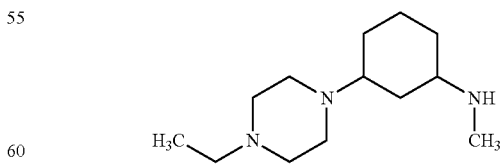

Analogously to Example 14d) the title compound was prepared from 26c) as a mixture of diastereomers.

$C_{13}H_{27}N_3$ (225.37)

$[M+H]^+=225$

26e)

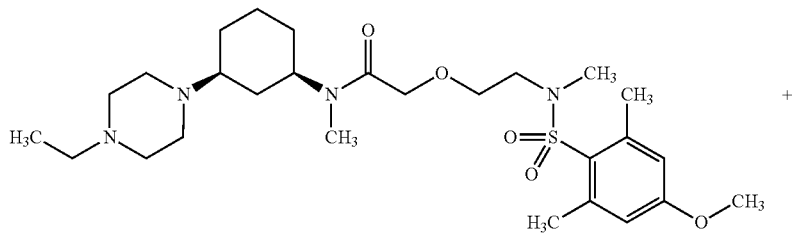

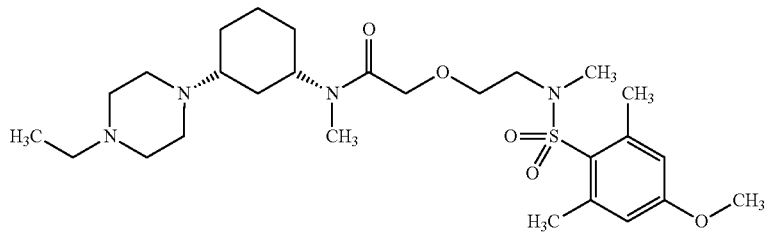

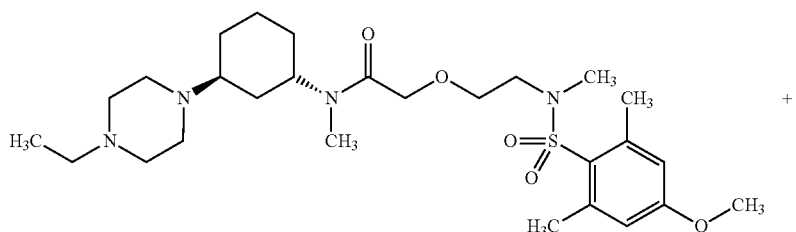

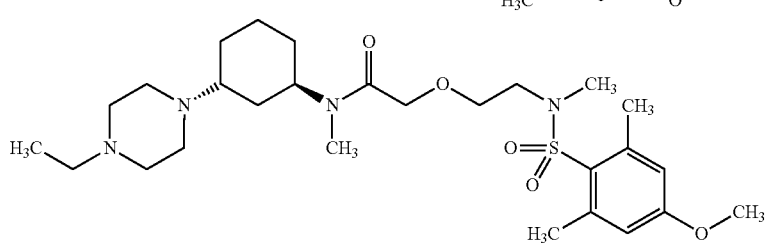

Analogously to Example 1g) the title compound was prepared from product 1d) and product 26d) as a mixture of diastereomers. The purification and the separation of the cis-isomers from the trans-isomers were carried out by preparative HPLC (method 10).
$C_{14}H_{21}NO_6S$ (538.74)
$[M+H]^+$=539 analytical HPLC (method 5): retention time=1.56 min (cis-diastereomer)

analytical HPLC (method 5): retention time=1.75 min (trans-diastereomer)

26f)

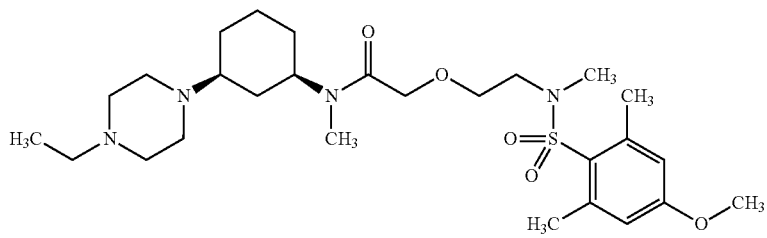 [SMILES: CCN1CCN([C@H]2CCC[C@@H](N(C)C(=O)COCCN(C)S(=O)(=O)c3c(C)cc(OC)cc3C)C2)CC1]

The mixture of the cis-isomers from product 26e) was separated into the enantiomers on the chiral phase according to HPLC method 13. In this way the title compound was obtained as the fast eluting enantiomer.
$C_{14}H_{21}NO_6S$ (538.74)
$[M+H]^+$=539
HPLC (method 13): retention time=26.85 min

Example 27

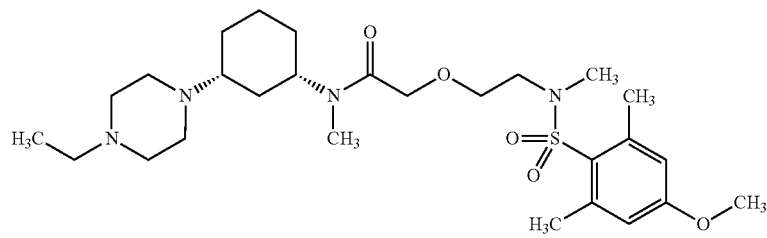 [SMILES: CCN1CCN([C@@H]2CCC[C@H](N(C)C(=O)COCCN(C)S(=O)(=O)c3c(C)cc(OC)cc3C)C2)CC1]

The mixture of the cis-isomers from product 26e) was separated into the enantiomers on the chiral phase according to HPLC method 13. In this way the title compound was obtained as the slowly eluting enantiomer.

$C_{14}H_{21}NO_6S$ (538.74)

[M+H]⁺=539

HPLC (method 13): retention time=31.90 min

Example 28

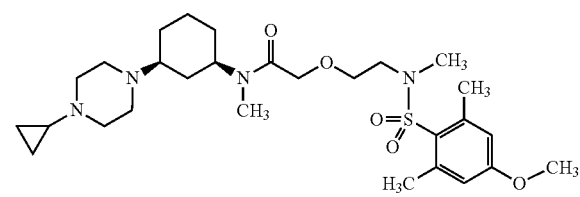 [SMILES: COc1cc(C)c(S(=O)(=O)N(C)CCOCC(=O)N(C)[C@@H]2CCC[C@H](N3CCN(C4CC4)CC3)C2)c(C)c1]

28a)

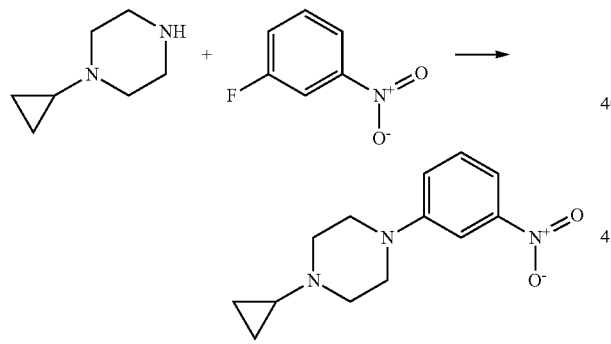

The title compound was prepared analogously to Example 26a) and purified by preparative HPLC (method 9).

$C_{13}H_{17}N_3O_2 \times C_2HF_3O_2$ (361.32)

[M+H]⁺=248 analytical HPLC (method 3): retention time=0.99 min

28b)

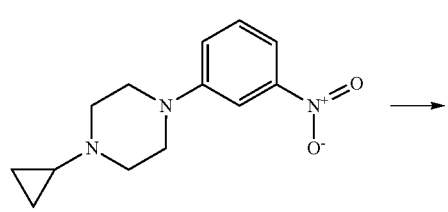

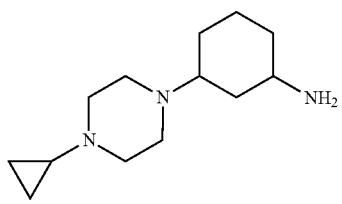

Analogously to Example 26b) the title compound was prepared as a diastereomeric mixture of product 28a).

$C_{13}H_{25}N_3$ (223.36)

[M+H]⁺=224 analytical HPLC (method 5): retention time=1.30 min

28c)

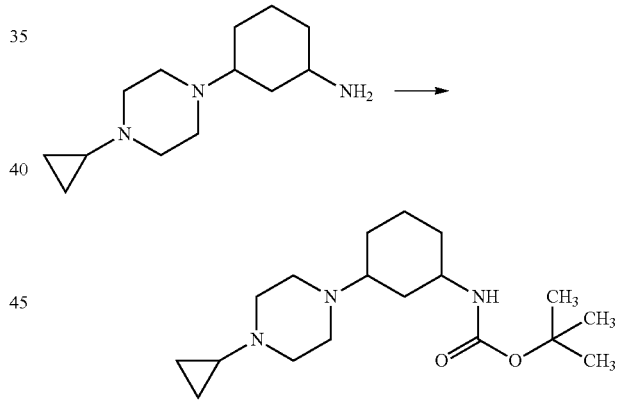

Analogously to Example 26c) the title compound was prepared as a diastereomeric mixture of product 28b).

$C_{18}H_{33}N_3O_2$ (323.47)

analytical HPLC (method 2): retention time=1.58 min

28d)

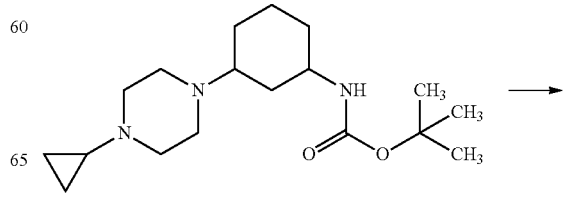

-continued

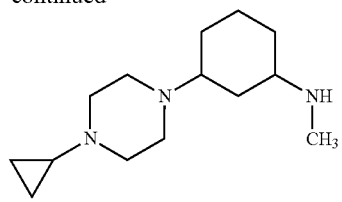

Analogously to Example 14d) the title compound was prepared as a diastereomeric mixture of product 28c).

$C_{14}H_{27}N_3$ (237.38)

$[M+H]^+=238$ analytical HPLC (method 5): retention time=1.58 min

28e)

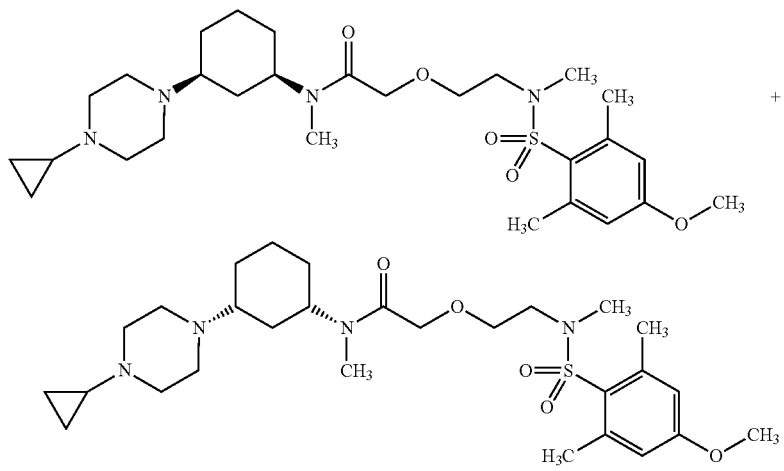

Analogously to Example 12c) the title compound was prepared from product 1d) and product 28d). After chromatographic purification the product was obtained as a racemic mixture of the cis-isomers.

$C_{28}H_{46}N_4O_5S$ (550.76)
$[M+H]^+=551$
analytical HPLC (method 5): retention time=1.65 min Example 29

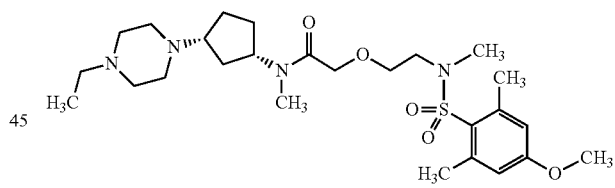

Product 6c) (racemic mixture of the cis-isomers) was separated into the enantiomers on the chiral phase according to HPLC method 13. In this way the title compound was obtained as a fast eluting enantiomer.

$C_{26}H_{44}N_4O_5S \times C_2HF_3O_2$ (638.74)
$[M+H]^+=525$
HPLC (method 13): retention time=14.83 min Example 30

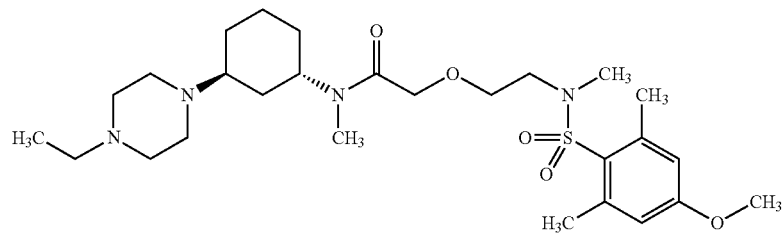 [SMILES: CCN1CCN([C@H]2CCC[C@H](N(C)C(=O)COCCN(C)S(=O)(=O)c3c(C)cc(OC)cc3C)C2)CC1]

Example 31

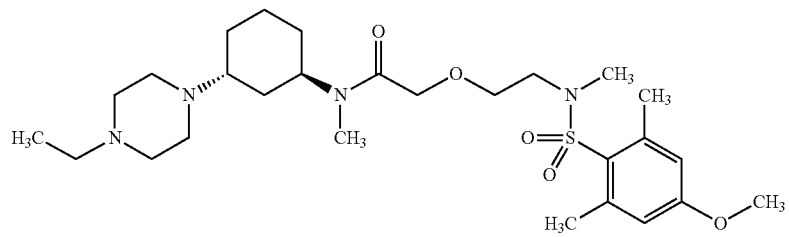 [SMILES: CCN1CCN([C@@H]2CCC[C@@H](N(C)C(=O)COCCN(C)S(=O)(=O)c3c(C)cc(OC)cc3C)C2)CC1]

The mixture of diastereomers from Example 26e) was separated into the pairs of diastereomers by preparative HPLC (method 10). In this way the title compounds 30) and 31) were obtained as a racemic mixture of the trans-isomers.
$C_{14}H_{21}NO_6S$ (538.74)
$[M+H]^+=539$
analytical HPLC (method 5): retention time=1.75 min

Example 32

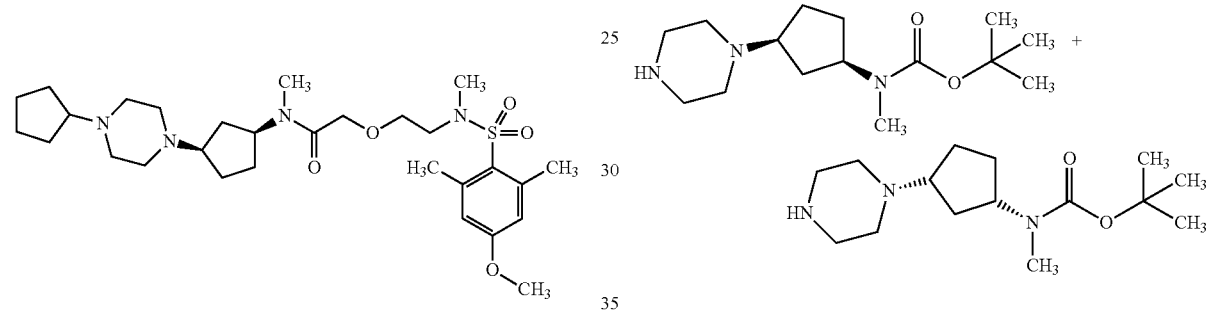

32a)

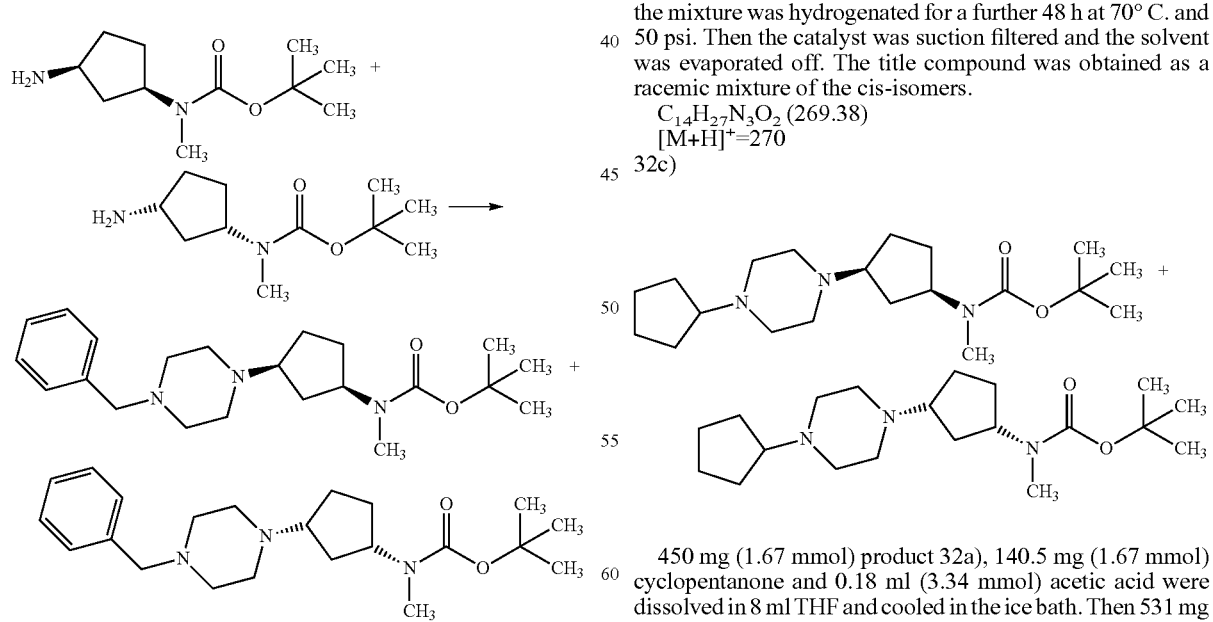

1.5 g (6.34 mmol) N,N-bis(2-chloroethyl)benzylamine were added to a suspension of 1.5 g (6.34 mmol) tert-butyl (3-amino-cyclopentyl)-carbamate hydrochloride, 4.38 g (31.68 mmol) potassium carbonate and 0.11 g (0.63 mmol) potassium iodide in 36 ml acetonitrile and the mixture was refluxed for 4 h. Then the cooled reaction mixture was diluted with DCM and washed with water. The organic phase was dried on sodium sulphate and evaporated down. The racemic mixture of the cis-isomers was obtained.
$C_{21}H_{33}N_3O_2$ (359.51)
$[M+H]^+=360$ 32b)

1.8 g (5.01 mmol) of product 32a) and 0.2 g palladium/charcoal in 20 ml MeOH were first of all hydrogenated for 48 h at 50° C. and under a hydrogen atmosphere of 50 psi. Then the mixture was hydrogenated for a further 48 h at 70° C. and 50 psi. Then the catalyst was suction filtered and the solvent was evaporated off. The title compound was obtained as a racemic mixture of the cis-isomers.
$C_{14}H_{27}N_3O_2$ (269.38)
$[M+H]^+=270$ 32c)

450 mg (1.67 mmol) product 32a), 140.5 mg (1.67 mmol) cyclopentanone and 0.18 ml (3.34 mmol) acetic acid were dissolved in 8 ml THF and cooled in the ice bath. Then 531 mg (2.51 mmol) sodium triacetoxyborohydride were added batchwise and the mixture was stirred for 2 h at RT. The suspension was filtered and evaporated down. The title compound was obtained as a racemic mixture of the cis-isomers.
$C_{19}H_{35}N_3O_2$ (337.5)
$[M+H]^+=338$ 32d)

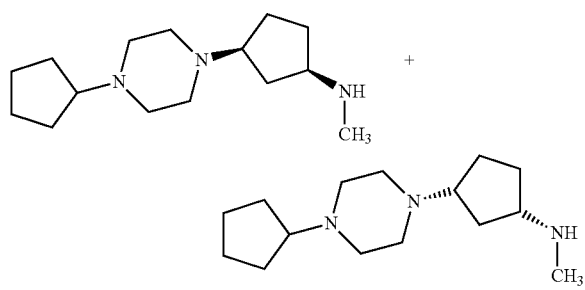

32e)

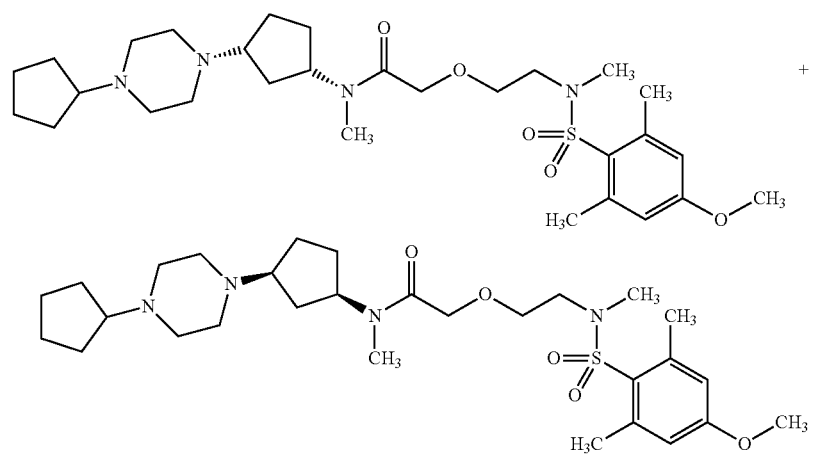

Analogously to Example 14d) the title compound was prepared from product 32c). The title compound was obtained as a racemic mixture of the cis-isomers.

$C_{15}H_{29}N_3$ (251.41)

$[M+H]^+=252$ analytical HPLC (method 3): retention time=0.30 min

Analogously to Example 1g) the title compound was prepared as a racemic mixture of the cis-isomers from product 1d) and product 32d).

$C_{29}H_{48}N_4O_5S \times C_2HF_3O_2$ (678.81)
$[M+H]^+=565$
analytical HPLC (method 2): retention time=1.53 min 32f)

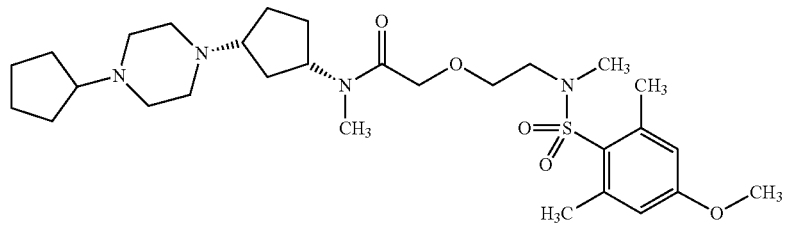

The racemic mixture of Example 32e) was separated into the cis-enantiomers on the chiral phase according to HPLC method 14. In this way the title compound was obtained as the fast eluting enantiomer.

$C_{29}H_{48}N_4O_5S$ (564.78)
$[M+H]^+=565$
HPLC (method 14): retention time=1.66 min (fast eluting enantiomer)

32g)

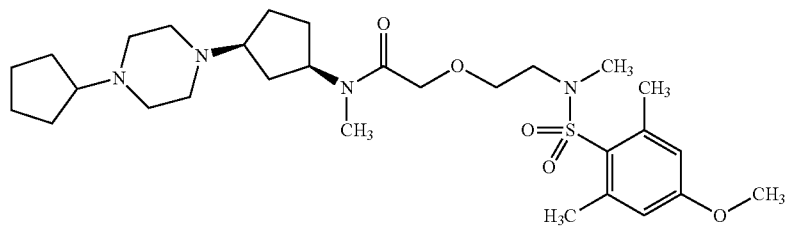 [SMILES: COc1cc(C)c(S(=O)(=O)N(C)CCOCC(=O)N(C)[C@@H]2CC[C@H](N3CCN(C4CCCC4)CC3)C2)c(C)c1]

The racemic mixture of Example 32e) was separated into the cis-enantiomers on the chiral phase according to HPLC method 14. In this way the title compound was obtained as the slowly eluting enantiomer.

$C_{29}H_{48}N_4O_5S$ (564.78)
$[M+H]^+=565$
HPLC (method 14): retention time=1.77 min (slowly eluting enantiomer)

Example 33

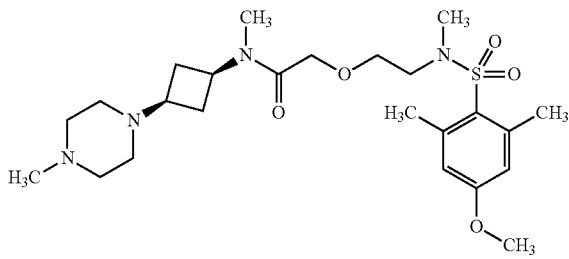

33a)

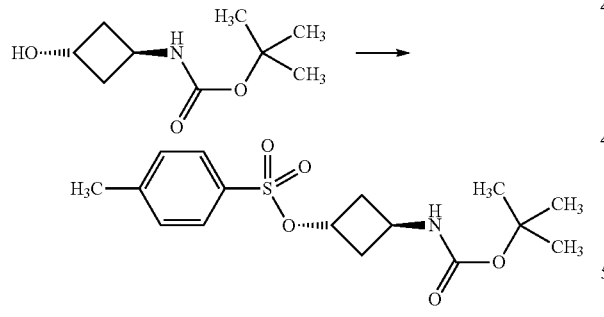

498 mg (2.59 mmol) p-toluenesulphonic acid chloride were added to a solution of 440 mg (2.35 mmol) trans-tert-butyl-3-hydroxycyclobutylcarbamate and 0.74 ml (9.4 mmol) anhydrous pyridine in 7 ml DCM while cooling with ice under a nitrogen atmosphere and the mixture was stirred at RT. After several hours some more DMAP was added and the mixture was stirred for a further 24 h at RT. The reaction mixture was diluted with EE, extracted once with 20% citric acid solution, washed five times with water and once with saturated sodium chloride solution. The organic phase was dried on magnesium sulphate and the filtrate was evaporated down.

$C_{16}H_{23}NO_5S$ (341.42)
$[M+NH_4]^+=359$
analytical HPLC (method 3): retention time=2.50 min 33b)

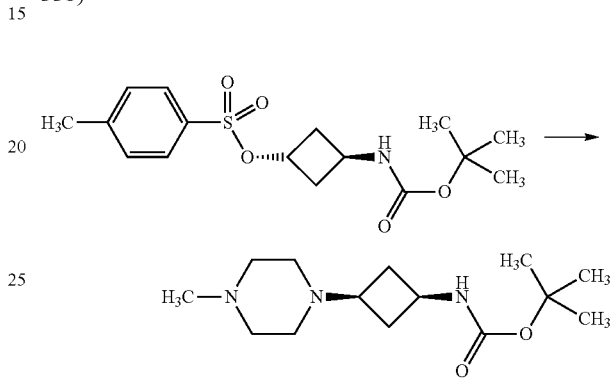

800 mg (2.34 mmol) product 33a) were dissolved in 2 ml (18.03 mmol) 1-methylpiperazine and combined with 20 mg (0.16 mmol) DMAP. Then the reaction mixture was heated to 100° C. overnight in the microwave apparatus. Then the solvent was evaporated off and the residue was purified by preparative HPLC (method 11).

$C_{14}H_{27}N_3O_2$ (269.38)
$[M+H]^+=270$

33c)

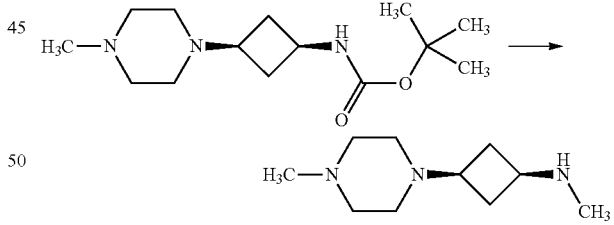

3.9 ml (7.8 mmol) 2M lithium aluminium hydride solution in THF were slowly added dropwise to 500 mg (1.3 mmol) product 33b) in 12 ml anhydrous THF and then the mixture was stirred for 4 h at reflux temperature. Then the mixture was cooled and a little water (3 to 4 ml) was slowly added. The precipitated solid was suction filtered, washed with acetonitrile and the filtrate was evaporated down. The residue was triturated with 2 ml of 2M ethereal hydrochloric acid and the solvent was evaporated off.

$C_{10}H_{21}N_3 \times 3HCl$ (292.68)
analytical HPLC (method 4): retention time=096 min 33d)

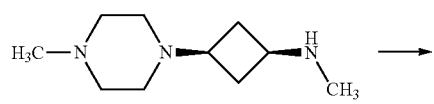

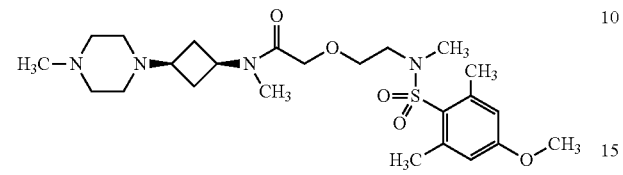

Analogously to Example 1g) the title compound was prepared from product 1d) and product 33c).

$C_{24}H_{40}N_4O_5S \times C_2HF_3O_2$ (610.69)

$[M+H]^+=497$ analytical HPLC (method 3): retention time=1.56 min

Example 34

34a)

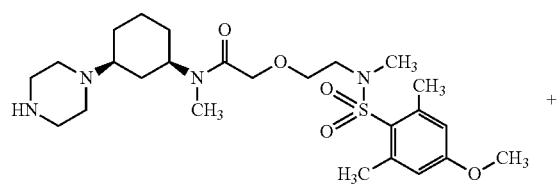

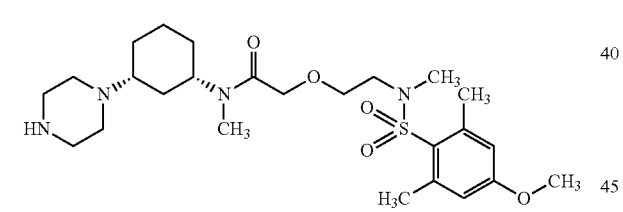

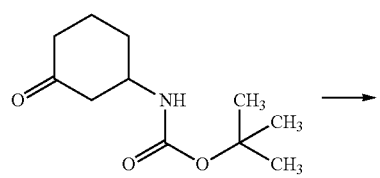

-continued

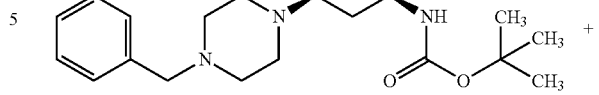

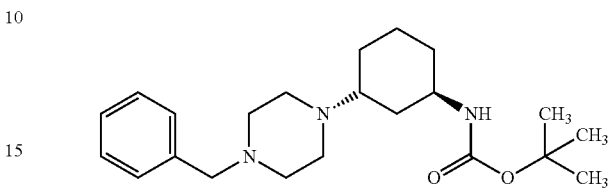

Analogously to Example (1e) 3-(tert-butyloxycarbonyl-amino)-cyclohexanone was reacted with 1-benzylpiperazine. The product was obtained as a mixture of diastereomers which was separated by chromatography into the racemic cis- and trans-mixtures (HPLC method 10).

cis-racemate:

$C_{22}H_{35}N_3O_2$ (373.5)

$[M+H]^+=374$ analytical HPLC (method 4): retention time=1.24 min trans-racemate:

$C_{22}H_{35}N_3O_2$ (373.5)

$[M+H]^+=374$ analytical HPLC (method 4): retention time=1.29 min

34b)

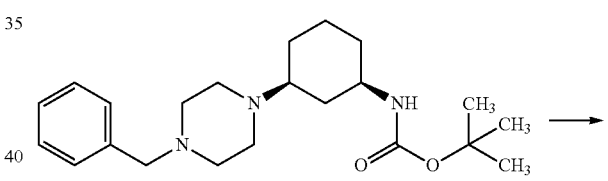

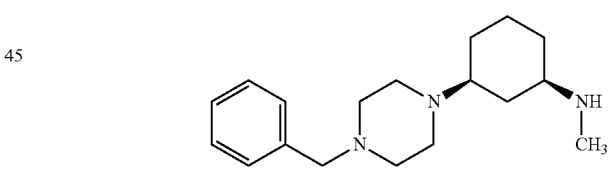

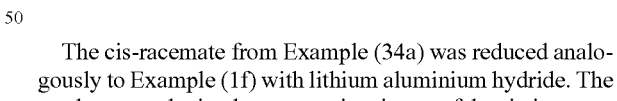

The cis-racemate from Example (34a) was reduced analogously to Example (1f) with lithium aluminium hydride. The product was obtained as a racemic mixture of the cis-isomers.

$C_{18}H_{29}N_3$ (287.4)

$[M+H]^+=288$ analytical HPLC (method 6): retention time=1.69 min

34c)

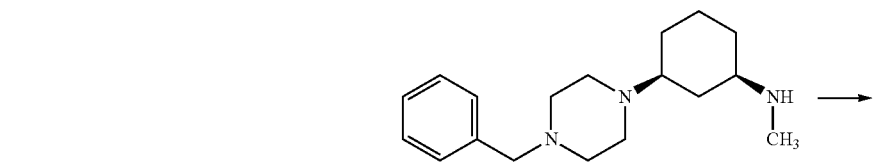

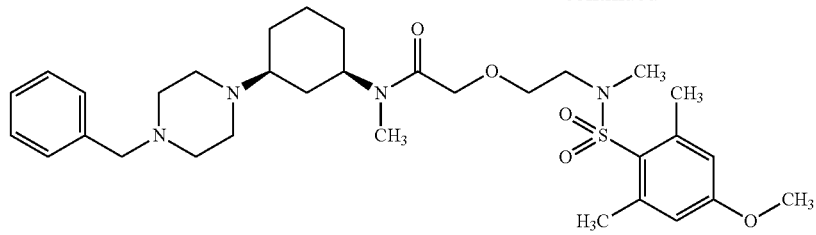

The product from Example (34b) was further reacted analogously to Example (1g). The product was obtained as a racemic mixture of the cis-isomers.

$C_{32}H_{48}N_4O_5S$ (600.8)
[M+H]$^+$=601
analytical HPLC (method 6): retention time=1.79 min 34d)

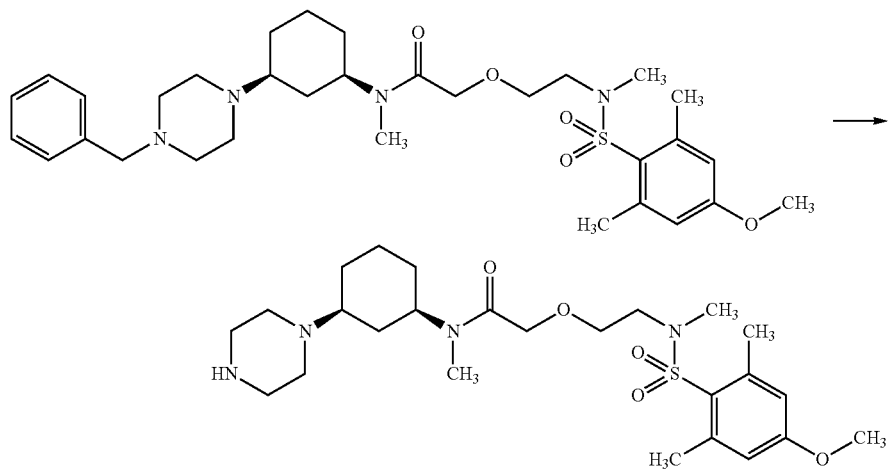

The product from (34c) (86 mg, 0.14 mmol) was dissolved in 10 ml of methanol, combined with 50 mg Pd/charcoal (10%) and hydrogenated for two hours at ambient temperature. The product was obtained as a racemic mixture of the cis-isomers.

Yield: 63 mg (60% of theory)

$C_{25}H_{42}N_4O_5S$ (510.7)

[M+H]$^+$=511 analytical HPLC (method 6): retention time=1.62 min

Example 35

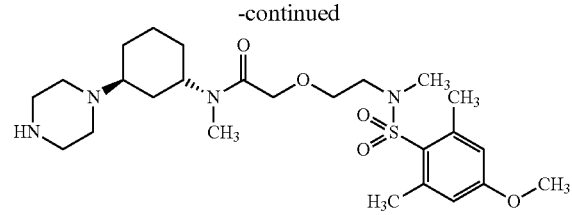

Analogously to Example (34) the product was prepared in three synthesis steps, starting from the trans-racemate of Example (34a).

$C_{25}H_{42}N_4O_5S$ (510.7)
[M+H]$^+$=511
analytical HPLC (method 6): retention time=1.44 min Example 36

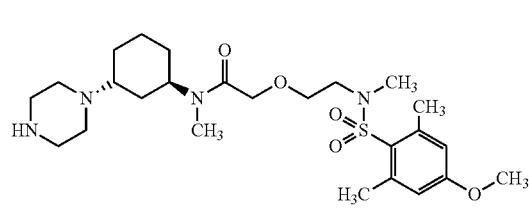

+

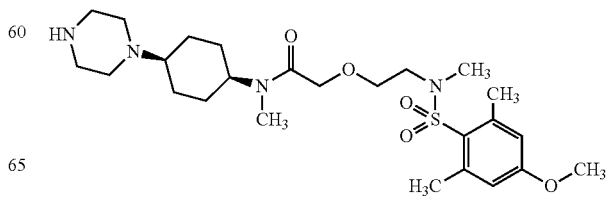

Analogously to Example (34) the product was prepared in four synthesis steps, starting from 4-(tert-butyloxycarbonyl-amino)-cyclohexanone.

$C_{25}H_{42}N_4O_5S$ (510.7)

$[M+H]^+ = 511$ analytical HPLC (method 4): retention time=1.68 min

The following Examples describe pharmaceutical formulations which contain as active substance any desired compound of general formula I:

Example I

Dry Ampoule with 75 mg of Active Compound per 10 ml

Composition:

|  |  |
|---|---|
| Active compound | 75.0 mg |
| Mannitol | 50.0 mg |
| Water for injection | ad 10.0 ml |

Production:

Active compound and mannitol are dissolved in water. The charged ampoules are freeze dried. Water for injection is used to dissolve to give the solution ready for use.

Example II

Tablet with 50 mg of Active Compound

Composition:

|  |  |
|---|---|
| (1) Active compound | 50.0 mg |
| (2) Lactose | 98.0 mg |
| (3) Maize starch | 50.0 mg |
| (4) Polyvinylpyrrolidone | 15.0 mg |
| (5) Magnesium stearate | 2.0 mg |
|  | 215.0 mg |

Production:

(1), (2) and (3) are mixed and granulated with an aqueous solution of (4). (5) is admixed to the dry granules. Tablets are compressed from this mixture, biplanar with a bevel on both sides and dividing groove on one side.

Diameter of the tablets: 9 mm.

Example III

Tablet with 350 mg of Active Compound

Composition:

|  |  |
|---|---|
| (1) Active compound | 350.0 mg |
| (2) Lactose | 136.0 mg |
| (3) Maize starch | 80.0 mg |
| (4) Polyvinylpyrrolidone | 30.0 mg |
| (5) Magnesium stearate | 4.0 mg |
|  | 600.0 mg |

Production:

(1), (2) and (3) are mixed and granulated with an aqueous solution of (4). (5) is admixed to the dry granules. Tablets are compressed from this mixture, biplanar with a bevel on both sides and dividing groove on one side.

Diameter of the tablets: 12 mm.

Example IV

Capsule with 50 mg of Active Compound

Composition:

|  |  |
|---|---|
| (1) Active compound | 50.0 mg |
| (2) Maize starch dried | 58.0 mg |
| (3) Lactose powdered | 50.0 mg |
| (4) Magnesium stearate | 2.0 mg |
|  | 160.0 mg |

Production:

(1) is triturated with (3). This trituration is added to the mixture of (2) and (4) with vigorous mixing.

This powder mixture is packed into hard gelatine two-piece capsules of size 3 in a capsule-filling machine.

Example V

Capsules with 350 mg of Active Compound

Composition:

|  |  |
|---|---|
| (1) Active compound | 350.0 mg |
| (2) Maize starch dried | 46.0 mg |
| (3) Lactose powdered | 30.0 mg |
| (4) Magnesium stearate | 4.0 mg |
|  | 430.0 mg |

Production:

(1) is triturated with (3). This trituration is added to the mixture of (2) and (4) with vigorous stirring.

This powder mixture is packed into hard gelatine two-piece capsules of size 0 in a capsule-filling machine.

Example VI

Suppositories with 100 mg of Active Compound 1 suppository comprises:

|  |  |
|---|---|
| Active compound | 100.0 mg |
| Polyethylene glycol (M.W. 1500) | 600.0 mg |
| Polyethylene glycol (M.W. 6000) | 460.0 mg |
| Polyethylene sorbitan monostearate | 840.0 mg |
|  | 2000.0 mg |

The invention claimed is:

1. A compound of the formula I

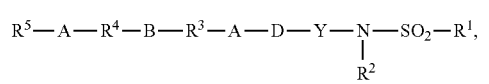

wherein
 A denotes a bond,
 B denotes a bond,
 D-Y together denote the group

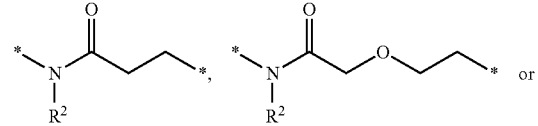

-continued

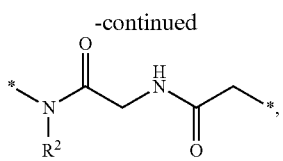

R¹ denotes the group

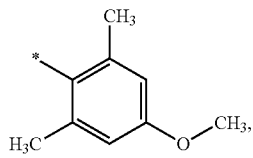

R² denotes H or $C_{1-3}$-alkyl, while each methylene group may be substituted by up to two fluorine atoms and each methyl group may be substituted by up to three fluorine atoms, or also $H_3C—C(O)$, R³ denotes a $C_{4-6}$-cycloalkylene group which may be substituted by one, two or three $R^{3.1}$ groups, $R^{3.1}$ denotes $—CH_3$, $—C_2H_5$, iso-propyl, tert-butyl, —OH, F, Cl, Br, I, R⁴ denotes a saturated 6- or 7-membered diaza heterocycle, and R⁵ denotes $C_{1-3}$-alkyl or $C_{3-5}$-cycloalkyl, or a salt thereof.

2. A compound of the formula formula I according to claim 1, wherein

A denotes a bond,

B denotes a bond,

D-Y together denote the group

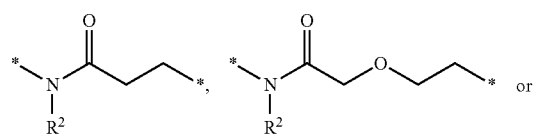

R¹ denotes the group

R² denotes H or $C_{1-3}$-alkyl, while each methylene group may be substituted by up to two fluorine atoms and each methyl group may be substituted by up to three fluorine atoms, or also $H_3C—C(O)$, R³ denotes a $C_{4-6}$-cycloalkylene group, R⁴ denotes a saturated 6- or 7-membered diaza heterocycle, R⁵ denotes $C_{1-3}$-alkyl or $C_{3-5}$-cycloalkyl, or a salt thereof.

3. A compound of the formula I according to claim 1, wherein

R³ denotes a $C_{4-6}$-cycloalkylene group which may be substituted by one, two or three $R^{3.1}$ groups, and $R^{3.1}$ denotes $—CH_3$, $—C_2H_5$, iso-propyl, tert-butyl, —OH, F, Cl, Br or I, with the proviso that the above-mentioned $C_{4-6}$-cycloalkylene group is linked in the 1,3 position to the remainder of the molecule, or a salt thereof.

4. A compound of the formula I according to claim 1, wherein

R³ denotes a $C_{4-6}$-cycloalkylene group which may be substituted by one, two or three $R^{3.1}$ groups, and $R^{3.1}$ denotes $—CH_3$, $—C_2H_5$, iso-propyl, tert-butyl, —OH, F, Cl, Br or I, with the proviso that the above-mentioned $C_{4-6}$-cycloalkylene group is linked in the 1,3 position to the remainder of the molecule, or a salt thereof.

5. A compound of the formula I according to claim 1 selected from the group consisting of:

| No. | Structure |
|---|---|
| (1) | ![structure 1] |
| (2) | ![structure 2] |

-continued
| No. | Structure |
|---|---|
| (3) | 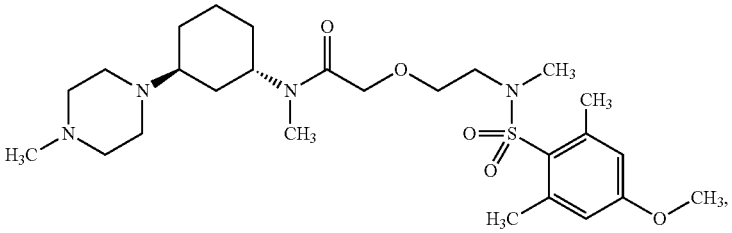 [SMILES: COc1cc(C)c(S(=O)(=O)N(C)CCOCC(=O)N(C)[C@H]2CCC[C@H](N3CCN(C)CC3)C2)c(C)c1] |
| (4) | 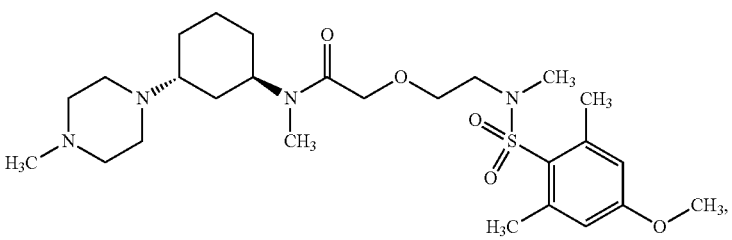 [SMILES: COc1cc(C)c(S(=O)(=O)N(C)CCOCC(=O)N(C)[C@@H]2CCC[C@@H](N3CCN(C)CC3)C2)c(C)c1] |
| (5) | 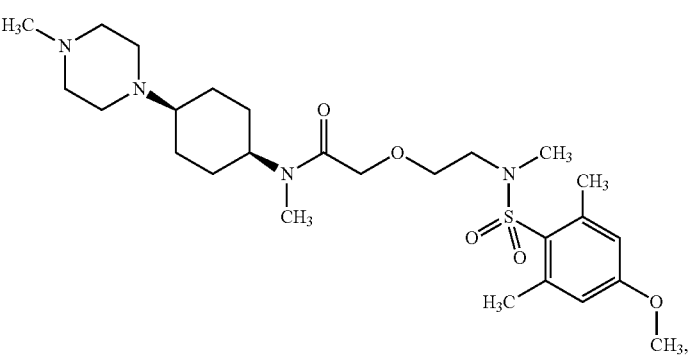 [SMILES: COc1cc(C)c(S(=O)(=O)N(C)CCOCC(=O)N(C)[C@H]2CC[C@@H](N3CCN(C)CC3)CC2)c(C)c1] |
| (6) | 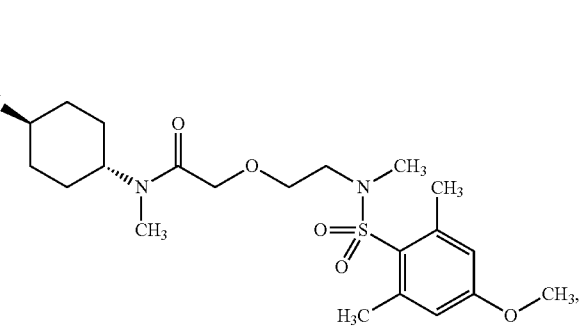 |
| (7) | 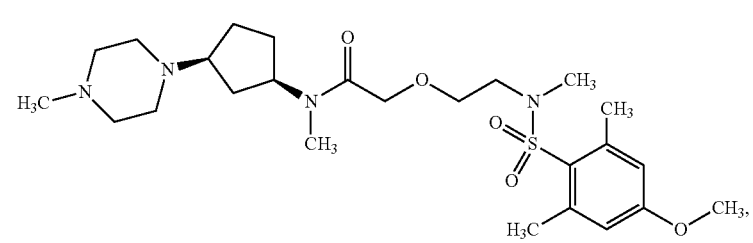 [SMILES: COc1cc(C)c(S(=O)(=O)N(C)CCOCC(=O)N(C)[C@@H]2CC[C@H](N3CCN(C)CC3)C2)c(C)c1] |

| No. | Structure |
|---|---|
| (8) | 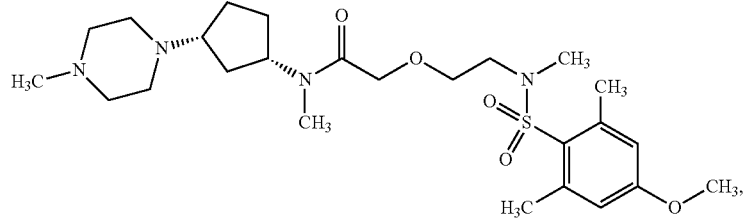 [SMILES: COc1cc(C)c(S(=O)(=O)N(C)CCOCC(=O)N(C)[C@H]2CC[C@@H](N3CCN(C)CC3)C2)c(C)c1] |
| (9) | 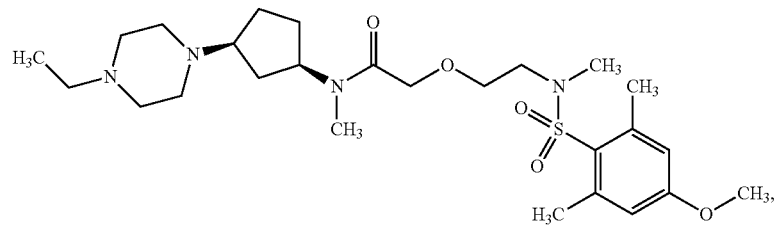 [SMILES: CCN1CCN([C@H]2CC[C@@H](N(C)C(=O)COCCN(C)S(=O)(=O)c3c(C)cc(OC)cc3C)C2)CC1] |
| (10) | 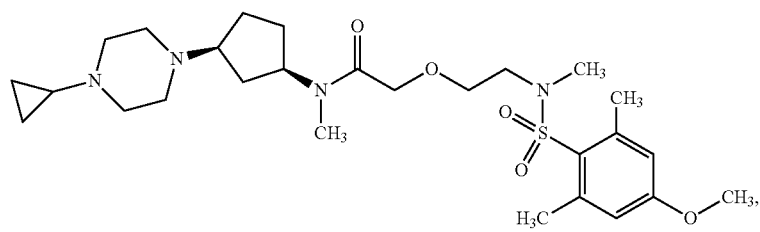 [SMILES: COc1cc(C)c(S(=O)(=O)N(C)CCOCC(=O)N(C)[C@@H]2CC[C@H](N3CCN(C4CC4)CC3)C2)c(C)c1] |
| (11) | 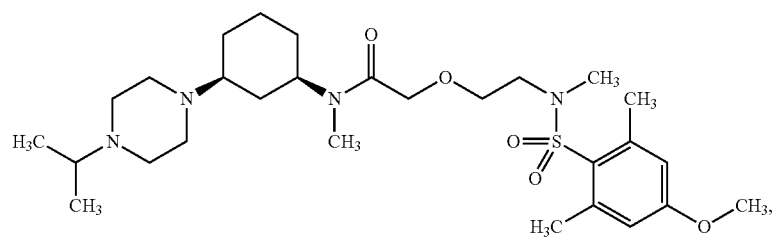 [SMILES: COc1cc(C)c(S(=O)(=O)N(C)CCOCC(=O)N(C)[C@@H]2CCC[C@H](N3CCN(C(C)C)CC3)C2)c(C)c1] |
| (12) | 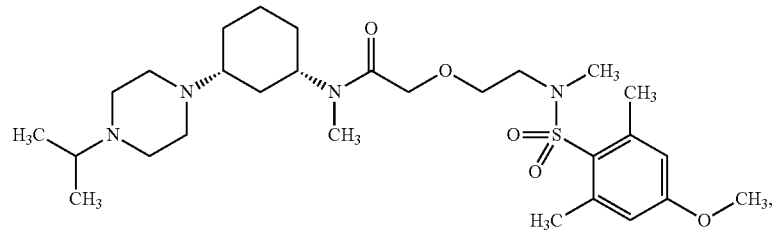 [SMILES: COc1cc(C)c(S(=O)(=O)N(C)CCOCC(=O)N(C)[C@H]2CCC[C@@H](N3CCN(C(C)C)CC3)C2)c(C)c1] |
| (13) | 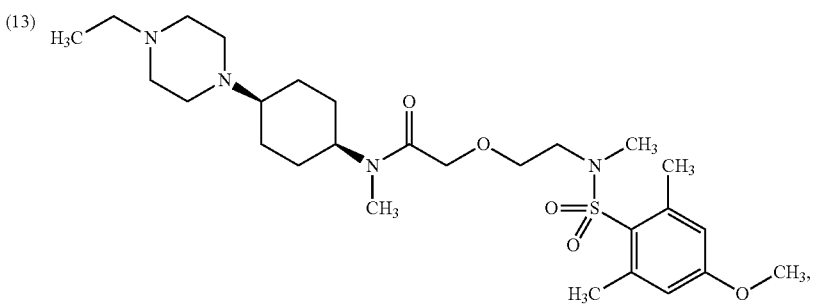 |

-continued

| No. | Structure |
|---|---|
| (14) | 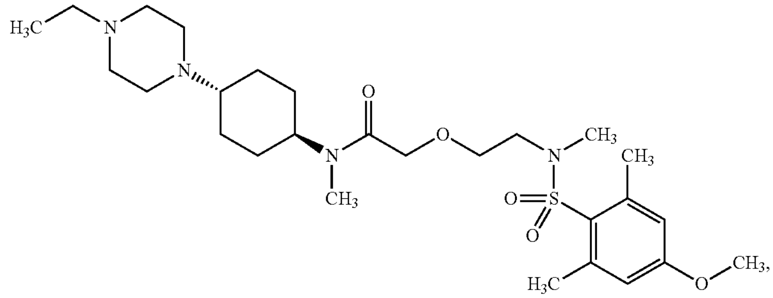 [SMILES: CCN1CCN([C@H]2CC[C@H](N(C)C(=O)COCCN(C)S(=O)(=O)c3c(C)cc(OC)cc3C)CC2)CC1] |
| (15) | 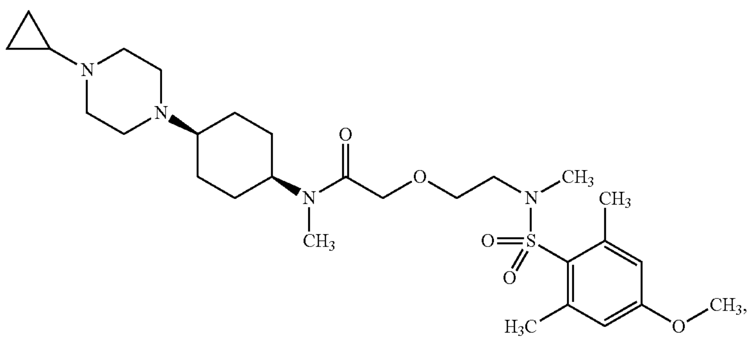 [SMILES: COc1cc(C)c(S(=O)(=O)N(C)CCOCC(=O)N(C)[C@H]2CC[C@@H](N3CCN(C4CC4)CC3)CC2)c(C)c1] |
| (16) | 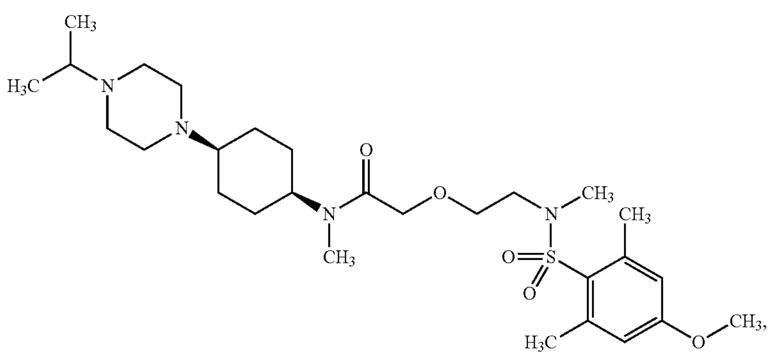 [SMILES: COc1cc(C)c(S(=O)(=O)N(C)CCOCC(=O)N(C)[C@H]2CC[C@@H](N3CCN(C(C)C)CC3)CC2)c(C)c1] |
| (17) | 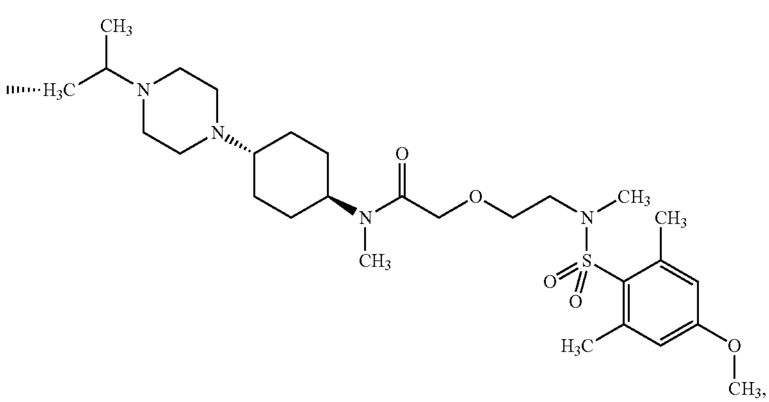 |

| No. | Structure |
|---|---|
| (18) | 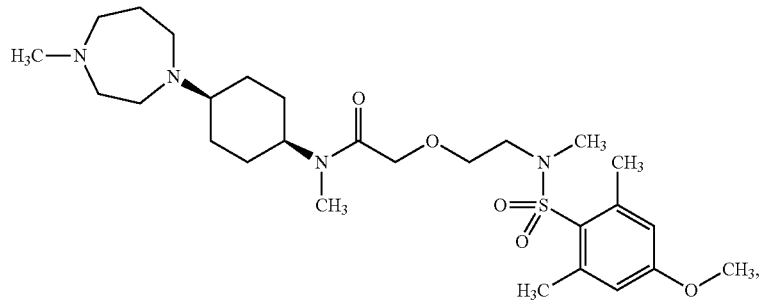 [SMILES: COc1cc(C)c(S(=O)(=O)N(C)CCOCC(=O)N(C)[C@H]2CC[C@@H](N3CCCN(C)CC3)CC2)c(C)c1] |
| (19) | 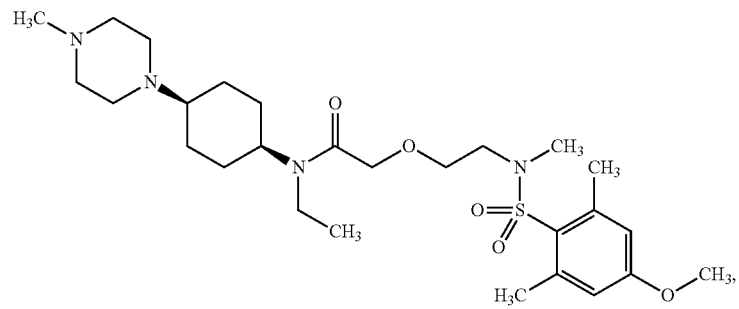 |
| (20) | 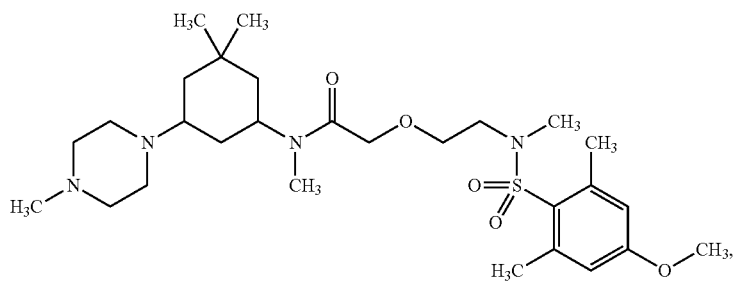 |
| (21) | 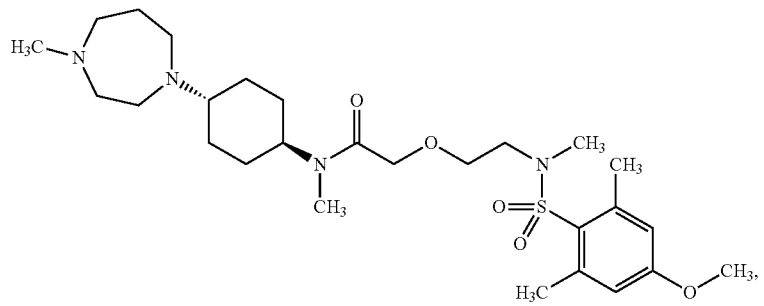 [SMILES: COc1cc(C)c(S(=O)(=O)N(C)CCOCC(=O)N(C)[C@H]2CC[C@H](N3CCCN(C)CC3)CC2)c(C)c1] |
| (22) | 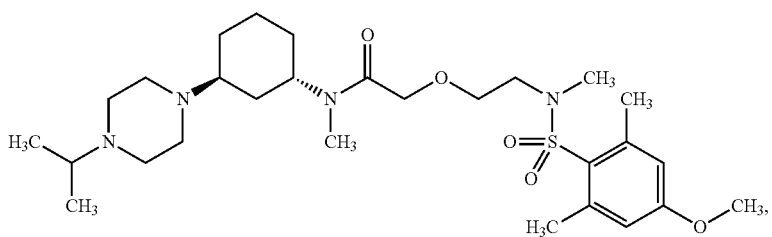 [SMILES: COc1cc(C)c(S(=O)(=O)N(C)CCOCC(=O)N(C)[C@H]2CCC[C@H](N3CCN(C(C)C)CC3)C2)c(C)c1] |

| No. | Structure |
|---|---|
| (23) | 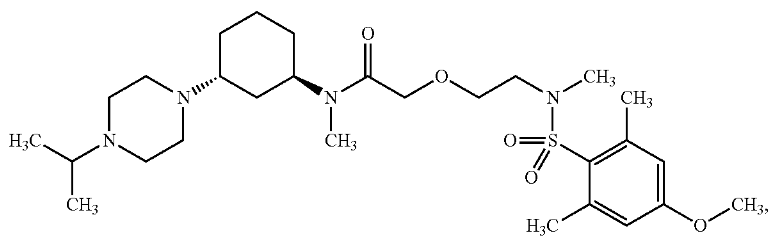 [SMILES: COc1cc(C)c(S(=O)(=O)N(C)CCOCC(=O)N(C)[C@@H]2CCC[C@@H](N3CCN(C(C)C)CC3)C2)c(C)c1] |
| (24) | 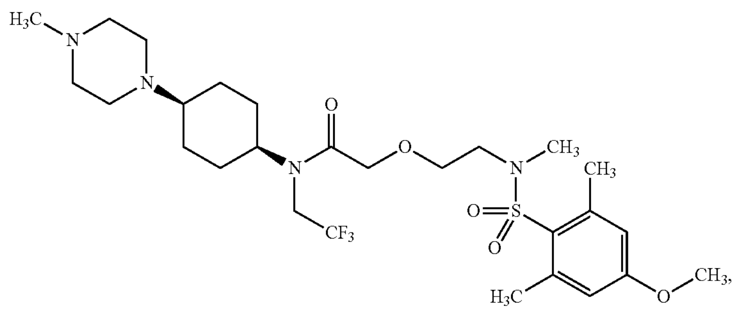 [SMILES: COc1cc(C)c(S(=O)(=O)N(C)CCOCC(=O)N(CC(F)(F)F)[C@H]2CC[C@@H](N3CCN(C)CC3)CC2)c(C)c1] |
| (25) | 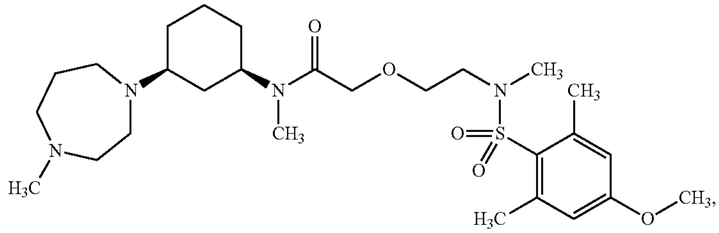 |
| (26) | 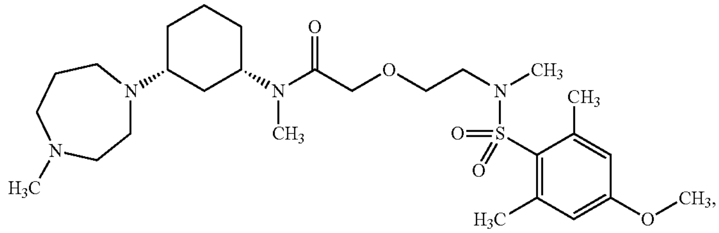 [SMILES: COc1cc(C)c(S(=O)(=O)N(C)CCOCC(=O)N(C)[C@H]2CCC[C@@H](N3CCCN(C)CC3)C2)c(C)c1] |
| (27) | 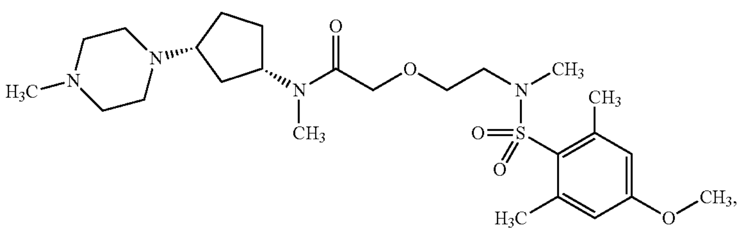 [SMILES: COc1cc(C)c(S(=O)(=O)N(C)CCOCC(=O)N(C)[C@H]2CC[C@@H](N3CCN(C)CC3)C2)c(C)c1] |
| (28) | 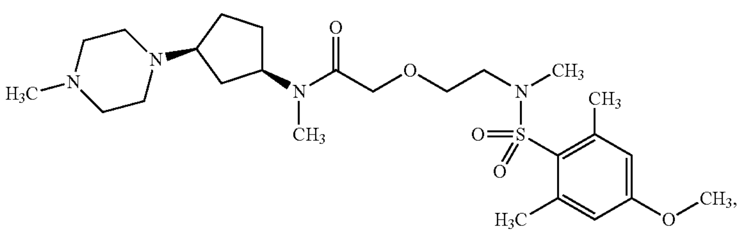 [SMILES: COc1cc(C)c(S(=O)(=O)N(C)CCOCC(=O)N(C)[C@@H]2CC[C@H](N3CCN(C)CC3)C2)c(C)c1] |

| No. | Structure |
|---|---|
| (29) | 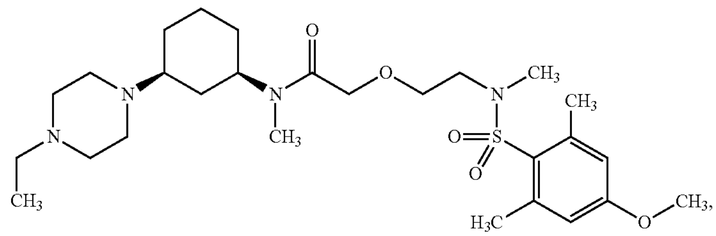 [SMILES: CCN1CCN([C@H]2CCC[C@@H](N(C)C(=O)COCCN(C)S(=O)(=O)c3c(C)cc(OC)cc3C)C2)CC1] |
| (30) | 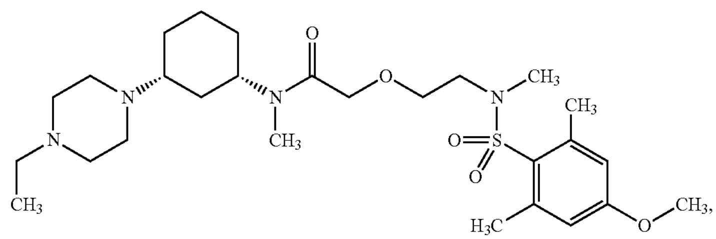 [SMILES: CCN1CCN([C@@H]2CCC[C@H](N(C)C(=O)COCCN(C)S(=O)(=O)c3c(C)cc(OC)cc3C)C2)CC1] |
| (31) | 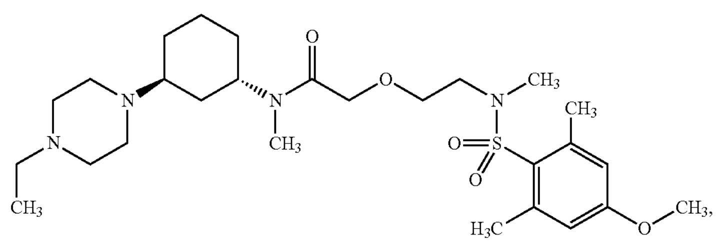 [SMILES: CCN1CCN([C@H]2CCC[C@H](N(C)C(=O)COCCN(C)S(=O)(=O)c3c(C)cc(OC)cc3C)C2)CC1] |
| (32) | 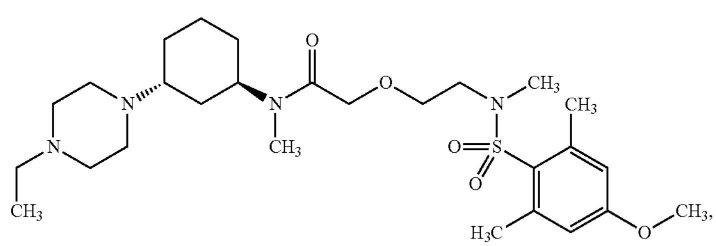 [SMILES: CCN1CCN([C@@H]2CCC[C@@H](N(C)C(=O)COCCN(C)S(=O)(=O)c3c(C)cc(OC)cc3C)C2)CC1] |
| (33) | 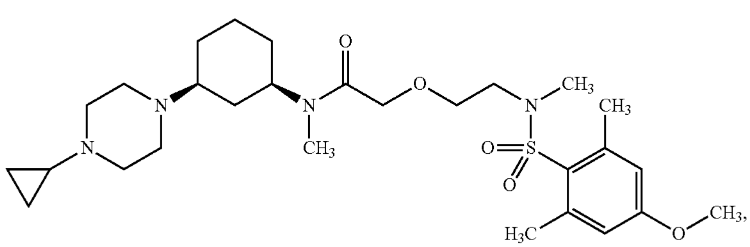 [SMILES: COc1cc(C)c(S(=O)(=O)N(C)CCOCC(=O)N(C)[C@@H]2CCC[C@H](N3CCN(C4CC4)CC3)C2)c(C)c1] |
| (34) | 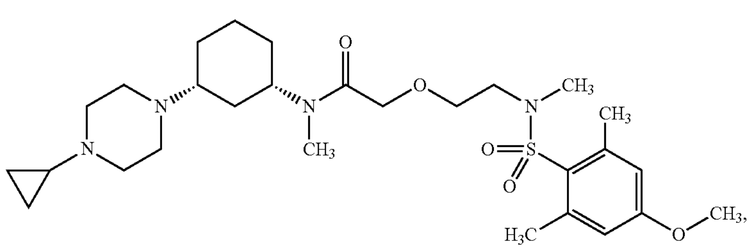 [SMILES: COc1cc(C)c(S(=O)(=O)N(C)CCOCC(=O)N(C)[C@H]2CCC[C@@H](N3CCN(C4CC4)CC3)C2)c(C)c1] |

| No. | Structure |
|---|---|
| (35) | (structure: 4-ethylpiperazinyl-cyclopentyl-N(CH3)-C(=O)-CH2-O-CH2CH2-N(CH3)-SO2-(2,6-dimethyl-4-methoxyphenyl)) |
| (36) | (structure: 4-cyclopentylpiperazinyl-cyclopentyl-N(CH3)-C(=O)-CH2-O-CH2CH2-N(CH3)-SO2-(2,6-dimethyl-4-methoxyphenyl)) |
| (37) | (structure: 4-cyclopentylpiperazinyl-cyclopentyl-N(CH3)-C(=O)-CH2-O-CH2CH2-N(CH3)-SO2-(2,6-dimethyl-4-methoxyphenyl)), and |
| (38) | (structure: 4-methylpiperazinyl-cyclobutyl-N(CH3)-C(=O)-CH2-O-CH2CH2-N(CH3)-SO2-(2,6-dimethyl-4-methoxyphenyl)) | or a salt thereof.

6. A compound of the formula I according to claim 1 selected from the group consisting of:

| No. | Structure |
|---|---|
| (1) | (structure: 4-methylpiperazinyl-cyclohexyl-N(CH3)-C(=O)-CH2-O-CH2CH2-N(CH3)-SO2-(2,6-dimethyl-4-methoxyphenyl)) |

| No. | Structure |
|---|---|
| (2) | 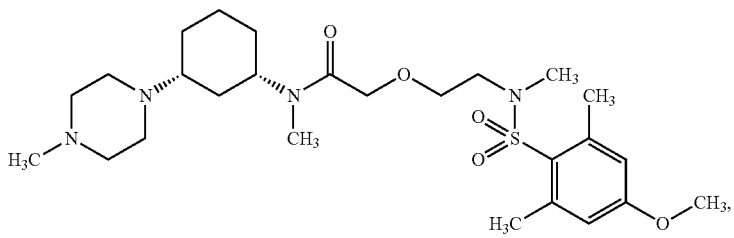 [SMILES: COc1cc(C)c(S(=O)(=O)N(C)CCOCC(=O)N(C)[C@H]2CCC[C@@H](N3CCN(C)CC3)C2)c(C)c1] |
| (3) | 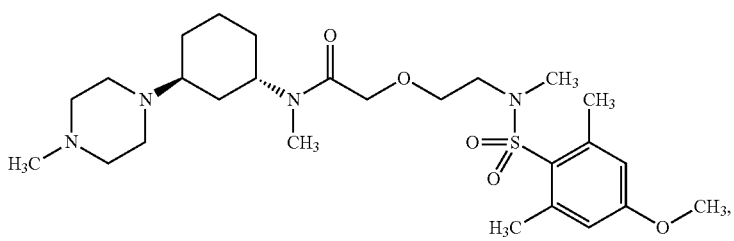 [SMILES: COc1cc(C)c(S(=O)(=O)N(C)CCOCC(=O)N(C)[C@H]2CCC[C@H](N3CCN(C)CC3)C2)c(C)c1] |
| (4) | 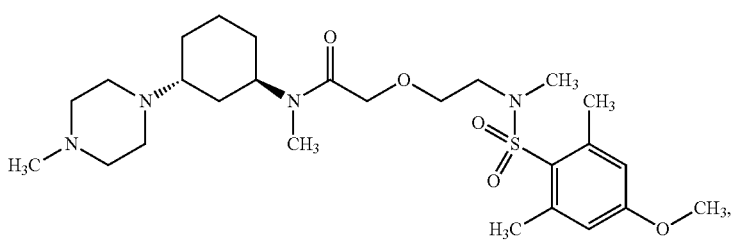 [SMILES: COc1cc(C)c(S(=O)(=O)N(C)CCOCC(=O)N(C)[C@@H]2CCC[C@@H](N3CCN(C)CC3)C2)c(C)c1] |
| (5) | 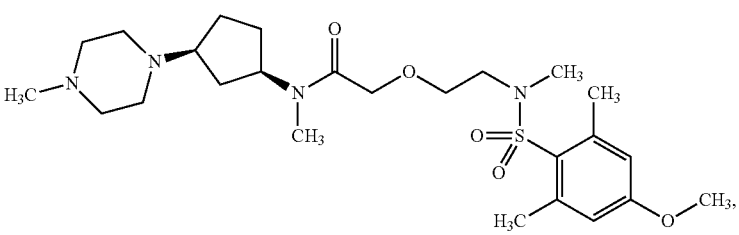 [SMILES: COc1cc(C)c(S(=O)(=O)N(C)CCOCC(=O)N(C)[C@@H]2CC[C@H](N3CCN(C)CC3)C2)c(C)c1] |
| (6) | 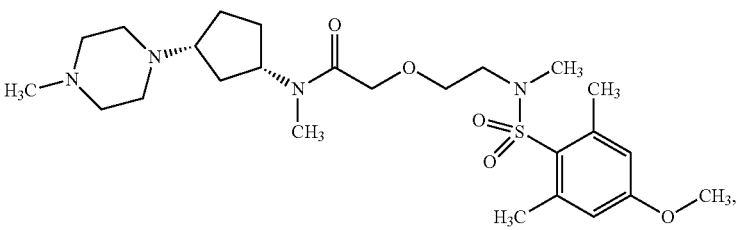 [SMILES: COc1cc(C)c(S(=O)(=O)N(C)CCOCC(=O)N(C)[C@H]2CC[C@@H](N3CCN(C)CC3)C2)c(C)c1] |
| (7) | 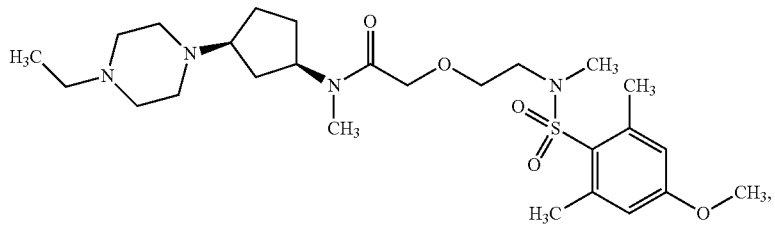 [SMILES: CCN1CCN([C@H]2CC[C@@H](N(C)C(=O)COCCN(C)S(=O)(=O)c3c(C)cc(OC)cc3C)C2)CC1] |

| No. | Structure |
|---|---|
| (8) | 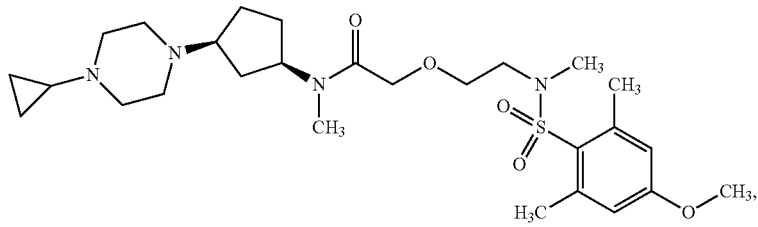 [SMILES: COc1cc(C)c(S(=O)(=O)N(C)CCOCC(=O)N(C)[C@@H]2CC[C@H](N3CCN(C4CC4)CC3)C2)c(C)c1] |
| (9) | 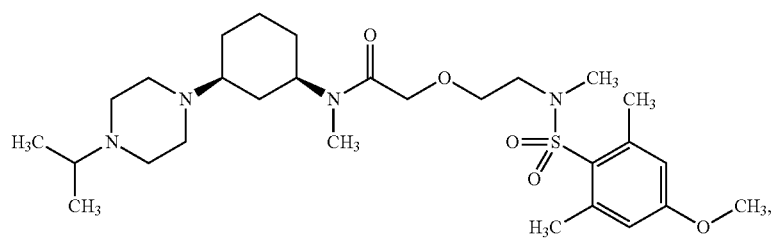 [SMILES: COc1cc(C)c(S(=O)(=O)N(C)CCOCC(=O)N(C)[C@@H]2CCC[C@H](N3CCN(C(C)C)CC3)C2)c(C)c1] |
| (10) | 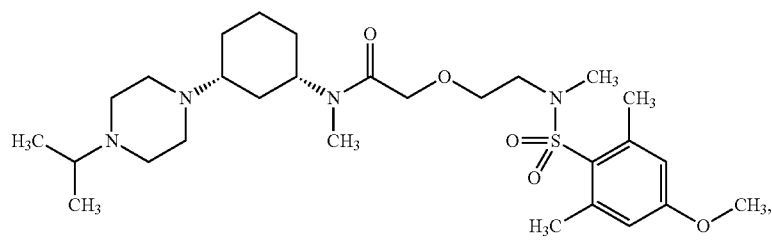 [SMILES: COc1cc(C)c(S(=O)(=O)N(C)CCOCC(=O)N(C)[C@H]2CCC[C@@H](N3CCN(C(C)C)CC3)C2)c(C)c1] |
| (11) | 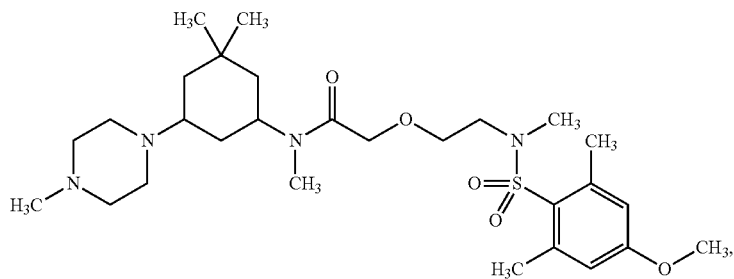 |
| (12) | 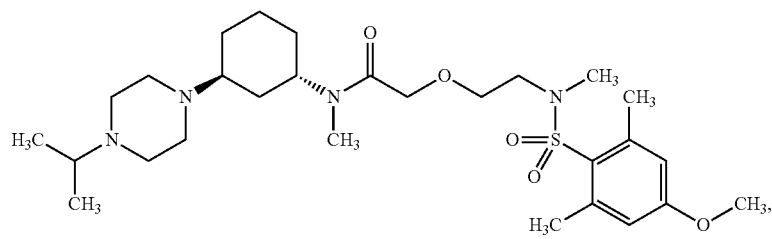 [SMILES: COc1cc(C)c(S(=O)(=O)N(C)CCOCC(=O)N(C)[C@H]2CCC[C@H](N3CCN(C(C)C)CC3)C2)c(C)c1] |
| (13) | 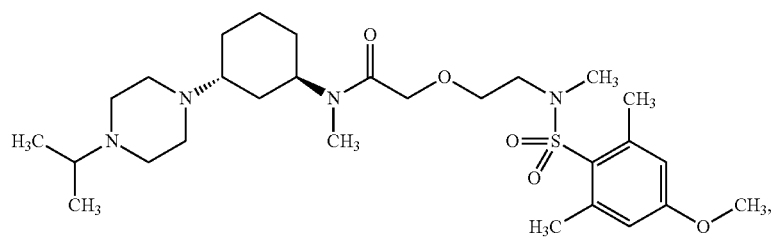 [SMILES: COc1cc(C)c(S(=O)(=O)N(C)CCOCC(=O)N(C)[C@@H]2CCC[C@@H](N3CCN(C(C)C)CC3)C2)c(C)c1] |

| No. | Structure |
|---|---|
| (14) | 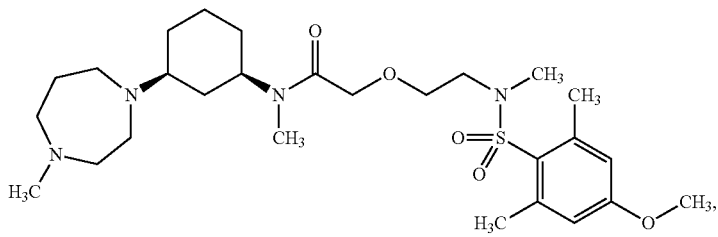 |
| (15) | 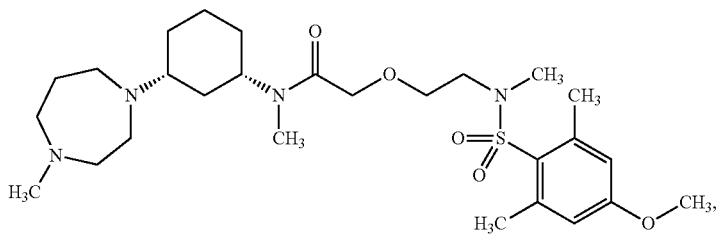 [SMILES: COc1cc(C)c(S(=O)(=O)N(C)CCOCC(=O)N(C)[C@H]2CCC[C@@H](N3CCCN(C)CC3)C2)c(C)c1] |
| (16) | 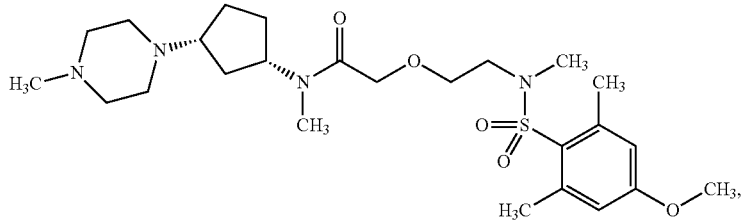 [SMILES: COc1cc(C)c(S(=O)(=O)N(C)CCOCC(=O)N(C)[C@H]2CC[C@@H](N3CCN(C)CC3)C2)c(C)c1] |
| (17) | 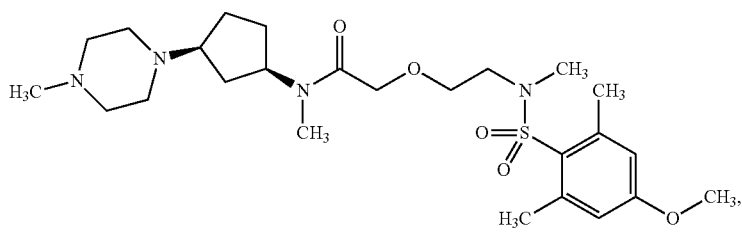 [SMILES: COc1cc(C)c(S(=O)(=O)N(C)CCOCC(=O)N(C)[C@@H]2CC[C@H](N3CCN(C)CC3)C2)c(C)c1] |
| (18) | 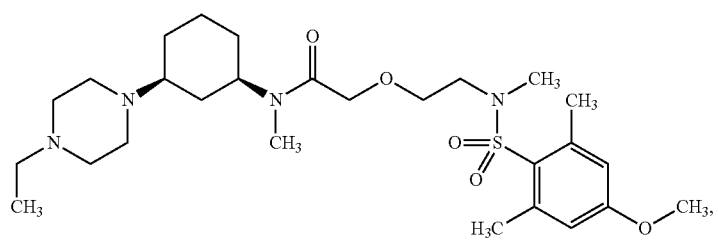 [SMILES: CCN1CCN([C@H]2CCC[C@@H](N(C)C(=O)COCCN(C)S(=O)(=O)c3c(C)cc(OC)cc3C)C2)CC1] |
| (19) | 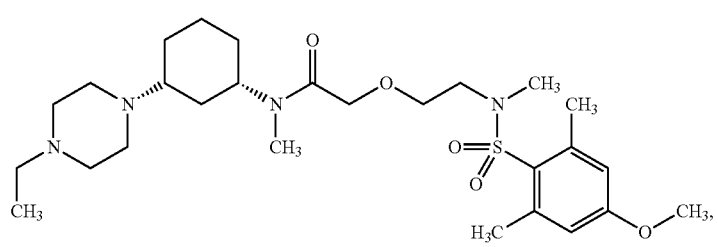 |

-continued
| No. | Structure |
|---|---|
| (20) | 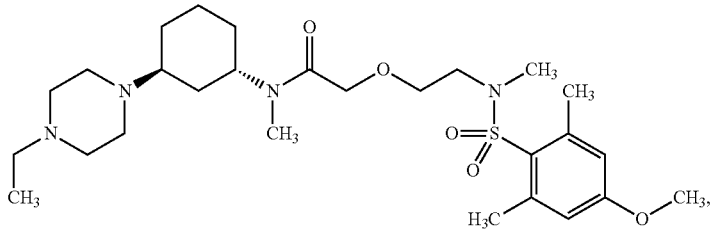 [SMILES: CCN1CCN([C@H]2CCC[C@H](N(C)C(=O)COCCN(C)S(=O)(=O)c3c(C)cc(OC)cc3C)C2)CC1] |
| (21) | 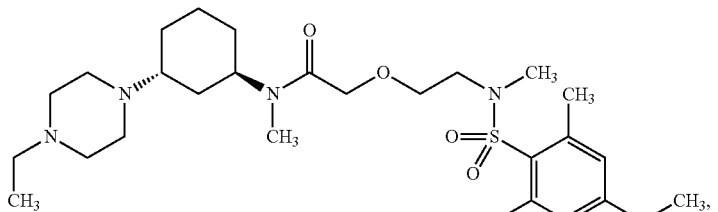 |
| (22) | 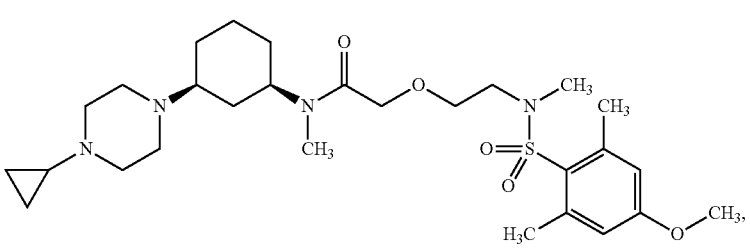 [SMILES: COc1cc(C)c(S(=O)(=O)N(C)CCOCC(=O)N(C)[C@@H]2CCC[C@H](N3CCN(C4CC4)CC3)C2)c(C)c1] |
| (23) | 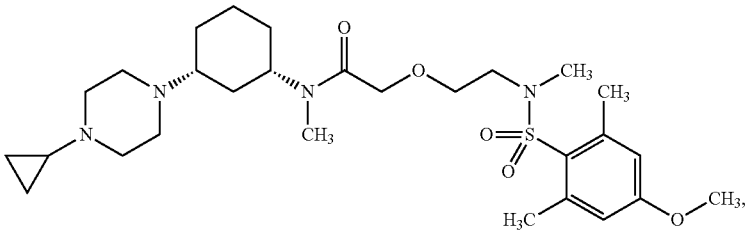 [SMILES: COc1cc(C)c(S(=O)(=O)N(C)CCOCC(=O)N(C)[C@H]2CCC[C@@H](N3CCN(C4CC4)CC3)C2)c(C)c1] |
| (24) | 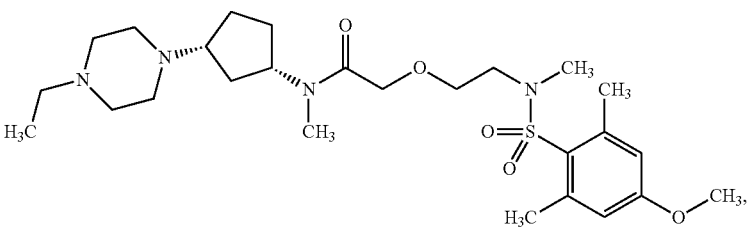 [SMILES: CCN1CCN([C@@H]2CC[C@H](N(C)C(=O)COCCN(C)S(=O)(=O)c3c(C)cc(OC)cc3C)C2)CC1] |
| (25) | 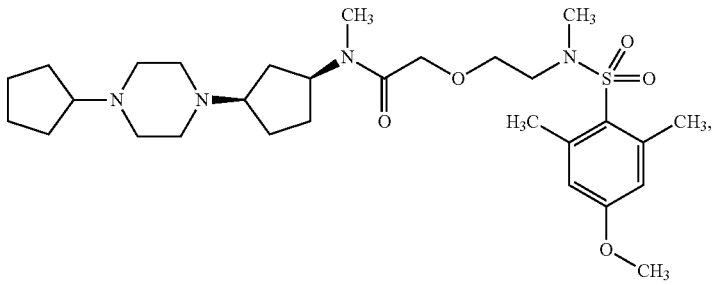 [SMILES: COc1cc(C)c(S(=O)(=O)N(C)CCOCC(=O)N(C)[C@H]2CC[C@@H](N3CCN(C4CCCC4)CC3)C2)c(C)c1] |

| No. | Structure |
|---|---|
| (26) | 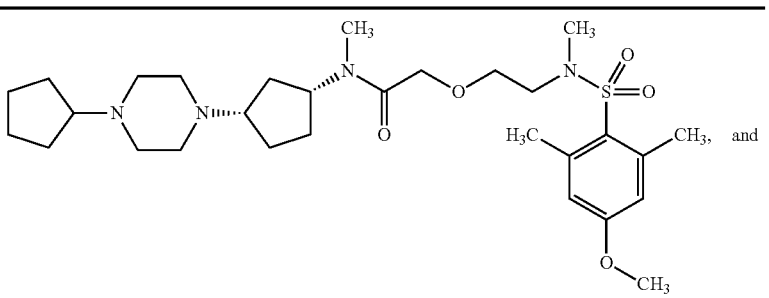 and |
| (27) | 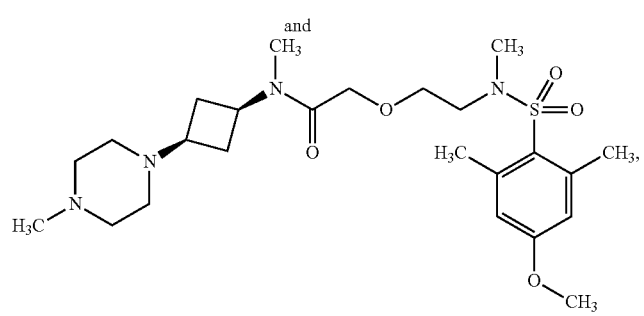 |
or a salt thereof.
7. A physiologically acceptable salt of a compound according to claim 1, 2, 3, 4, 5 or 6.
8. A pharmaceutical composition comprising a compound according to claim 1, 2, 3, 4, 5 or 6 or a physiologically acceptable salt thereof together with an inert carrier or diluent.
* * * * *

UNITED STATES PATENT AND TRADEMARK OFFICE
CERTIFICATE OF CORRECTION

PATENT NO. : 8,394,805 B2
APPLICATION NO. : 12/672460
DATED : March 12, 2013
INVENTOR(S) : Hauel et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 493 days.

Signed and Sealed this
Seventeenth Day of September, 2013

Teresa Stanek Rea
*Deputy Director of the United States Patent and Trademark Office*